(12) United States Patent
Nordling et al.

(10) Patent No.: US 9,982,022 B2
(45) Date of Patent: May 29, 2018

(54) BINDING POLYPEPTIDES HAVING A MUTATED SCAFFOLD

(71) Applicant: AFFIBODY AB, Solna (SE)

(72) Inventors: Erik Nordling, Danderyd (SE); Joakim Nilsson, Danderyd (SE); Patrik Strömberg, Sollentuna (SE)

(73) Assignee: AFFIBODY AB, Solna (SE)

( * ) Notice: Subject to any disclaimer, the term of this patent is extended or adjusted under 35 U.S.C. 154(b) by 347 days.

(21) Appl. No.: 14/911,319

(22) PCT Filed: Aug. 28, 2014

(86) PCT No.: PCT/EP2014/068259
§ 371 (c)(1),
(2) Date: Feb. 10, 2016

(87) PCT Pub. No.: WO2015/028550
PCT Pub. Date: Mar. 5, 2015

(65) Prior Publication Data
US 2016/0200772 A1    Jul. 14, 2016

(30) Foreign Application Priority Data
Aug. 28, 2013   (EP) .................................. 13182022

(51) Int. Cl.
*C07K 14/31* (2006.01)
*C07K 14/00* (2006.01)
*C12Q 1/68* (2018.01)
*G01N 33/68* (2006.01)
*C07K 1/04* (2006.01)

(52) U.S. Cl.
CPC ............ *C07K 14/001* (2013.01); *C07K 1/047* (2013.01); *C07K 14/31* (2013.01); *C12Q 1/6874* (2013.01); *G01N 33/6845* (2013.01); *C07K 2319/00* (2013.01)

(58) Field of Classification Search
None
See application file for complete search history.

(56) References Cited

U.S. PATENT DOCUMENTS

| 9,187,535 B2 | 11/2015 | Lindborg et al. |
| 2005/0090448 A1 | 4/2005 | Johnson et al. |
| 2015/0011474 A1 | 1/2015 | Berghard et al. |
| 2016/0311870 A1 | 10/2016 | Nilsson et al. |

FOREIGN PATENT DOCUMENTS

| WO | 03015819 A1 | 2/2003 |
| WO | 2005023866 A2 | 3/2005 |
| WO | 2005075507 | 8/2005 |
| WO | 2007028968 A1 | 3/2007 |
| WO | 2007106585 A1 | 9/2007 |
| WO | 2009077175 A1 | 6/2009 |
| WO | 2010015608 A1 | 2/2010 |
| WO | 2011063980 A1 | 6/2011 |
| WO | 2012004384 A2 | 1/2012 |
| WO | 2013126006 A1 | 8/2013 |

OTHER PUBLICATIONS

Frankel et al.; "Characterization of diphtheria fusion proteins targeted to the human interleukin-3 receptor"; Protein Eng., vol. 13, No. 8; 2000; pp. 575-581.
Paukla et al.; Abstract of "Genetic analysiws of protein stability and function"; Annu. Rev. Genet., vol. 23; 1989; 1 page.
International Preliminary Report on Patentability for International Application No. PCT/EP2014/068259; International Filing Date Aug. 28, 2014; dated Mar. 10, 2016; 5 pages.
International Preliminary Report on Patentability for International Application No. PCT/EP2014/068282; International Filing Date Aug. 28, 2014; dated Nov. 5, 2015; 10 pages.
International Search Report and Written Opinion of the International Searching Authority for International Application No. PCT/EP2014/068282; International Filing Date Aug. 28, 2014; dated Jan. 7, 2015; 14 pages
International Search Report for the International Searching Authority for International Patent Application No. PCT/SE2013/050139; International Filing Date: Feb. 19, 2013; dated May 28, 2013; 6 Pages.
Larghi et al., "Modulatiors of Complement Activation: A Patent Review", Expert Opinion on Therapeutic Patents; vol. 24; No. 6; Jun. 1, 2014; pp. 665-686.
Stromberg et al., "Development of Affibody C5 Inhibitors for Versatile and Efficient Therapeutic Targeting of the Terminal Complement Pathway", Abstracts/Molecular Immunology; vol. 61; No. 2; Oct. 1, 2014; p. 256.
Supplementary European Search Report of the European Searching Authority for European Patent Application No. 13752233.0; dated Aug. 5, 2015; 10 Pages.

(Continued)

*Primary Examiner* — Christopher M Gross
(74) *Attorney, Agent, or Firm* — Cantor Colburn LLP

(57) ABSTRACT

The present disclosure relates to a class of engineered polypeptides and provides a polypeptide comprising the sequence $EX_2X_3X_4AX_6X_7EIX_{10}X_{11}LPNLX_{16}X_{17}X_{18}QX_{20}$ $X_{21}AFIX_{25}X_{26}LX_{28}X_{29}X_{30}PX_{32}QSX_{35}X_{36}LLX_{39}E$ $AKKLX_{45}X_{46}X_{47}Q$ (SEQ ID NO: 55). The present disclosure also relates to populations of polypeptide variants based on a common scaffold, each polypeptide in the population comprising the amino acid sequence $EX_2X_3X_4AX_6X_7EIX_{10}X_{11}LPNLX_{16}X_{17}X_{18}QX_{20}$ $X_{21}AFIX_{25}X_{26}LX_{28}X_{29}X_{30}PX_{32}QSX_{35}X_{36}LLX_{39}E$ $AKKLX_{45}X_{46}X_{47}Q$ (SEQ ID NO: 55), and methods for selecting a desired polypeptide having an affinity for a predetermined target from said population.

16 Claims, 20 Drawing Sheets

(56) References Cited

OTHER PUBLICATIONS

Written Opinion of the International Preliminary Examining Authority for International Application No. PCT/EP2014/068282; International Filing Date Aug. 28, 2014; dated Jul. 30, 2015; 8 pages.
Written Opinion of the International Sarching Authority for International Patent Application No. PCT/SE2013/050139; International Filing Date: Feb. 19, 2013; dated May 28, 2013; 5 Pages.
"Mutant *Streptococcus* G148 ABD/SPA Z domain fusion protein"; XP002731913; retreived from EBI accession No. GSP: AAB01886
International Search Report for International Application No. PCT/EP2014/068259; International Filing Date Aug. 28, 2014; dated Nov. 18, 2014; 4 pages
Written Opinion for International Application No. PCT/EP2014/068259; International Filing Date Aug. 28, 2014; dated Nov. 18, 2014; 4 pages.

| Designation | Amino acid sequence | SEQ ID NO: |
|---|---|---|
| PSI0242 | AEAKYAKEVLEAWDEIDRLPNLTIEQWLAFINKLDDDPSQSSELLSEAKKLNDSQAPKVDGSLAEAKEAANAELDSYGVSDFYK RLIDKAKTVEGVEALKDAILAALP | 1 |
| ABD | LAEAKEAANAELDSYGVSDFYKRLIDKAKTVEGVEALKDAILAALP | 2 |
| Human C5 | MGLLGILCFLIFLGKTWGQEQTYVISAPKIFRVGASENIVIQVYGYTEAFDATISIKSYPDKKFSYSSGHVHLSSENKFQ NSAILTIQPKQLPGGQNPVSYVYLEVVSKHFSKSKRMPITYDNGFLFIHTDKPVTPDQSVKVRVYSLNDDLKPAKRETV LTFIDPEGSEVDMVEEIDHIGIISFPDFKIPSNPRYGMWTIKAKYKEDFSTTGTAYFEVKEYVLPHFSVSIEPEYNFIGY KNFKNFEITIKARYFYNKVVTEADVYITFGIREDLKDDQKEMMQTAMQNTMLINGIAQVTFDSETAVKELSYYSLEDLNN KYLYIAVTVIESTGGFSEEAEIPGIKYVLSPYKLNLVATPLFLKPGIPYPIKVQVKDSLDQLVGGVPVTLNAQTIDVNQE TSDLDPSKSVTRVDDGVASFVLNLPSGVTVLEFNVKTDAPDLPEENQAREGYRAIAYSSLSQSYLYIDWTDNHKALLVGE HLNIIVTPKSPYIDKITHYNYLILSKGKIIHFGTREKFSDASYQSINIPVTQNMVPSSRLLVYYIVTGEQTAELVSDSVW LNIEEKCGNQLQVHLSPDADAYSPGQTVSLNMATGMDSWVALAAVDSAVYGVQRGAKKPLERVFQFLEKSDLGCGAGGGL NNANVFHLAGLTFLTNANADDSQENDEPCKEILRPRRTLQKKIEEIAAKYKHSVVKKCCYDGACVNNDETCEQRAARISL GPRCIKAFTECCVVASQLRANISHKDMQLGRLHMKTLLPVSKPEIRSYFPESWLWEVHLVPRRKQLQFALPDSLTTWEIQ GVGISNTGICVADTVKAKVFKDVFLEMNIPYSVVRGEQIQLKGTVYNYRTSGMQFCVKMSAVEGICTSESPVIDHQGTKS SKCVRQKVEGSSSHLVTFTVLPLEIGLHNINFSLETWFGKEILVKTLRVVPEGVKRESYSGVTLDPRGIYGTISRRKEFP YRIPLDLVPKTEIKRILSVKGLLVGEILSAVLSQEGINILTHLPKGSAEAELMSVVPVFYVFHYLETGNHWNIFHSDPLI EKQKLKKKLKEGMLSIMSYRNADYSYSVWKGGSASTWLTAFALRVLGQVNKYVEQNQNSICNSLLWLVENYQLDNGSFKE NSQYQPIKLQGTLPVEARENSLYLTAFTVIGIRKAFDICPLVKIDTALIKADNFLLENTLPAQSTFTLAISAYALSLGDK THPQFRSIVSALKREALVKGNPPIYRFWKDNLQHKDSSVPNTGTARMVETTAYALLTSLNLKDINYVNPVIKWLSEEQRY GGGFYSTQDTINAIEGLTEYSLLVKQLRLSMDIDVSYKHKGALHNYKMTDKNFLGRPVEVLLNDDLIVSTGFGSGLATVH VTTVHKTSTSEEVCSFYLKIDTQDIEASHYRGYGNSDYKRIVACASYKPSREESSSGSSHAVMDISLPTGISANEEDLK ALVEGVDQLFTDYQIKDGHVIIQLNSIPSSDFLCVRFRIFELFEVGFLSPATFTVYEYHRPDKQCTMFYSTSNIKIQKVC EGAACKCVEADCGQMQEELDLTISAETRKQTACKPEIAYAYKVSITSITVENVFVKYKATLLDIYKTGEAVAEKDSEITF IKKVTCTNAELVKGRQYLIMGKEALQIKYNFSFRYIYPLDSLTTWIEYWPRDTTCSSCQAFLANLDEFAEDIFLNGC | 3 |
| PSI0332 | AEAKYAKEVLEAWDEIDRLPNLTIEQWLAFINKLDDDPSQSSELLSEAKKLNDSQAPKVDGSLAEAKEAANAELDSYGVSDFYK RLIDKAKTVEGVEALKDAILAALP | 4 |
| PSI0334 | AEAKYAKEVLEAWDEIDRLPNLTIEQWLAFINKLDDDPSQSSELLSEAKKLSESQAPKVDGSLAEAKEAANAELDSYGVSDFYK RLIDKAKTVEGVEALKDAILAALP | 5 |
| PSI0335 | AEAKYAKEVLEAWDEIDRLPNLTIEQWLAFINKLDDDPSQSSELLSEAKKLNDSQAPKVDGSLAEAKVLANRELDKYGVSDFYK RLINKAKTVEGVEALKHILAALP | 6 |
| PSI0336 | AEAKYAKEVLEAWSEIDRLPNLTIEQWLAFINKLDDDPSQSSELLSEAKKLNDSQAPKVDGSLAEAKEAANAELDSYGVSDFYK RLIDKAKTVEGVEALKDAILAALP | 7 |
| PSI0337 | AEAKYAKEVLEAWDEIDRLPNLTIEQWLAFINKLDDDPSQSSELLSEAKKLNDSQAPKVDGSLAEAKEAANAELDSYGVSDFYK RLIDKAKTVEGVEALKDAILAALP | 8 |

Figure 1A

| Designation | Amino acid sequence | SEQ ID NO: |
|---|---|---|
| PSI0339 | AEAKYAKEVLEAWDEIDRLPNLTIEQWLAFIAKLDDDPSQSSELLSEAKKLNDSQAPKVDGSLAEAKEAANAELDSYGVSDFYK RLIDKAKTVEGVEALKDAILAALP | 9 |
| PSI0340 | AEAKYAKEVLEAWDEIDRLPNLTIEQWLAFINKLEDDPSQSSELLSEAKKLNDSQAPKVDGSLAEAKEAANAELDSYGVSDFYK RLIDKAKTVEGVEALKDAILAALP | 10 |
| PSI0369 | AEAKYAKEVLEAWDEIDRLPNLTIEQWLAFINKLDDDPSQSSELLSEAKKLNDSQAPLAEAKEAANAELDSYGVSDFYKRLIDK AKTVEGVEALKDAILAALP | 11 |
| PSI0377 | AEAKYAKEVLEAWDEIDRLPNLTIEQWLAFINKLDDDPSQSSELLSEAKKLSESQAP | 12 |
| PSI0378 | AEAKYAKEVLEAWDEIDRLPNLTIEQWLAFINKLDDDPSQSSELLSEAKKLSESQAPKVEGSLAEAKEAANAELDSYGVSDFYK RLIDKAKTVEGVEALKDAILAALP | 13 |
| PSI0379 | AEAKYAKEVLEAWDEIDRLPNLTIEQWLAFINKLDDDPSQSSELLSEAKKLSESQAPKVAGSLAEAKEAANAELDSYGVSDFYK RLIDKAKTVEGVEALKDAILAALP | 14 |
| PSI0381 | AEAKYAKEVLEAWDEIDRLPNLTIEQWLAFINKLDDDPSQSSELLSEAKKLESSQAPKVEGSLAEAKEAANAELDSYGVSDFYK RLIDKAKTVEGVEALKDAILAALP | 15 |
| PSI0383 | AEAKYAKEVLEAWDEIDRLPNLTIEQWLAFINKLDRQPEQSSELLSEAKKLSESQAPKVEGSLAEAKEAANAELDSYGVSDFYK RLIDKAKTVEGVEALKDAILAALP | 16 |
| PSI0389 | AEAKYAKEVLEAWDEIDRLPNLTIEQWLAFINKLDDDPSQSSELLSEAKKLESSQAP | 17 |
| PSI0390 | AEAKYAKEVLEAWDEIDRLPNLTIEQWLAFINKLDRQPEQSSELLSEAKKLSESQAP | 18 |
| PSI0377_PP | EVLEAWDEIDRLPNLTIEQWLAFINKLDDDPSQSSELLSEAKKLSESQ | 19 |
| PSI0389_PP | EVLEAWDEIDRLPNLTIEQWLAFINKLDDDPSQSSELLSEAKKLESSQ | 20 |
| PSI0390_PP | EVLEAWDEIDRLPNLTIEQWLAFINKLDRQPEQSSELLSEAKKLSESQ | 21 |
| PSI0400 | AEAKYAKEVLEAWDEIDRLPNLTIEQWLAFINKLDDDPSQSSELLSEAKKLSESQAPK | 22 |
| PSI0410 | AEAKYAKEVLEAWDEIDRLPNLTIEQWLAFINKLDDDPSQSSELLSEAKKLNDSQAPKVEGSLAEAKEAANAELDSYGVSDFYK RLIDKAKTVEGVEALKDAILAALP | 23 |
| PSI0403 | AEAKYAKEVLEAWDEIDRLPNLTIEQWLAFINKLDDDPSQSSELLSEAKKLNESQAPKVEGSLAEAKEAANAELDSYGVSDFYK RLIDKAKTVEGVEALKDAILAALP | 24 |
| PSI0404 | AEAKYAKEVLEAWDEIDRLPNLTIEQWLAFINKLDDDPSQSSELLSEAKKLSDSQAPKVEGSLAEAKEAANAELDSYGVSDFYK RLIDKAKTVEGVEALKDAILAALP | 25 |
| PSI0257 | AEAKYAKEVLEAWDEIDRLPNLTIEQWLAFINKLDDDPSQSSELLSEAKKLNDSQAPKVDGS | 26 |
| Z02891 | AEAKYAKEMRNAYWEIALLPNLTNQQKRAFIRKLYDDPSQSSELLSEAKKLNDSQAPK | 27 |
| Z17341 | AEAKYAKEMRNAYWEIALLPNLTNQQKRAFIRKLYDDPSQSSELLSEAKKLSESQAPK | 28 |
| Z17342 | AEAKYAKEMRNAYWEIALLPNLTNQQKRAFIRKLYRQPEQSSELLSEAKKLSESQAPK | 29 |
| Z15805 | AEAKYAKELIEAAAEIDALPNLTRRQWNAFIKKLVDDPSQSSELLSEAKKLNDSQAPK | 30 |
| Z17343 | AEAKYAKELIEAAAEIDALPNLTRRQWNAFIKKLVDDPSQSSELLSEAKKLSESQAPK | 31 |

Figure 1B

| Designation | Amino acid sequence | SEQ ID NO: |
|---|---|---|
| Z17344 | AEAKYAKELIEAAAEIDALPNLTRRQWNAFIKKLVRQPEQSSELLSEAKKLSESQAPK | 32 |
| Z10103 | AEAKYAKEQDAAAHEIRWLPNLTFDQRVAFIHKLADDPSQSSELLSEAKKLNDSQAPK | 33 |
| Z17347 | AEAKYAKEQDAAAHEIRWLPNLTFDQRVAFIHKLADDPSQSSELLSEAKKLSESQAPK | 34 |
| Z17348 | AEAKYAKEQDAAAHEIRWLPNLTFDQRVAFIHKLARQPEQSSELLSEAKKLSESQAPK | 35 |
| Z09782 | AEAKYAKENLFAGWEISDLPNLTDYQRNAFIYKLWDDPSQSSELLSEAKKLNDSQAPK | 36 |
| Z17351 | AEAKYAKENLFAGWEISDLPNLTDYQRNAFIYKLWDDPSQSSELLSEAKKLSESQAPK | 37 |
| Z17352 | AEAKYAKENLFAGWEISDLPNLTDYQRNAFIYKLWRQPEQSSELLSEAKKLSESQAPK | 38 |
| Z17355 | AEAKYAKENLFAGWEISDLPNLTDYQRNAFIYKLWDDPSQSSELLSEAKKLNESQAPK | 39 |
| Z17357 | AEAKYAKENLFAGWEISDLPNLTDYQRNAFIYKLWRQPEQSSELLSEAKKLNESQAPK | 40 |
| Z17359 | AEAKYAKENLFAGWEISDLPNLTDYQRNAFIYKLWDDPSQSSELLSEAKKLSDSQAPK | 41 |
| Z17360 | AEAKYAKENLFAGWEISDLPNLTDYQRNAFIYKLWRQPEQSSELLSEAKKLSDSQAPK | 42 |
| Z17341_PP | EMRNAYWEIALLPNLTNQQKRAFIRKLYDDPSQSSELLSEAKKLSESQ | 43 |
| Z17342_PP | EMRNAYWEIALLPNLTNQQKRAFIRKLYRQPEQSSELLSEAKKLSESQ | 44 |
| Z17343_PP | ELIEAAAEIDALPNLTRRQWNAFIKKLVDDPSQSSELLSEAKKLSESQ | 45 |
| Z17344_PP | ELIEAAAEIDALPNLTRRQWNAFIKKLVRQPEQSSELLSEAKKLSESQ | 46 |
| Z17347_PP | EQDAAAHEIRWLPNLTFDQRVAFIHKLADDPSQSSELLSEAKKLSESQ | 47 |
| Z17348_PP | EQDAAAHEIRWLPNLTFDQRVAFIHKLARQPEQSSELLSEAKKLSESQ | 48 |
| Z17351_PP | ENLFAGWEISDLPNLTDYQRNAFIYKLWDDPSQSSELLSEAKKLSESQ | 49 |
| Z17352_PP | ENLFAGWEISDLPNLTDYQRNAFIYKLWRQPEQSSELLSEAKKLSESQ | 50 |
| Z17355_PP | ENLFAGWEISDLPNLTDYQRNAFIYKLWDDPSQSSELLSEAKKLNESQ | 51 |
| Z17357_PP | ENLFAGWEISDLPNLTDYQRNAFIYKLWRQPEQSSELLSEAKKLNESQ | 52 |
| Z17359_PP | ENLFAGWEISDLPNLTDYQRNAFIYKLWDDPSQSSELLSEAKKLSDSQ | 53 |
| Z17360_PP | ENLFAGWEISDLPNLTDYQRNAFIYKLWRQPEQSSELLSEAKKLSDSQ | 54 |

BINDING POLYPEPTIDES HAVING A MUTATED SCAFFOLD

CROSS-REFERENCE TO RELATED APPLICATIONS

This Application is a U.S. National Stage Application of PCT/EP2014/068259 filed Aug. 28, 2014 which claims priority to EP Application No. 13182022.7 filed Aug. 28, 2013, both of which are incorporated by reference in their entireties.

FIELD OF THE INVENTION

The present invention relates to novel polypeptides, methods of production thereof and novel populations of polypeptide variants based on a common scaffold. The populations can for example be used to provide novel binding proteins and polypeptides.

BACKGROUND

Different methods for construction of novel binding proteins have been described (Nygren P A and Uhlén M (1997) Curr Opin Struct Biol 7:463-469). One strategy has been to combine library generation and screening with selection for desired properties.

First generation Z variant polypeptides based on a common, first generation scaffold, populations of such molecules and methods involving them have been described in WO95/19374. Additionally, Z variant polypeptides based on a second generation scaffold, populations of such molecules and methods involving them have been described in WO2009/080811. The teachings of these two disclosures are incorporated herein by reference.

For some applications, Z variant polypeptides or populations thereof having improved properties, such as higher alkali stability, low antigenicity, structural stability, amenability to chemical synthesis and hydrophilicity, are desired. WO2009/080811 discloses Z variants having a common scaffold with improved properties, but not every desired property can be obtained by Z variant polypeptides as described therein.

One of the key factors to success for polypeptide pharmaceuticals is their stability. Polypeptides showing a high structural stability will most likely functionally withstand chemical modifications, changes in physical conditions and proteolysis, both during production as well as within the human body. Moreover, stability will influence the active shelf-life of polypeptide pharmaceuticals, as well as the active life of the polypeptide pharmaceutical within the human body.

Hence, there is a continued need for improving the stability of Z variant polypeptides.

DESCRIPTION OF THE INVENTION

It is an object of the present invention to provide a polypeptide with a novel scaffold, which polypeptide alleviates the above-mentioned and other drawbacks of currently available Z variant polypeptides.

Another object of the present invention is to provide a method for production of a polypeptide based on a novel scaffold.

It is also an object of the present invention to provide a population of such improved polypeptide variants, all based on a novel scaffold.

Another object of the present invention is to provide a population of polynucleotides.

Yet another object of the present invention is to provide a combination of a polypeptide population and a polynucleotide population.

A further object of the present invention is to provide a method for selecting a desired polypeptide having an affinity for a predetermined target from a population of polypeptides.

Another object is to provide a method for isolating a polynucleotide encoding a desired polypeptide having an affinity for a predetermined target.

Another object is to provide a method for identifying a desired polypeptide having an affinity for a predetermined target.

A further object is to provide a method for selecting and identifying a desired polypeptide having an affinity for a predetermined target.

A related object is to provide a method for production of a desired polypeptide having an affinity for a predetermined target.

These and other objects may be achieved by different aspects disclosed in the present application.

In a first aspect of the present disclosure, there is provided a polypeptide comprising an amino acid sequence selected from i)

(SEQ ID NO: 55)
$EX_2X_3X_4AX_6X_7EIX_{10}$ $X_{11}LPNLX_{16}X_{17}X_{18}QX_{20}X_{21}AFIX_{25}$ $X_{26}LX_{28}X_{29}X_{30}$ $PX_{32}QSX_{35}X_{36}LLX_{39}E$ $AKKLX_{45}X_{46}X_{47}Q$, wherein each of $X_2$, $X_3$, $X_4$, $X_6$, $X_7$, $X_{10}$, $X_{11}$, $X_{17}$, $X_{18}$, $X_{20}$, $X_{21}$, $X_{25}$ and $X_{28}$ independently corresponds to any amino acid residue; and wherein, independently of each other, $X_{16}$ is selected from N and T;

$X_{26}$ is selected from K and S;

$X_{29}X_{30}PX_{32}$ is selected from DDPS and RQPE;

$X_{35}$ is selected from A and S;

$X_{36}$ is selected from E and N;

$X_{39}$ is selected from A, C and S;

$X_{45}$ is selected from E, N and S;

$X_{46}$ is selected from D, E and S, provided that $X_{46}$ is not D when $X_{45}$ is N;

$X_{47}$ is selected from A and S; and ii) an amino acid sequence which has at least 91% identity to the sequence defined in i), provided that $X_{46}$ is not D when $X_{45}$ is N.

Within the polypeptide sequence i) above, each amino acid X defined as "independently corresponding to any amino acid" individually corresponds to an amino acid residue which is selected from all possible amino acids. For clarity, this applies to amino acid positions corresponding to the positions $X_2$, $X_3$, $X_4$, $X_6$, $X_7$, $X_{10}$, $X_{11}$, $X_{17}$, $X_{18}$, $X_{20}$, $X_{21}$, $X_{25}$ and $X_{28}$ in sequence i) above. This means that each such X may be any amino acid residue, independent of the identity of any other residue denoted X in the sequence. In the amino acid sequence, these amino acids X may be chosen from all 20 naturally occurring amino acid residues in such a way that any of these 20 naturally occurring amino acid residues may be present at the corresponding X position in any given variant. The selection of amino acid residue in each position may be more or less randomized. It is also possible to limit the group from which the different varied amino acid residues are selected to 19, 18, 17, 16 or less of the 20 naturally occurring amino acid residues. The variability in different positions may be adjusted individually, between one, meaning no randomization, up to all 20 amino acids. Random introduction of a smaller subset of amino acids may be obtained by careful selection of the deoxyribonucleotide bases introduced, for example the codons T(A/C)C may be introduced to obtain a random introduction of either serine or tyrosine at a given position in the polypeptide chain. Likewise, the codons (T/C/A/G)CC may be introduced to obtain a random introduction of phenylalanine, leucine, alanine and valine at a given position in the polypeptide chain. The skilled person is aware of many alternatives of deoxyribonucleotide base combinations that may be used to obtain different combinations of amino acids at a given position in the polypeptide chain. The set of amino acids that may appear at a given position in the polypeptide chain may also be determined by the introduction of trinucleotides during the oligonucleotide synthesis, instead of one deoxyribonucleotide base at a time. A defined set of amino acids may also be obtained using split-pool synthesis enabling incorporation of defined codons in desirable positions in the synthesis. Yet another alternative to obtain randomized double stranded linkers is by incorporation of randomized sets of trinucleotide building blocks using ligations and restrictions of the subsequently built up double stranded DNA.

In one embodiment of the present disclosure, there is provided a polypeptide having affinity for a predetermined target. In one such embodiment, the amino acid residues that confer target binding specificity are those in the positions corresponding to positions 2, 3, 4, 6, 7, 10, 11, 17, 18, 20, 21, 25 and 28 in sequence i) above. Likewise, in such a polypeptide, amino acid residues that do not confer target binding specificity are referred to as "scaffold amino acids" or simply "scaffold". Accordingly, in one embodiment, scaffold amino acid residues as defined herein are those in the positions corresponding to positions 1, 5, 8, 9, 12-15, 19, 22-24, 27, 31, 33-34, 37-38, 40-44 and 48 in sequence i) above. The skilled person will appreciate that the advantageous properties conferred by the scaffold amino acids of the polypeptides as defined herein are independent of the target binding specificity of said polypeptide.

As the skilled person will realize, the function of any polypeptide, such as the polypeptide of the present disclosure, is dependent on the tertiary structure of the polypeptide. It is therefore possible to make minor changes to the sequence of amino acids in a polypeptide without affecting the function thereof. Thus, the disclosure encompasses modified variants of said polypeptide that do not alter the functional properties of the polypeptide, such as its improved stability and/or its binding affinity for a predetermined target.

In this way, also encompassed by the present disclosure is a polypeptide comprising an amino acid sequence with 91% or greater identity to a sequence defined in i). In some embodiments, the polypeptide may comprise a sequence which is at least 93%, such as at least 95%, such as at least 97% identical to the sequence defined in i).

In some embodiments, such differences between sequence definitions i) and ii) may be found in any position of the sequence of the polypeptide as disclosed herein. In other embodiments, such changes may be found only in scaffold amino acid residues. In other embodiments, said changes may be found only in the amino acid residues which confer target binding specificity. For example, it is possible that an amino acid residue belonging to a certain functional grouping of amino acid residues (e.g. hydrophobic, hydrophilic, polar etc) could be exchanged for another amino acid residue from the same functional group.

The term "% identity", as used throughout the specification, may for example be calculated as follows. The query sequence is aligned to the target sequence using the CLUSTAL W algorithm (Thompson et al, Nucleic Acids Research, 22: 4673-4680 (1994)). A comparison is made over the window corresponding to one of the aligned sequences, for example the shortest. The window may in some instances be defined by the target sequence. In other instances, the window may be defined by the query sequence. The amino acid residues at each position are compared, and the percentage of positions in the query sequence that have identical correspondences in the target sequence is reported as % identity.

When used as scaffolds for binding polypeptides, the sequences disclosed herein provide advantages compared to known, similar scaffolds, and have been engineered to show a high structural stability and hence an improved storage shelf-life. These advantages also apply to the third aspect of the disclosure (see further below), which relates to populations of the polypeptide variants of this first aspect.

In one embodiment of the present disclosure, $X_{16}$ is T.
In one embodiment, $X_{26}$ is K.
In one embodiment, $X_{29}X_{30}PX_{32}$ is DDPS.
In one embodiment, $X_{29}X_{30}PX_{32}$ is RQPE.
In one embodiment, $X_{35}$ is S.
In one embodiment, $X_{36}$ is E.
In one embodiment, $X_{39}$ is S.
In one embodiment, $X_{45}$ is selected from E and S.
In one embodiment, $X_{45}$ is E.
In one embodiment, $X_{45}$ is S.
In one embodiment, $X_{46}$ is selected from E and S.
In one embodiment, $X_{46}$ is E.
In one embodiment, $X_{46}$ is S.
In one embodiment, $X_{46}$ is D.
In one embodiment, $X_{46}$ is not D or E when $X_{45}$ is N.
In one embodiment, $X_{45}X_{46}$ is selected from EE, ES, SE and SS, such as from ES and SE.
In one embodiment, $X_{45}X_{46}$ is ES.
In one embodiment, $X_{45}X_{46}$ is SE.
In one embodiment, $X_{45}X_{46}$ is SD.
In one embodiment, $X_{47}$ is S.

The term "binding affinity for a predetermined target" as used in this specification refer to a property of a polypeptide which may be tested for example by the use of surface plasmon resonance (SPR) technology. For example, said binding affinity may be tested in an experiment in which the predetermined target, or a fragment thereof, is immobilized on a sensor chip of the instrument, and the sample containing the polypeptide to be tested is passed over the chip. Alternatively, the polypeptide to be tested is immobilized on a sensor chip of the instrument, and a sample containing the predetermined target, or a fragment thereof, is passed over the chip. The skilled person may then interpret the results obtained by such experiments to establish at least a qualitative measure of the binding affinity of the polypeptide for the predetermined target. If a quantitative measure is desired, for example to determine a $K_D$ value for the interaction, surface plasmon resonance methods may also be used. Binding values may for example be defined in a Biacore (GE Healthcare) or ProteOn XPR 36 (Bio-Rad) instrument. The predetermined target is suitably immobilized on a sensor chip of the instrument, and samples of the polypeptide whose affinity is to be determined are prepared by serial dilution and injected in random order. $K_D$ values may then be calculated from the results using for example the 1:1 Langmuir binding model of the BIAevaluation 4.1 software, or other suitable software, provided by the instrument manufacturer.

The term "binding affinity for a predetermined target", as used herein, may also refer to a property of a polypeptide which may be tested for example by ELISA. For example, the binding affinity may be tested in an experiment in which samples of the polypeptide are captured on antibody-coated ELISA plates and biotinylated predetermined target, or a fragment thereof, is added, followed by streptavidin conjugated HRP. TMB substrate is added and the absorbance at 450 nm is measured using a multi-well plate reader, such as Victor$^3$ (Perkin Elmer). The skilled person may then interpret the results obtained by such experiments to establish at least a qualitative measure of the binding affinity of the complex for the predetermined target. If a quantitative measure is desired, for example to determine the EC50 value (the half maximal effective concentration) for the interaction, ELISA may also be used. The response of the polypeptide against a dilution series of the predetermined target, or a fragment thereof, is measured using ELISA as described above. The skilled person may then interpret the results obtained by such experiments, and EC50 values may be calculated from the results using for example GraphPad Prism 5 and non-linear regression.

As previously described, Z variant polypeptides are believed to constitute, or form part of, a three-helix bundle protein domain, the motif having affinity for a predetermined target essentially forming part of two alpha helices with an interconnecting loop, within said three-helix bundle protein domain.

Different modifications of, and/or additions to, the polypeptide as defined above may be performed in order to tailor the polypeptide to the specific use intended, without departing from the scope of the present invention.

Such modifications and additions are described in more detail below, and may comprise additional amino acids comprised in the same polypeptide chain, or labels and/or therapeutic agents that are chemically conjugated or otherwise bound to the polypeptide.

Hence, in one embodiment, there is provided a polypeptide as described above comprising additional amino acid residues. In some embodiments additional amino acid residues may be located at the C-terminus of the polypeptide. In some embodiments additional amino acid residues may be located at the N-terminus of the polypeptide.

In one embodiment, said additional amino acid residues at the C-terminus comprise AP.

In one embodiment, said additional amino acid residues at the N-terminus comprise AEAKYAK.

In yet another embodiment, there is provided a polypeptide as described above, which consists of sequence i) or ii) having from 0 to 7 additional amino acid residues at the N-terminus and from 0 to 3 additional amino acid residues at the C-terminus.

The additional amino acid residues may play a role in the binding of the polypeptide, but may equally well serve other purposes, related for example to one or more of the production, purification, stabilization, coupling or detection of the polypeptide. In some embodiments, said additional amino acid residues constitute one or more polypeptide domain(s).

Such additional amino acid residues may comprise one or more amino acid residues added for purposes of chemical coupling. An example of this is the addition of a cysteine residue at the very first or very last position in the polypeptide chain, i.e. at the N- or C-terminus. A cysteine residue to be used for chemical coupling may also be introduced by replacement of another amino acid on the surface of the protein domain, preferably on a portion of the surface that is not involved in target binding. Such additional amino acid residues may also comprise a "tag" for purification or detection of the polypeptide, such as a hexahistidyl (His$_6$) tag, or a "myc" tag or a "FLAG" tag for interaction with antibodies specific to the tag. The skilled person is aware of other alternatives.

The "additional amino acid residues" discussed above may also constitute one or more polypeptide domain(s) with any desired function, such as another binding function, or a half-life extending function, or an enzymatic function, or a metal ion chelating function, or a fluorescent function, or any combination thereof.

In one example embodiment, there is provided a compound having affinity for a predetermined target, said compound comprising:

A. at least one polypeptide as defined above;

B. at least one albumin binding domain of streptococcal protein G, or a derivative thereof; and C. optionally, at least one linking moiety for linking said at least one albumin binding domain or derivative thereof to the C or N terminus of said at least one polypeptide.

Non-limiting examples of derivatives of the albumin binding domain of streptococcal protein G are disclosed in WO2009/016043 and WO2012/004384.

Also, in a further embodiment, there is provided a polypeptide as defined above, which comprises an amino acid sequence selected from:

(SEQ ID NO: 56)
YAK EX$_2$X$_3$X$_4$AX$_6$X$_7$EIX$_{10}$ X$_{11}$LPNLX$_{16}$X$_{17}$X$_{18}$QX$_{20}$

X$_{21}$AFIX$_{25}$X$_{26}$LX$_{28}$X$_{29}$X$_{30}$ PX$_{32}$QSX$_{35}$X$_{36}$LLX$_{39}$E

AKKLX$_{45}$X$_{46}$X$_{47}$Q AP;
and (SEQ ID NO: 57)
FNK EX$_2$X$_3$X$_4$AX$_6$X$_7$EIX$_{10}$ X$_{11}$LPNLX$_{16}$X$_{17}$X$_{18}$QX$_{20}$ X$_{21}$AFIX$_{25}$X$_{26}$LX$_{28}$X$_{29}$X$_{30}$ PX$_{32}$QSX$_{35}$X$_{36}$LLX$_{39}$E

AKKLX$_{45}$X$_{46}$X$_{47}$Q AP.

wherein each X$_y$ is defined as above (and y denotes the amino acid position of residue X within the polypeptide sequence defined by i) above).

In some embodiments, there is provided a polypeptide, which comprises an amino acid sequence selected from (SEQ ID NO: 58)
ADNNFNK EX$_2$X$_3$X$_4$AX$_6$X$_7$EIX$_{10}$ X$_{11}$LPNLX$_{16}$X$_{17}$X$_{18}$QX$_{20}$ X$_{21}$AFIX$_{25}$X$_{26}$LX$_{28}$X$_{29}$X$_{30}$ PX$_{32}$QSX$_{35}$X$_{36}$LLX$_{39}$E

AKKLX$_{45}$X$_{46}$X$_{47}$Q APK;

(SEQ ID NO: 59)
ADNKFNK EX$_2$X$_3$X$_4$AX$_6$X$_7$EIX$_{10}$ X$_{11}$LPNLX$_{16}$X$_{17}$X$_{18}$QX$_{20}$

X$_{21}$AFIX$_{25}$X$_{26}$LX$_{28}$X$_{29}$X$_{30}$ PX$_{32}$QSX$_{35}$X$_{36}$LLX$_{39}$E

AKKLX$_{45}$X$_{46}$X$_{47}$Q APK;

(SEQ ID NO: 60)
VDNKFNK EX$_2$X$_3$X$_4$AX$_6$X$_7$EIX$_{10}$ X$_{11}$LPNLX$_{16}$X$_{17}$X$_{18}$QX$_{20}$

X$_{21}$AFIX$_{25}$X$_{26}$LX$_{28}$X$_{29}$X$_{30}$ PX$_{32}$QSX$_{35}$X$_{36}$LLX$_{39}$E

AKKLX$_{45}$X$_{46}$X$_{47}$Q APK;

```
                                          (SEQ ID NO: 61)
VDAKYAK EX2X3X4AX6X7EIX10 X11LPNLX16X17X18QX20

X21AFIX25X26LX28X29X30 PX32QSX35X36LLX39E

AKKLX45X46X47Q APK;
and
                                          (SEQ ID NO: 62)
AEAKYAK EX2X3X4AX6X7EIX10 X11LPNLX16X17X18QX20

X21AFIX25X26LX28X29X30 PX32QSX35X36LLX39E

AKKLX45X46X47Q APK;
``` wherein $X_y$ is defined as described above (and y denotes the amino acid position of residue X within the polypeptide sequence defined by i) above).

The polypeptide variants disclosed herein may be generated by taking a Z variant polypeptide, for example based on a known scaffold and having affinity for a given target, and performing site-directed mutagenesis at selected positions to obtain a polypeptide having a scaffold according to the present disclosure, retaining the target affinity. A polypeptide according to the present disclosure may, alternatively, be made by chemical synthesis of the entire molecule or by using other molecular biology methods, known to a person skilled in the art, to graft the binding motif of a Z variant polypeptide onto the scaffold disclosed herein.

As a general illustration, original Z variant polypeptides comprising the following common scaffold sequence and having a binding specificity defined by the amino acid sequence within a binding motif [BM]:

```
                                          (SEQ ID NO: 63)
AEAKYAK-[BM]-DDPSQSSELL SEAKKLNDSQ APK
``` may be modified to provide a polypeptide as disclosed herein.

In various specific embodiments of this aspect of the disclosure, the following polypeptides are provided:

```
                                          (SEQ ID NO: 64)
AEAKYAK-[BM]-RQPEQSSELL SEAKKLNDSQ APK (SEQ ID NO: 65)
AEAKYAK-[BM]-DDPSQSSELL SEAKKLSESQ APK (SEQ ID NO: 66)
AEAKYAK-[BM]-DDPSQSSELL SEAKKLESSQ APK (SEQ ID NO: 67)
AEAKYAK-[BM]-DDPSQSSELL SEAKKLSDSQ APK (SEQ ID NO: 68)
AEAKYAK-[BM]-DDPSQSSELL SEAKKLNESQ APK (SEQ ID NO: 69)
AEAKYAK-[BM]-RQPEQSSELL SEAKKLSESQ APK (SEQ ID NO: 70)
AEAKYAK-[BM]-RQPEQSSELL SEAKKLESSQ APK (SEQ ID NO: 71)
AEAKYAK-[BM]-RQPEQSSELL SEAKKLSDSQ APK (SEQ ID NO: 72)
AEAKYAK-[BM]-RQPEQSSELL SEAKKLNSSQ APK
```

The polypeptides disclosed herein have many applications, for example applications of therapeutic, diagnostic or prognostic significance for a disease. A non-limiting list of diseases, in which said polypeptides may find therapeutic, diagnostic or prognostic use, includes cancer, inflammatory diseases, autoimmune disease, infectious diseases, neurological diseases, neurodegenerative diseases, eye diseases, kidney diseases, pulmonary diseases, diseases of the gastrointestinal tract, cardiovascular diseases, hematological diseases, dermatological diseases, allergies and other.

Thus, in one embodiment, there is provided a polypeptide with affinity for a predetermined target. In more specific embodiments, said target is selected from the group consisting of HER2, TNFα, EGFR, IGF1R, IgG, PDGFRβ, HER3, C5, FcRn, CAIX, amyloid β, CD4, IL8, IL6 and insulin. In other embodiments, said polypeptide may be of use in biotechnological, industrial and pharmaceutical applications, for example use as an affinity ligand in separation technology, purification applications or as a detection agent. In a more specific such embodiment, the predetermined target may be an albumin binding domain ("ABD" or "GA module") from streptococcal Protein G, or a derivative thereof.

The skilled person will appreciate that the list of predetermined targets is to be viewed as non-limiting, and that polypeptides as defined herein with affinity for other predetermined targets fall within the scope of the present disclosure.

Non-limiting examples of known Z variant polypeptides, based on a known scaffold and having affinity for different targets, are Z variants with affinity for the EGF receptor (disclosed in WO2007/065635), for the HER2 receptor (disclosed in WO2009/080810), for the HER3 receptor (disclosed in WO2010/056124), for the IGF1 receptor (disclosed in WO2009/019117), for the PDGF receptor β (disclosed in WO2009/077175), for the albumin binding domain (ABD) (disclosed in WO2014/064237), for the neonatal Fc receptor (FcRn) (disclosed in PCT/EP2014/055299) and for carbonic anhydrase IX (disclosed in WO2014/096163). Note, for clarity, that in the present disclosure, a Z variant's binding motif [BM] corresponds to the first 28 amino acid residues of those binding motifs disclosed in the documents listed above, in which the definitions of binding motifs are 29 amino acid residues and correspond to the amino acid residues at positions corresponding to positions 1-29 of sequence i) above.

In one embodiment, there is provided a polypeptide with an affinity for a predetermined target, which further comprises a label, such as a label selected from the group consisting of fluorescent dyes and metals, chromophoric dyes, chemiluminescent compounds and bioluminescent proteins, enzymes, radionuclides and particles. Such labels may for example be used for detection of the polypeptide.

In some embodiments, the polypeptide is present as a moiety in a fusion polypeptide or conjugate also comprising a second moiety having a desired biological activity. Non-limiting examples of such a desired biological activity comprise a therapeutic activity, a binding activity, and an enzymatic activity.

In some embodiments, said moiety further comprises a label. The label may in some instances be coupled only to the polypeptide with affinity for a predetermined target, and in some instances both to the polypeptide with affinity for a predetermined target and to the second moiety of the conjugate or fusion polypeptide. Furthermore, it is also possible that the label may be coupled to a second moiety only and not to the polypeptide with affinity for a predetermined target. Hence, in yet another embodiment there is provided a polypeptide with affinity for a predetermined target comprising a second moiety, wherein said label is coupled to the second moiety only.

Herein disclosed polypeptides or fusion polypeptides may be used as detection reagents, capture reagents, as separation reagents, as diagnostic agents for diagnostics in vivo or in vitro, or as therapeutic agents. Methods that employ the polypeptides or fusion polypeptides according to the present disclosure in vitro may be performed in different formats, such as in microtiter plates, in protein arrays, on biosensor surfaces, on tissue sections, and so on.

It should also be understood that the polypeptide or fusion polypeptides according to the present disclosure may be useful as a therapeutic, diagnostic or prognostic agent in its own right or as a means for targeting other therapeutic, diagnostic or prognostic agents, with e.g. direct or indirect effects on said target. A direct therapeutic effect may for example be accomplished by inhibiting signaling by said target. Said target may also serve as a valuable marker to predict the prognosis of certain diseases (for example the diseases listed above).

Hence, in one embodiment there is provided a polypeptide or fusion polypeptide as described herein for use in therapy or for use as a diagnostic agent. In another embodiment, said polypeptide or fusion polypeptide further comprises a therapeutic agent. Non-limiting examples of such therapeutic agents are a therapeutic agent potentiating the effect of said polypeptide or fusion polypeptide, a therapeutic agent acting in synergy with said polypeptide or fusion polypeptide and a therapeutic agent affecting a different aspect of the disease to be treated. Also envisioned are pharmaceutical compositions comprising polypeptides as disclosed herein, alone or together with further therapeutic agents.

In a second aspect of the present disclosure, there is provided a polynucleotide encoding a polypeptide or a fusion polypeptide as described herein. Also encompassed by this disclosure is a method of producing a polypeptide or fusion polypeptide as described above comprising expressing such a polynucleotide; an expression vector comprising the polynucleotide; and a host cell comprising said expression vector.

In a third aspect of the present disclosure, there is provided a population of polypeptide variants based on a common scaffold, each polypeptide in the population comprising an amino acid sequence selected from:

i)

(SEQ ID NO: 55)
$EX_2X_3X_4AX_6X_7EIX_{10}$ $X_{11}LPNLX_{16}X_{17}X_{18}QX_{20}$ $X_{21}AFIX_{25}X_{26}LX_{28}X_{29}X_{30}$ $PX_{32}QSX_{35}X_{36}LLX_{39}E$ $AKKLX_{45}X_{46}X_{47}Q$, wherein each of $X_2$, $X_3$, $X_4$, $X_6$, $X_7$, $X_{10}$, $X_{11}$, $X_{17}$, $X_{18}$, $X_{20}$, $X_{21}$, $X_{25}$ and $X_{28}$ independently corresponds to any amino acid residue; and wherein, independently of each other,
$X_{16}$ is selected from N and T;
$X_{26}$ is selected from K and S;
$X_{29}X_{30}PX_{32}$ is selected from DDPS and RQPE;
$X_{35}$ is selected from A and S;
$X_{36}$ is selected from E and N;
$X_{39}$ is selected from A, C and S;
$X_{45}$ is selected from E, N and S;

$X_{46}$ is selected from D, E and S, provided that $X_{46}$ is not D when $X_{45}$ is N;
$X_{47}$ is selected from A and S; and ii) an amino acid sequence which has at least 91% identity to the sequence defined in i), provided that $X_{46}$ is not D when $X_{45}$ is N.

In sequence i) above, each of $X_2$, $X_3$, $X_4$, $X_6$, $X_7$, $X_{10}$, $X_{11}$, $X_{17}$, $X_{18}$, $X_{20}$, $X_{21}$, $X_{25}$ and $X_{28}$ individually corresponds to an amino acid residue which is varied in the population. Hence, each such amino acid residue may be any amino acid residue independent of the identity of any other residue denoted $X_y$ in the sequence, as explained above in connection with the first (polypeptide) aspect of the disclosure. Non-limiting options for specific amino acid residues $X_y$ in the population of polypeptides, and for any additional amino acid residues at either terminal of sequence i) or ii), are the same as those listed above as embodiments of the first aspect of the disclosure.

As discussed above, polypeptides comprising minor changes as compared to the above amino acid sequences without largely affecting the tertiary structure and the function thereof are also within the scope of the present disclosure. Thus, also encompassed by the present disclosure is a population of polypeptide variants based on a common scaffold, wherein each polypeptide in the population comprises an amino acid sequence with 91% or greater identity to a sequence as defined in i). In some embodiments, each polypeptide may comprise a sequence which is at least 93%, such as at least 95%, such as at least 97% identical to the sequence as defined in i).

The population defined herein consists of a large number of unique and different variants of the defined polypeptide molecules. In this context, a large number may for example mean that the population comprises at least $1 \times 10^4$ unique polypeptide molecules, or at least $1 \times 10^6$, at least $1 \times 10^8$, at least $1 \times 10^{10}$, at least $1 \times 10^{12}$, or at least $1 \times 10^{14}$ unique polypeptide molecules. As the skilled person will appreciate, it is necessary to use a group that is large enough to provide the desired size of the population. The "population" described herein may also be denoted "library".

The skilled person will appreciate that the population as disclosed herein may be useful as a library for selection of new binding molecules based on the polypeptide defined in i). It is well known in the art that binding molecules may be isolated from a population (or library) of randomized polypeptides. This technology is described in general terms in PCT publication WO95/19374, in Nord et al (1997) Nature Biotechnology 15:772-777 and in WO2009/080811, and has been successfully applied in order to select binding molecules based on a common Z domain scaffold against a variety of target molecules through the random variation of thirteen different target binding positions and subsequent selection of binders of interest in a phage display or other selection system based on genotype-phenotype coupling. The population as disclosed herein is a population of polypeptide variants which exhibit improved properties, in particular in terms of stability, compared to populations in the prior art. Examples of Z variants isolated from a population (or library) of randomized polypeptides include Z variants with affinity for the EGF receptor (disclosed in WO2007/065635), for the HER2 receptor (disclosed in WO2009/080810), for the HER3 receptor (disclosed in WO2010/056124), for the IGF1 receptor (disclosed in WO2010/019117), for the PDGF receptor β (disclosed in WO2009/077175), for ABD (disclosed in WO2014/064237), for the neonatal Fc receptor (FcRn) (disclosed in PCT/EP2014/055299) and for carbonic anhydrase IX (disclosed in WO2014/096163).

In a fourth aspect of the present disclosure, there is provided a population of polynucleotides. Each polynucleotide in this population encodes a member of a population of polypeptides as defined above in connection with the third aspect.

In a fifth aspect of the present disclosure, there is provided a combination of a polypeptide population according to the third aspect and a polynucleotide population according to the fourth, in which combination each member of the polypeptide population is physically or spatially associated with a corresponding polynucleotide encoding that member via means for genotype-phenotype coupling. This physical or spatial association will be more or less strict, depending on the system used.

The means for genotype-phenotype coupling may comprise a phage display system. Phage display systems are well-known to the skilled person, and are, for example, described in Smith G P (1985) Science 228:1315-1317 and Barbas C F et al (1991) Proc Natl Acad Sci USA 88:7978-7982.

Furthermore, the means for genotype-phenotype coupling may comprise a cell surface display system. The cell surface display system may comprise prokaryotic cells, such as Gram-positive cells, or eukaryotic cells, such as yeast cells. Cell surface display systems are well-known to the skilled person. Prokaryotic systems are, for example, described in Francisco J A et al (1993) Proc Natl Acad Sci USA 90:10444-10448 and Lee S Y et al (2003) Trends Biotechnol 21:45-52. Eukaryotic systems are, for example, described in Boder E T et al (1997) Nat Biotechnol 15:553-557 and Gai S A et al (2007) Curr Opin Struct Biol 17:467-473. In one embodiment, said genotype-phenotype coupling may comprise a phage display system.

Furthermore, the means for genotype-phenotype coupling may comprise a cell free display system. The cell free display system may comprise a ribosome display system, or an in vitro compartmentalization display system, or a system for cis display, or a microbead display system. Ribosome display systems are well-known to the skilled person, and are, for example, described in Mattheakis L C et al (1994) Proc Natl Acad Sci USA 91:9022-9026 and Zahnd C et al (2007) Nat Methods 4:269-279. In vitro compartmentalization systems are well-known to the skilled person, and are, for example, described in Sepp A et al (2002) FEBS Lett 532:455-458. Cis display systems are well-known to the skilled person, and are, for example, described in Odegrip R et al (2004) Proc Natl Acad Sci USA 101:2806-2810. Microbead display systems are well-known to the skilled person, and are, for example, described in Nord O et al (2003) J Biotechnol 106:1-13.

Furthermore, the means for genotype-phenotype coupling may comprise a non-display system such as the protein-fragment complementation assay (PCA). PCA systems are well-known to the skilled person, and are, for example, described in Koch H et al (2006) J Mol Biol 357:427-441.

In a sixth aspect of the present disclosure, there is provided a method for selecting a desired polypeptide having an affinity for a predetermined target from a population of polypeptides, comprising the steps:
 (a) providing a population of polypeptides according to the third aspect;
 (b) bringing the population of polypeptides into contact with the predetermined target under conditions that enable specific interaction between the target and at least one desired polypeptide having an affinity for the target; and
 (c) selecting, on the basis of said specific interaction, the at least one desired polypeptide from the remaining population of polypeptides.

Below, this method is called the "selection method" according to the disclosure.

Step (a) may comprise the preparatory steps of providing a population of polynucleotides and expressing said population of polynucleotides to yield said population of polypeptides. The means for yielding a population of polypeptides varies depending on the display system used and examples of such means may be found in the genotype-phenotype references above. Each member of said population of polypeptides used in the selection method may physically be associated with the polynucleotide encoding that member via means for genotype-phenotype coupling. The means for genotype-phenotype coupling may be one of those discussed above.

Step (b) comprises the steps of bringing the population of polypeptides into contact with the predetermined target under conditions that enable specific interaction between the target and at least one desired polypeptide having an affinity for the target. The range of conditions applicable is determined by the robustness of the target, the robustness of the display system, and by the desired properties of the interaction with the target. For example a specific method of separating the interaction such as acidification to a predetermined pH may be desired. The skilled person knows what experiments are required to determine suitable conditions.

Step (c) comprises the selection of at least one polypeptide. The means for selection of desired polypeptide from the remaining population, based on the specific interaction between the predetermined target and at least one desired polypeptide having affinity for the target varies depending on the display system used and may be found in the genotype-phenotype references above. For example, the in vitro display selection systems are cell free in contrast to systems such as phage display and the protein fragment compartmentalization assay.

In an seventh aspect of the present disclosure, there is provided a method for isolating a polynucleotide encoding a desired polypeptide having an affinity for a predetermined target, comprising the steps:
 selecting said desired polypeptide and the polynucleotide encoding it from a population of polypeptides using the selection method according to the sixth aspect; and
 isolating the thus separated polynucleotide encoding the desired polypeptide.

Below, this method is called the "isolation method" according to the disclosure.

The separation of the polynucleotide from the polypeptide may be done differently depending on the display system used for selection. For example, in the cell free display systems such as cis display and ribosome display the polynucleotide or the corresponding mRNA is retrieved through efficient elution from the polypeptide using means described in the genotype-phenotype references above.

The isolation of the polynucleotide may be done by different methods depending on the display system used for selection. In most of the above described selection systems, for example the protein fragment complementation assay, the polynucleotide can be directly isolated by specific PCR amplification using appropriate oligonucleotides. Also, as in ribosome display, the polynucleotide can be isolated from the corresponding mRNA using reverse transcription. The various means for isolation of the polynucleotide may be found in the genotype-phenotype references above.

In an eighth aspect of the present disclosure, there is provided a method for identifying a desired polypeptide having an affinity for a predetermined target, comprising the steps:
  isolating a polynucleotide encoding said desired polypeptide using the isolation method according to the seventh aspect; and
  sequencing the polynucleotide to establish by deduction the amino acid sequence of said desired polypeptide.

The sequencing of the polynucleotide may be done according to standard procedures well-known to the skilled person.

In a ninth aspect of the present disclosure, there is provided a method for selecting and identifying a desired polypeptide having an affinity for a predetermined target from a population of polypeptides, comprising the steps:
  (a) synthesizing each member of a population of polypeptides according to the third aspect on a separate carrier or bead;
  (b) selecting or enriching the carriers or beads based on the interaction of the polypeptide with the predetermined target; and
  (c) identifying the polypeptide by protein characterization methodology.

In step (c), it is for example possible to use mass spectrometric analysis.

Below, this method is called the "selection and identification method" according to the disclosure.

In a tenth aspect of the present disclosure, there is provided a method for production of a desired polypeptide having an affinity for a predetermined target, comprising the steps:
  selecting and identifying a desired polypeptide using the selection method according to the sixth aspect or the selection and identification method according to the ninth aspect; and
  producing said desired polypeptide.

Below, this method is called the "production method" according to the disclosure.

In the production method, production may be carried out using recombinant expression of a polynucleotide encoding the desired polypeptide. The production may also be carried out using chemical synthesis of the desired polypeptide de novo.

In an eleventh aspect of the present disclosure there is provided a method for production of a desired polypeptide having an affinity for a predetermined target, comprising the steps:
  (a1) isolating a polynucleotide encoding said desired polypeptide using the isolation method according to the seventh aspect; or
  (a2) backtranslating a polypeptide identified using the selection and identification method according to the ninth aspect; and
  (b) expressing the thus isolated polynucleotide to produce said desired polypeptide,
  wherein step (b) is performed either after step (a1) or step (a2).

The polypeptides, populations and methods according to the disclosure enable the provision of agents with an affinity for a predetermined target, through the provision of a polypeptide that is characterized by specific binding to the predetermined target.

It is also possible to provide polypeptides binding to a predetermined target that exhibit little or no non-specific binding.

It is also possible to provide polypeptides binding to a predetermined target that can readily be used as a moiety in a fusion polypeptide.

Furthermore, it is possible to provide polypeptides binding to a predetermined target that solve one or more of the known problems experienced with existing antibody reagents.

Moreover, it is possible to provide polypeptides binding to a predetermined target that are amenable to use in therapeutic and/or diagnostic applications.

It is also possible to provide polypeptides binding to a predetermined target that are easily made by chemical peptide synthesis.

Furthermore, the invention enables the identification of polypeptides binding to a predetermined target that exhibit an improved stability vis-à-vis known agents binding to the same target.

It is also possible to provide polypeptides binding to a predetermined target that exhibit low antigenicity when used in vivo in a mammal and/or that exhibit an improved biodistribution upon administration to a mammal.

The modifications discussed above for the polypeptides constituting the population according to the present disclosure are also applicable to the polypeptides obtained by any of the above mentioned methods.

Polypeptides according to the present disclosure may be produced by any known means, including chemical synthesis or expression in different prokaryotic or eukaryotic hosts, including bacterial cells, yeast cells, plant cells, insect cells, whole plants and transgenic animals.

While the polypeptides, populations of polypeptides and methods for identification, selection, isolation and production disclosed herein have been described with reference to various exemplary aspects and embodiments, it will be understood by those skilled in the art that various changes may be made and equivalents may be substituted for elements thereof without departing from the scope of the invention. In addition, many modifications may be made to adapt a particular situation or molecule to the teachings of the invention without departing from the essential scope thereof. Therefore, it is intended that the disclosure not be limited to any particular embodiment contemplated, but to include all embodiments falling within the scope of the appended claims.

BRIEF DESCRIPTION OF THE FIGURES

FIG. 1A-C is a listing of the amino acid sequences of examples of a polypeptide as disclosed herein. Sequences of C5 binding Z variant polypeptides shown in Examples 2-3 to have improved stability are listed in FIG. 1A-C as SEQ ID NO:12, 17, 18 and 22, and the sequences thereof corresponding to the shortest sequence defined herein are listed as SEQ ID NO:19-21. The amino acid sequences of C5 binding polypeptides fused to albumin binding domains are in FIG. 1A-C with sequence identifiers SEQ ID NO:4-11, 13-16 and 23-25. Sequences of Z variant polypeptides with affinity for HER2, PDGF-Rβ, FcRn and CAIX shown in Example 12 to have improved stability are listed as SEQ ID NO:28-29, SEQ ID NO:31-32, SEQ ID NO:34-35 and SEQ ID NO:37-42, respectively, together with the corresponding control polypeptides SEQ ID NO:27, 30, 33 and 36. The sequences of said Z variant polypeptides with affinity for HER2, PDGF-Rβ, FcRn and CAIX corresponding to the shortest sequence defined herein are listed as SEQ ID NO:43-54. Additionally, the amino acid sequences of a control C5 binding polypeptide, the control C5 binding polypeptide fused to albumin, the albumin binding domain and of human C5 are listed as SEQ ID NO:26, 1, 2 and 3, respectively.

EXAMPLES

The following Examples disclose novel Z variant polypeptides exhibiting improved stability. Herein, the properties of Z variant polypeptides based on previous generations of scaffolds were compared with Z variant polypeptides based on the scaffold disclosed herein.

Comparative Example 1

Stability Test of Known C5 Binding Z Variant

A C5 binding Z variant designated PSI0242 (SEQ ID NO:1) was formulated in 25 mM NaP/125 mM NaCl pH 7.0 and subjected to an accelerated stability study for 2 weeks at 37° C. The stability was measured by the appearance of new variants after the stability testing by SDS-PAGE and Reversed Phase HPLC (RPC). In both analyses, the initial sample and the one subjected to the stability study were run in parallel. For the SDS-PAGE, 7.5 µg protein was loaded into each well. The RPC was run on an Agilent 1100 HPLC using a Mobile Phase A consisting of 0.1% trifluoroacetic acid (TFA) in water, and a Mobile Phase B consisting of 0.1% TFA/45% MeOH/45% isopropylamine (IPA)/10% water.

Figure 2:
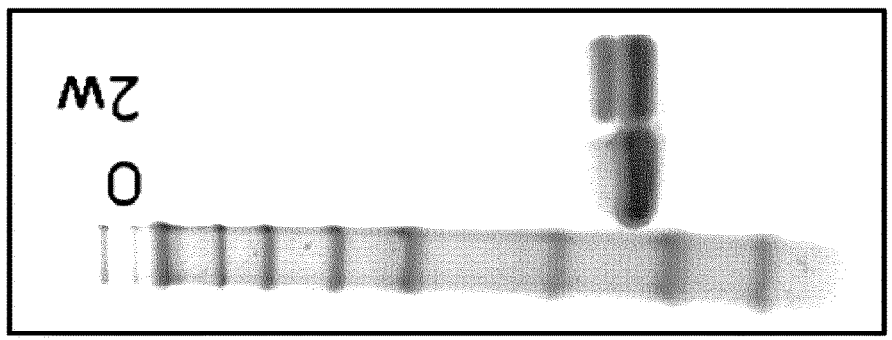
FIG. 2 is an image of a SDS-PAGE gel wherein the first lane contains SeeBlue 2P size marker and the bands represent the C5 binding polypeptide PSI0242 (SEQ ID NO:1) (0) prior to stability test; and (2 w) after a 2 week stability test.
Figure 3:
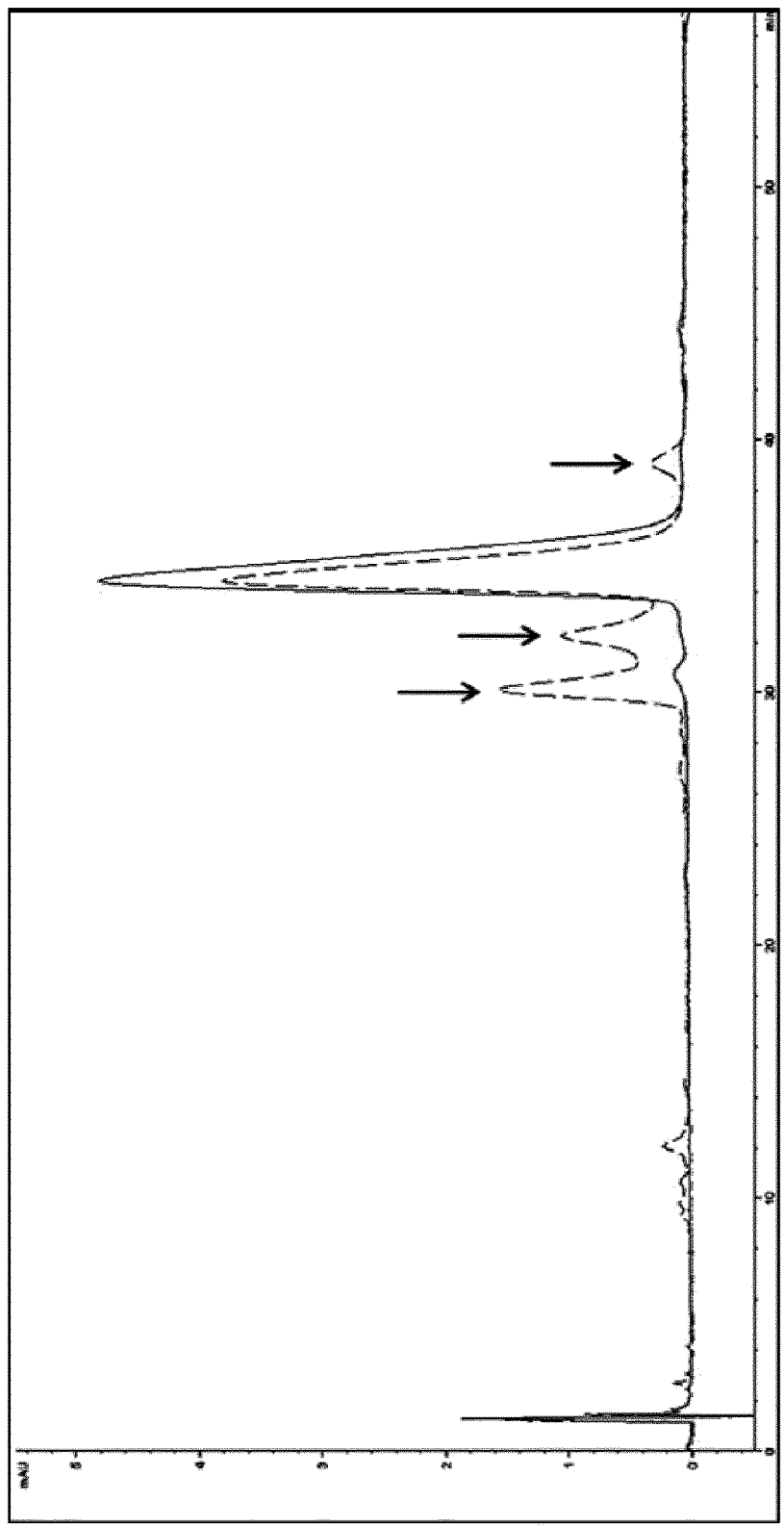
FIG. 3 is a chromatogram from reversed phase HPLC of PSI0242 (SEQ ID NO:1) prior to stability test (solid line) and after a 2 week stability test (dotted line).

The results show that new forms of the protein were formed during incubation, visualized as bands in SDS-PAGE (FIG. 2) and as new peaks in Reversed Phase HPLC (RPC) chromatograms (FIG. 3). In FIG. 3, the main peak after incubation for 2 weeks corresponds to 57% of the original protein sample.

Positions 1-60 in SEQ ID NO:1 correspond to the polypeptide Z06175a, previously disclosed in WO2013/126006 as SEQ ID NO:753.

Example 2

Stability Test of Modified C5 Binding Polypeptides and Compounds

Modified C5 binding polypeptides and compounds were synthesized and purified essentially as described in WO2013/126006.

Briefly, DNA encoding C5 binding Z variants were E. coli codon optimized and synthesized by GeneArt, GmbH. The synthetic genes representing the new C5 binding Z variants were subcloned and expressed in E. coli.

Intracellularly expressed Z variants were purified using conventional chromatography methods. Homogenization and clarification was performed by sonication followed by centrifugation and filtration. Anion exchange chromatography was used as capture step. Further purification was obtained by hydrophobic interaction chromatography. The purifications were executed at acidic conditions (pH 5.5). Polishing and buffer exchange was performed by size exclusion chromatography.

Figure 4:
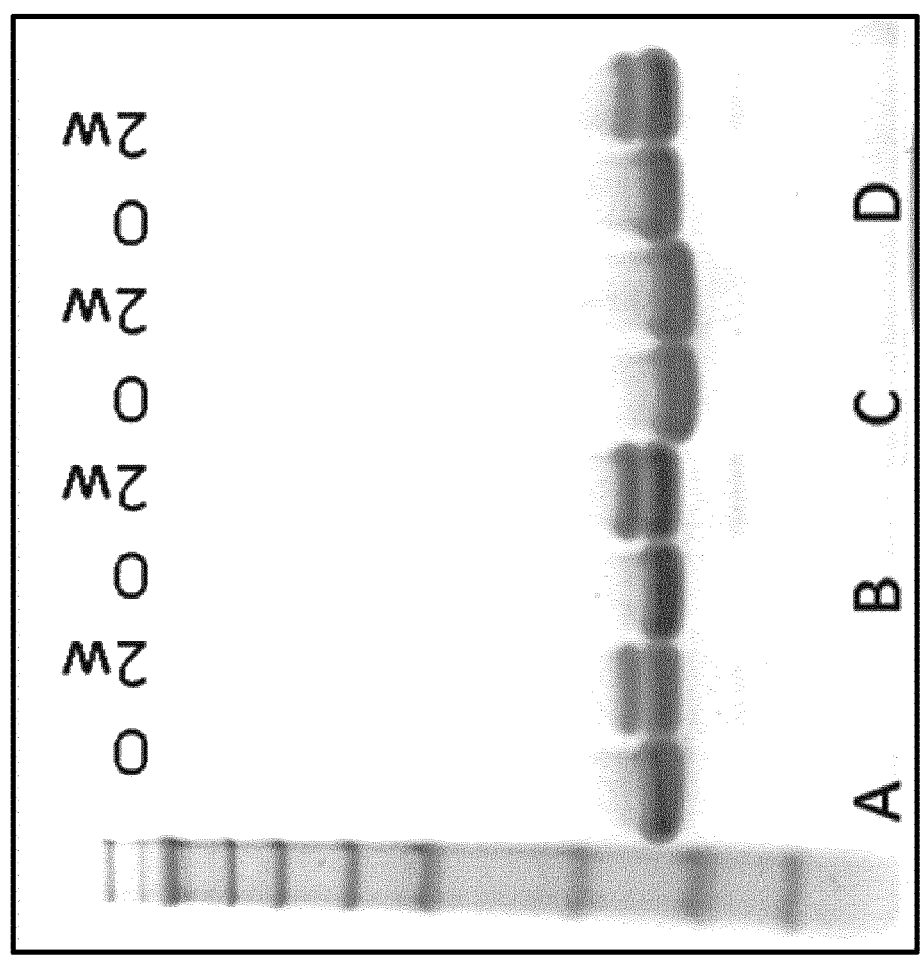
FIG. 4 is an image of a SDS-PAGE gel wherein the first lane contains SeeBlue 2P size marker and the bands represent (0) the initial samples; and (2 w) the samples after a 2 week stability test. A: SEQ ID NO:1; B: SEQ ID NO:13; C: SEQ ID NO:14; D: SEQ ID NO:16.

The purified proteins were formulated in 25 mM NaP/125 mM NaCl pH 7.0 and subjected to an accelerated stability study for 2 weeks at 37° C. The stability was measured by the appearance of new variants after the stability testing by SDS-PAGE and Reversed Phase HPLC (RPC). In both analyses, the initial sample and the one subjected to the stability study were run in parallel. For the SDS-PAGE, 7.5 µg protein was loaded into each well. An example of a resulting gel is shown in FIG. 4.

Figure 5:
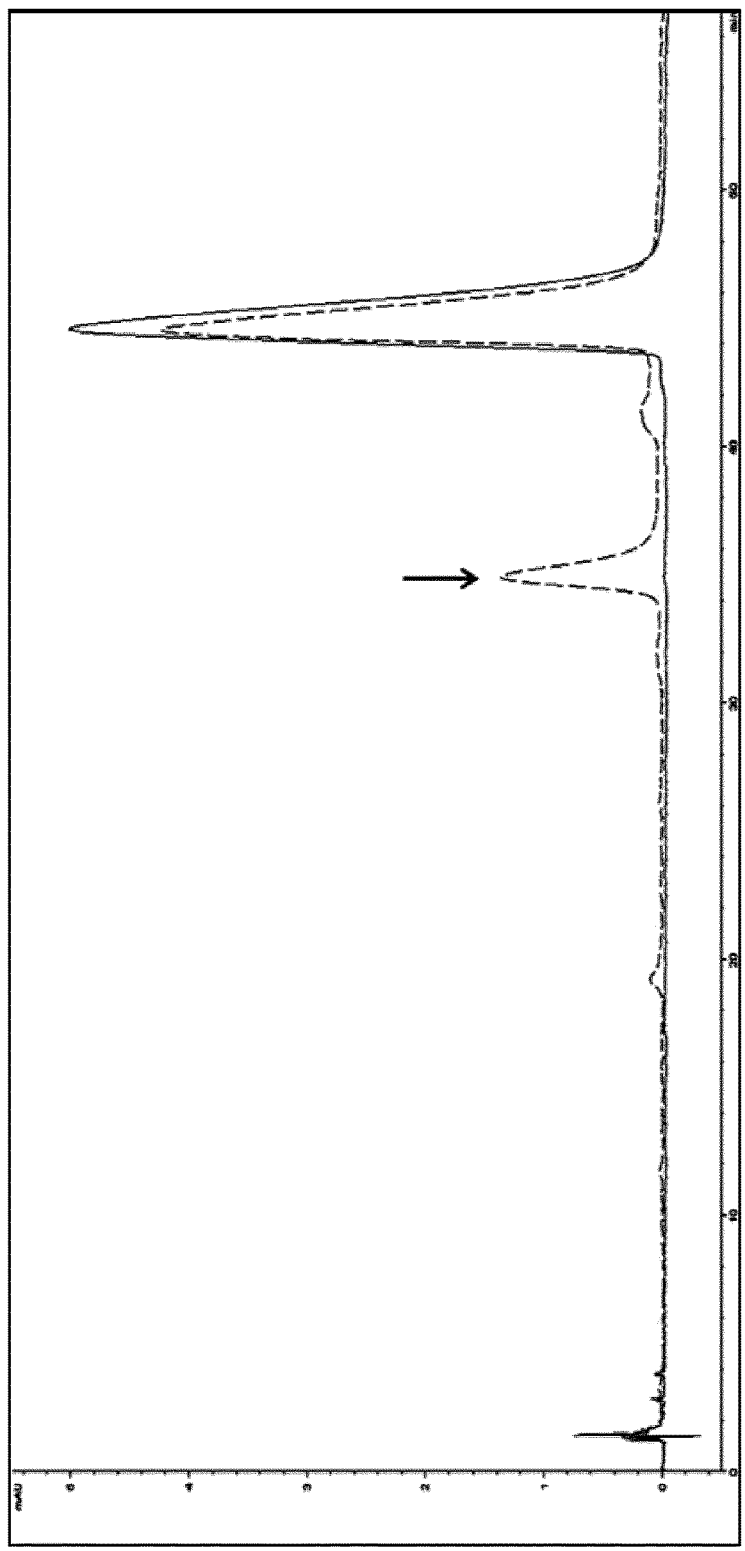
FIG. 5 is a chromatogram from reversed phase HPLC of a modified C5 inhibitor (SEQ ID NO:5) prior to stability test (solid line) and after a 2 week stability test (dotted line).
Figure 6:
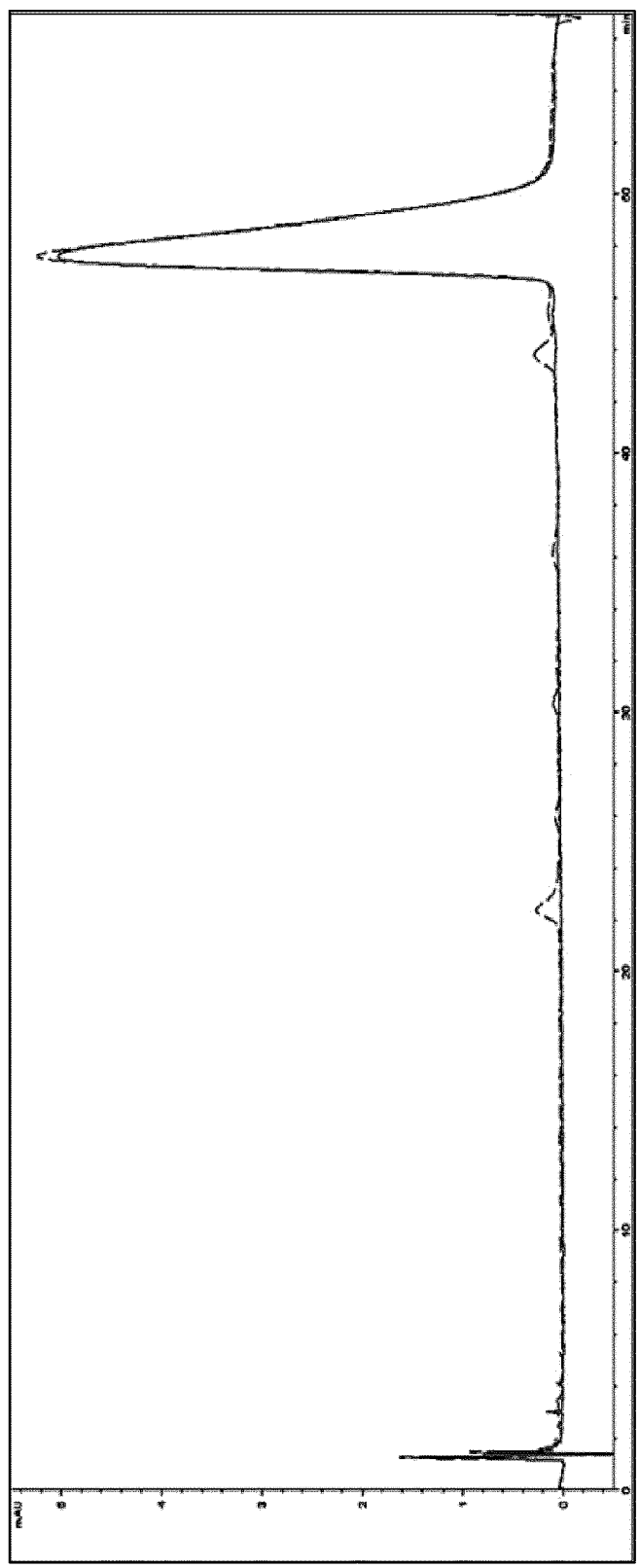
FIG. 6 is a chromatogram from reversed phase HPLC of a modified C5 inhibitor (SEQ ID NO:16) prior to stability test (solid line) and after a 2 week stability test (dotted line).
Figures 7A, 7B:
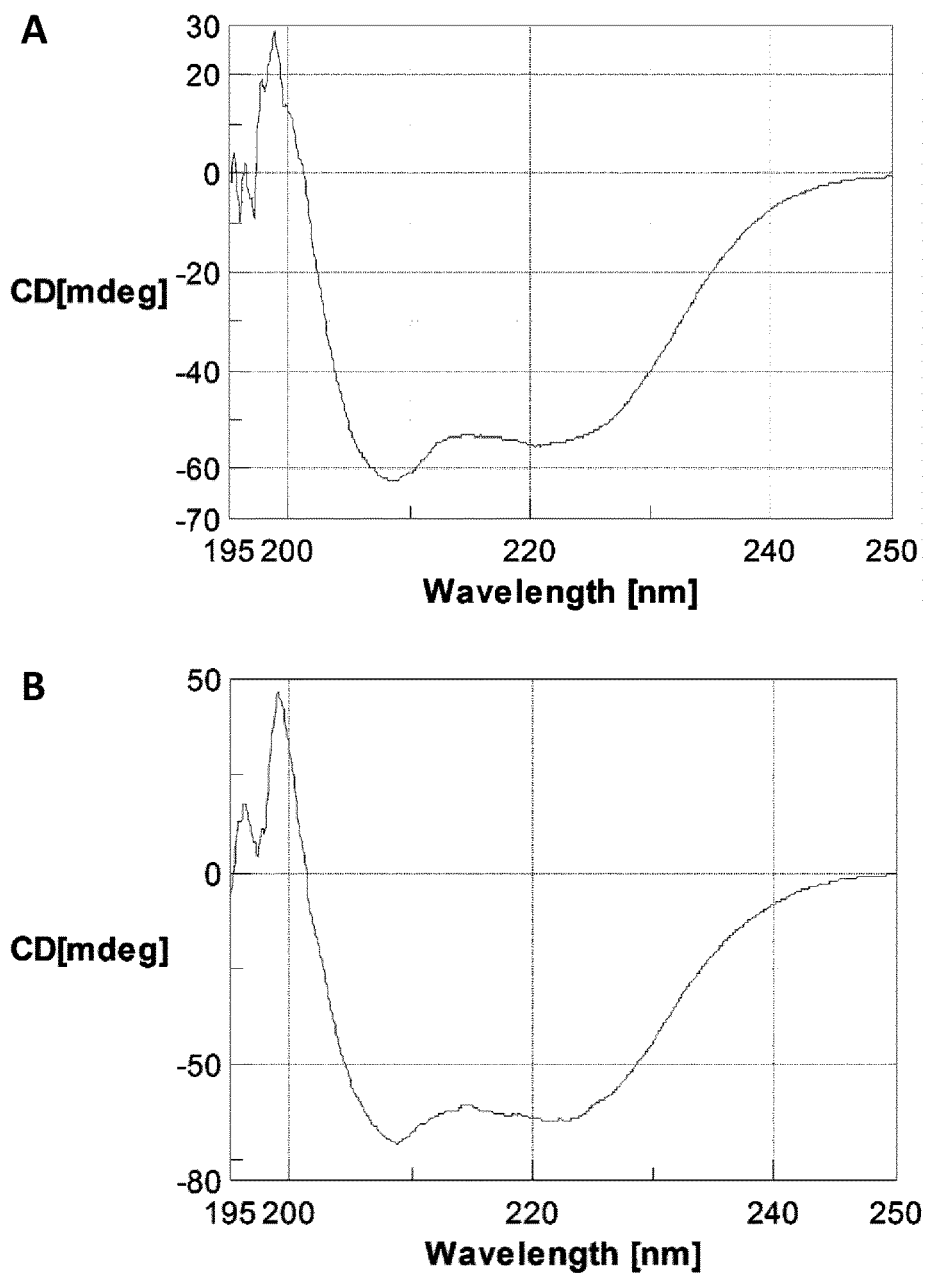
FIG. 7A-G are CD spectra collected for A: Z17351 (SEQ ID NO:37); B: Z17352 (SEQ ID NO:38); C: Z17355 (SEQ ID NO:39); D: Z17357 (SEQ ID NO:40); E: Z17359 (SEQ ID NO:41); F: Z17360 (SEQ ID NO:42); and G: Z09782 (SEQ ID NO:36).
Figures 7C, 7D:
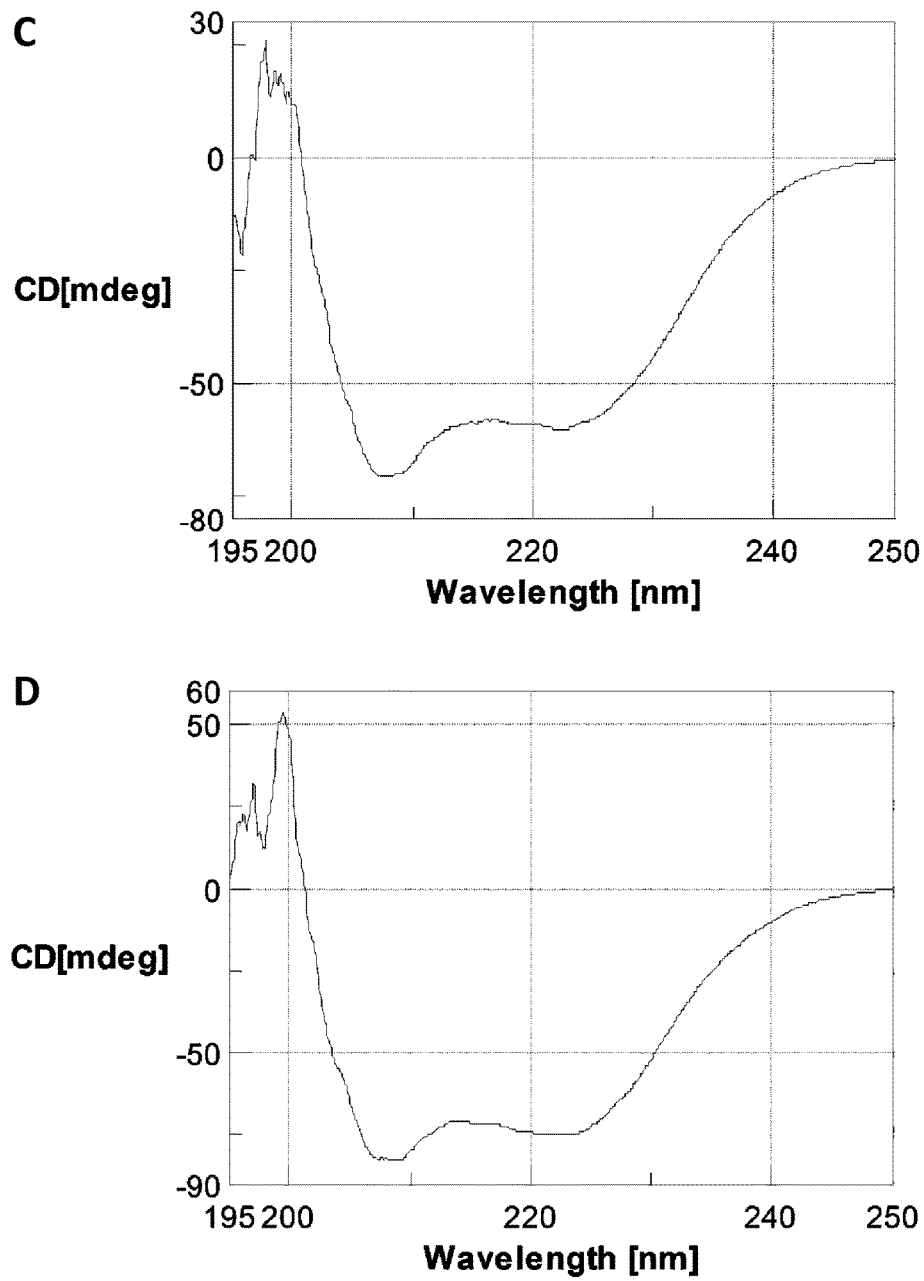
Figures 7E, 7F:
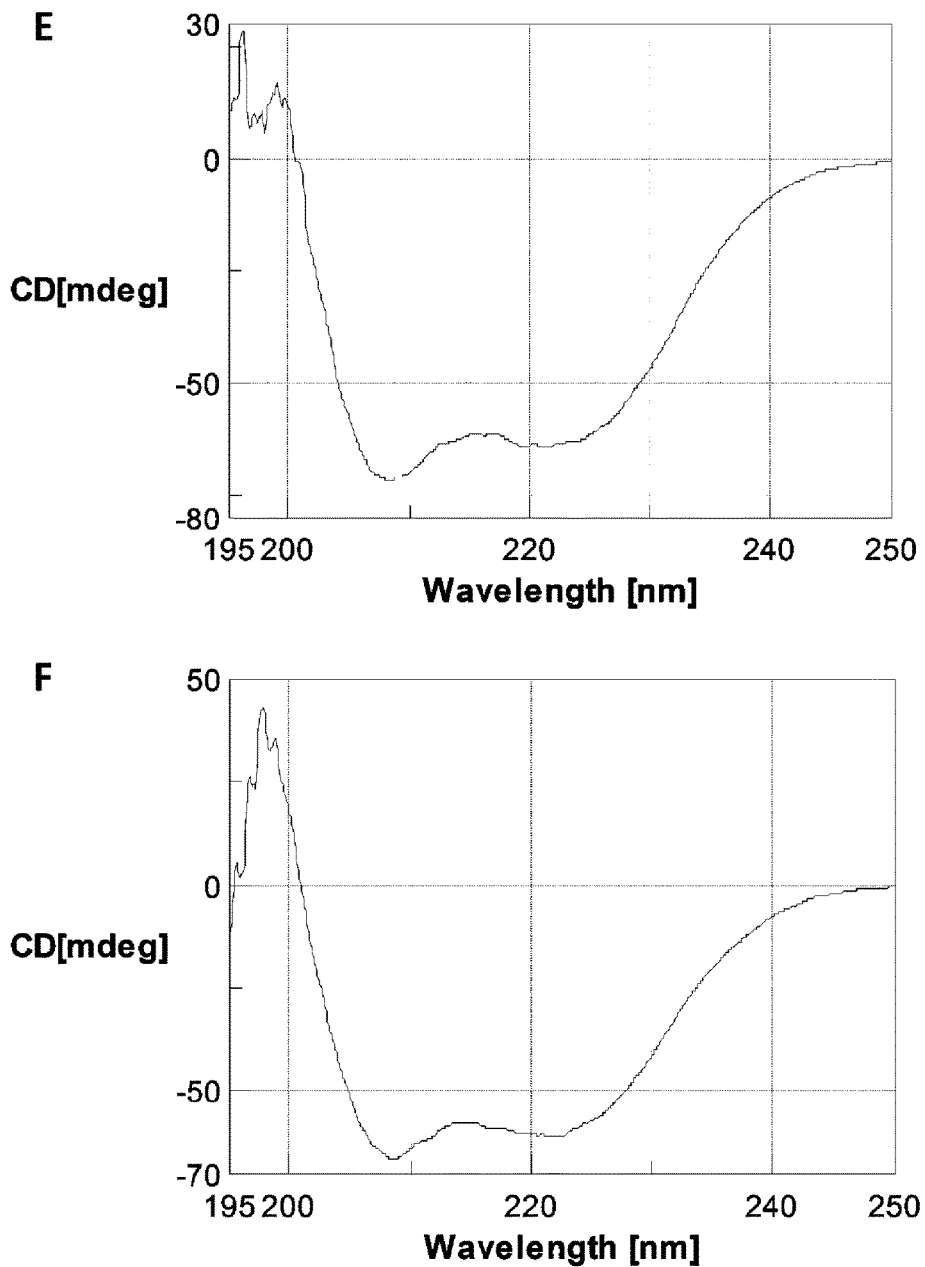
Figure 7G:
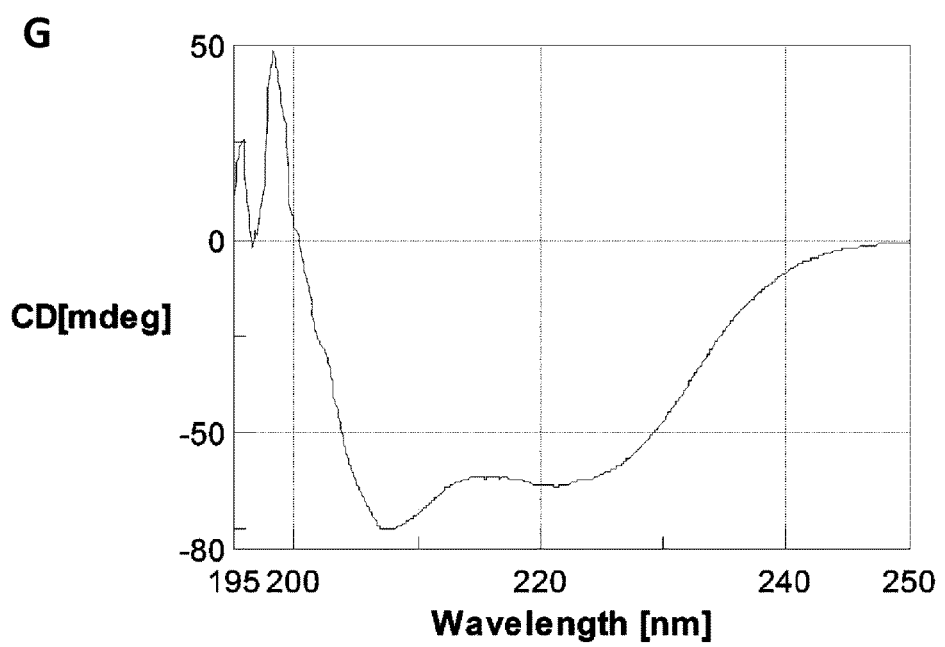
Figure 8A:
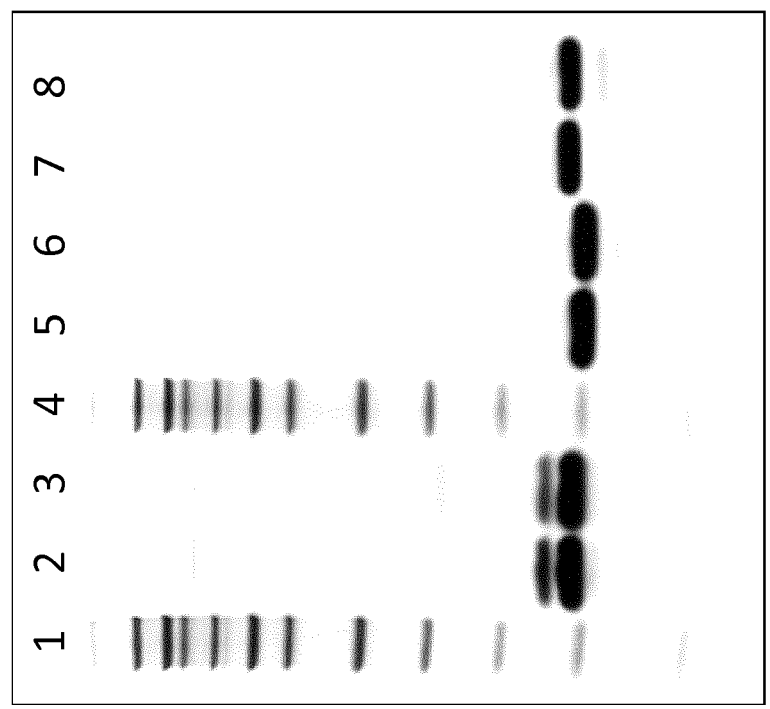
FIG. 8A-D are images of SDS-PAGE gels showing original and inventive polypeptides before (0) and after a 2 week (2 w) stability test. A: Polypeptides targeting HER2: lane 1: Mw, lane 2: Z02891 (0), lane 3: Z02891 (2 w), lane 4: Mw, lane 5: Z17341 (0), lane 6: Z17341 (2 w), lane 7: Z17342 (0), lane 8: Z17342 (2 w); B: Polypeptides targeting PDGF-Rβ: lane 1: Mw, lane 2: Z15805 (0), lane 3: Z15805 (2 w), lane 4: Mw, lane 5: Z17343 (0), lane 6: Z17343 (2 w), lane 7: Z17344 (0), lane 8: Z17344 (2 w); C: Polypeptides targeting FcRn: lane 1: Z10103 (0), lane 2: Z10103 (2 w), lane 3: Mw, lane 4: Z17347 (0), lane 5: Z17347 (2 w), lane 6: Z17348 (0), lane 7: Z17348 (2 w); and D: Polypeptides targeting CAIX: lane 1: Mw, lane 2: Z09782 (0), lane 3: Z09782 (2 w), lane 4: Mw, lane 5: Z17351 (0), lane 6: Z17351 (2 w), lane 7: Z17352 (0), lane 8: Z17352 (2 w); lane 9: Z17355 (0), lane 10: Z17355 (2 w), lane 11: Z17357 (0), lane 12: Z17357 (2 w), lane 13: Z17359 (0), lane 14: Z17359 (2 w), lane 15: Z17360 (0), lane 16: Z17360 (2 w). The molecular size marker (Mw) was NOVEX Sharp Pre-stained Protein Standard (216, 160, 110, 80, 60, 50, 40, 30, 20, 15, 10, 3.5 kDa). (The diagonal bands seen in FIG. 8C are an artifact resulting from an imprint from a second gel stained in the same container).
Figure 8B:
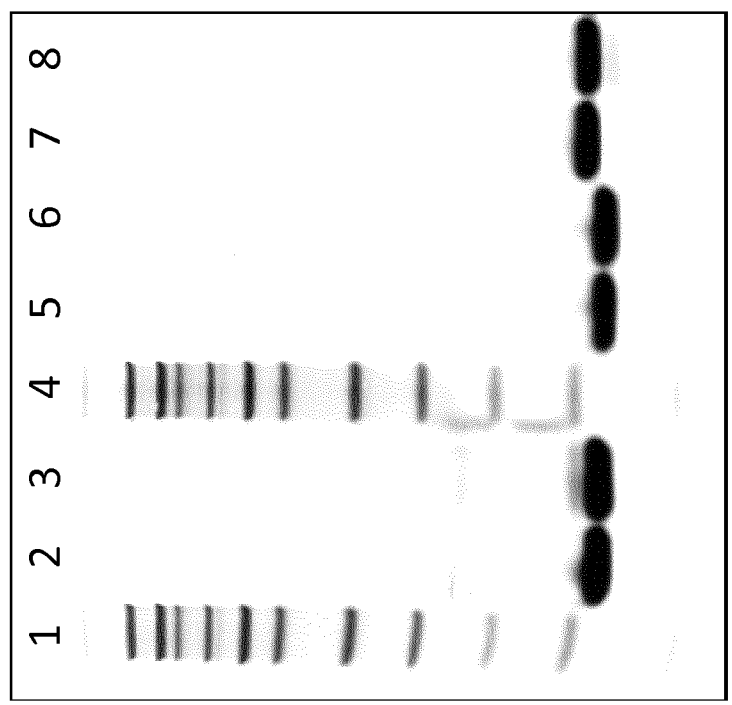
Figure 8C:
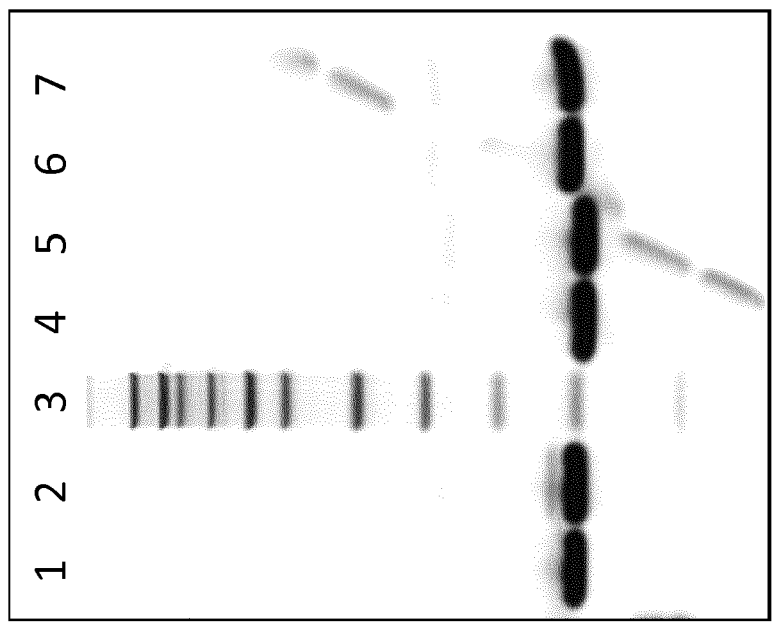
Figure 8D:
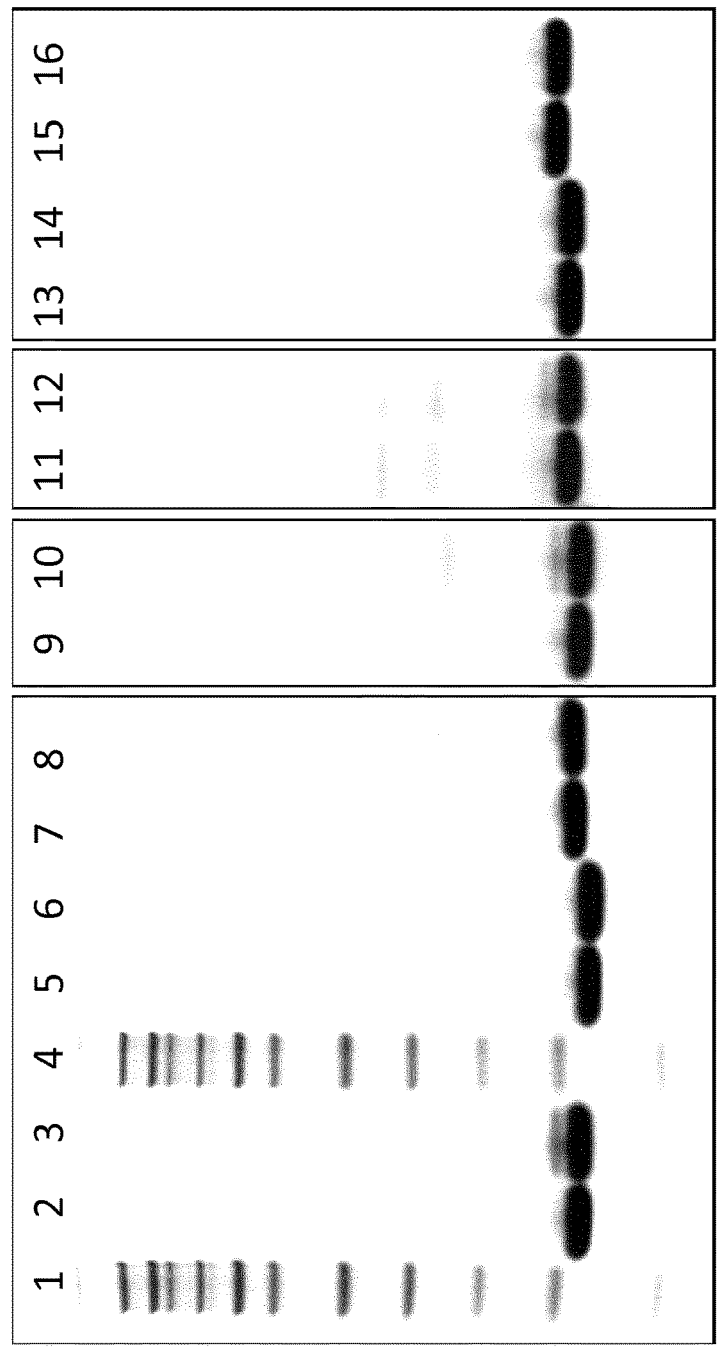
Figure 9A:
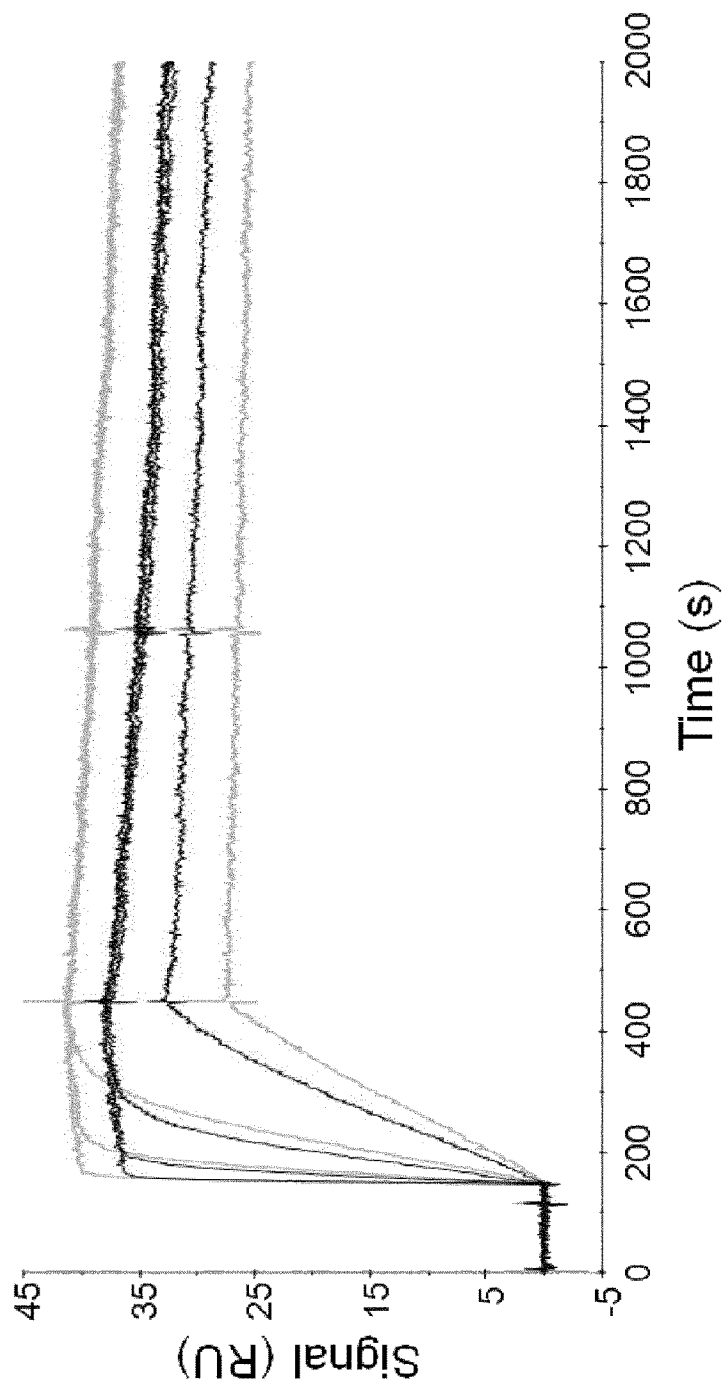
FIG. 9A-D shows sensorgrams of binding of Z variants comprising the amino acid substitutions ND to SE in position 52-53 (black) and original Z variants (gray) with affinity for the same target after a 2 week stability test. A: Binding of Z017341 (SEQ ID NO:28) and Z02891 (SEQ ID NO:27) to HER2; B: Binding of Z017343 (SEQ ID NO:31) and Z15805 (SEQ ID NO:30) to PDGF-Rβ; C: Binding of Z017347 (SEQ ID NO:34) and Z10130 (SEQ ID NO:33) to FcRn and D: Binding of Z017351 (SEQ ID NO:37) and Z09782 (SEQ ID NO:36) to CAIX. The injected concentrations of each Z variant were as described in Example 13.
Figure 9B:
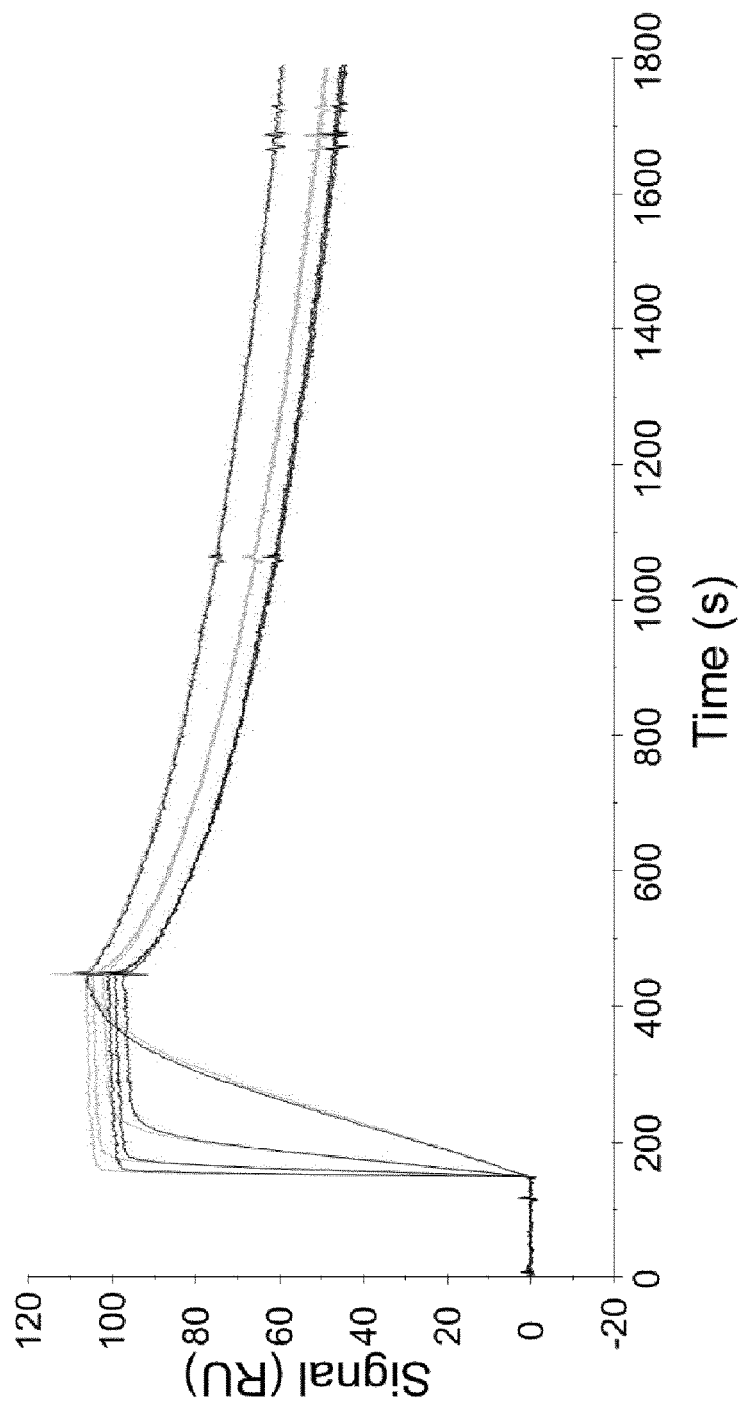
Figure 9C:
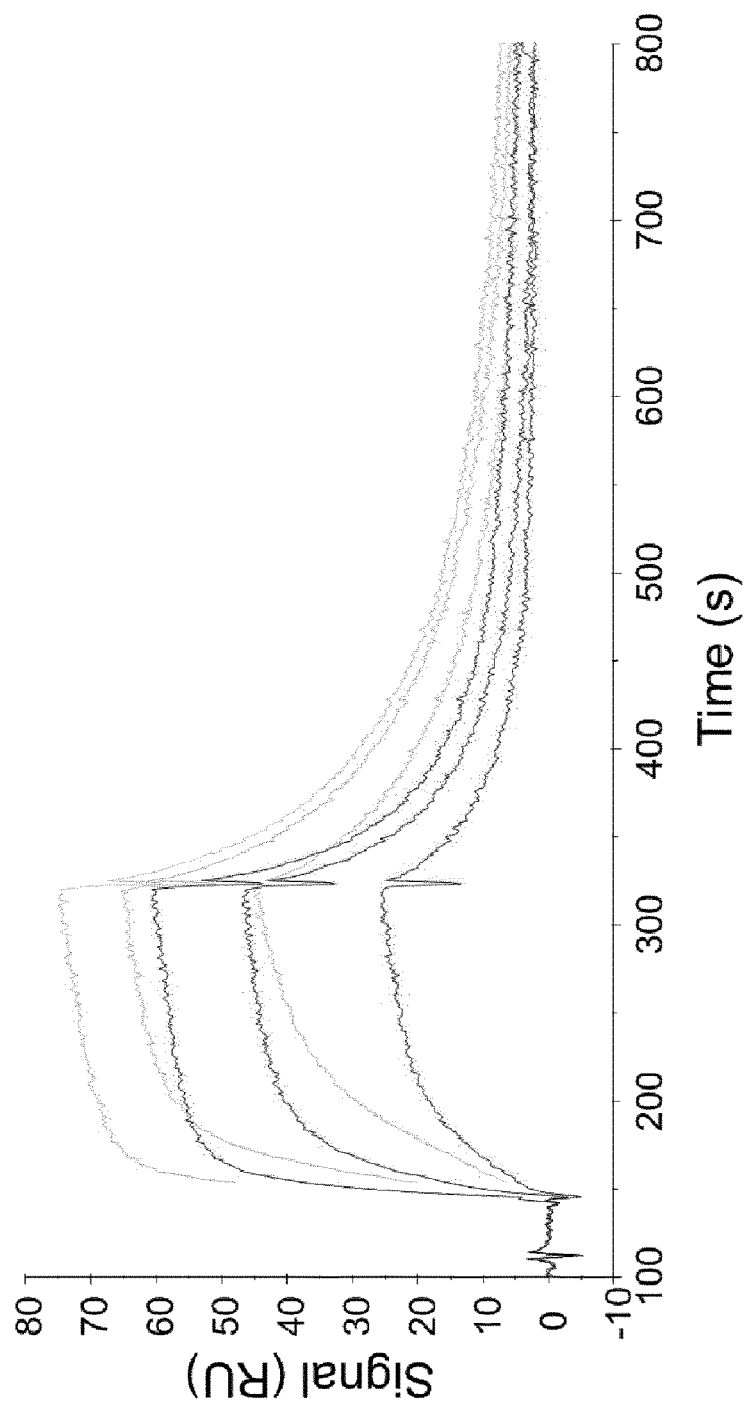
Figure 9D:
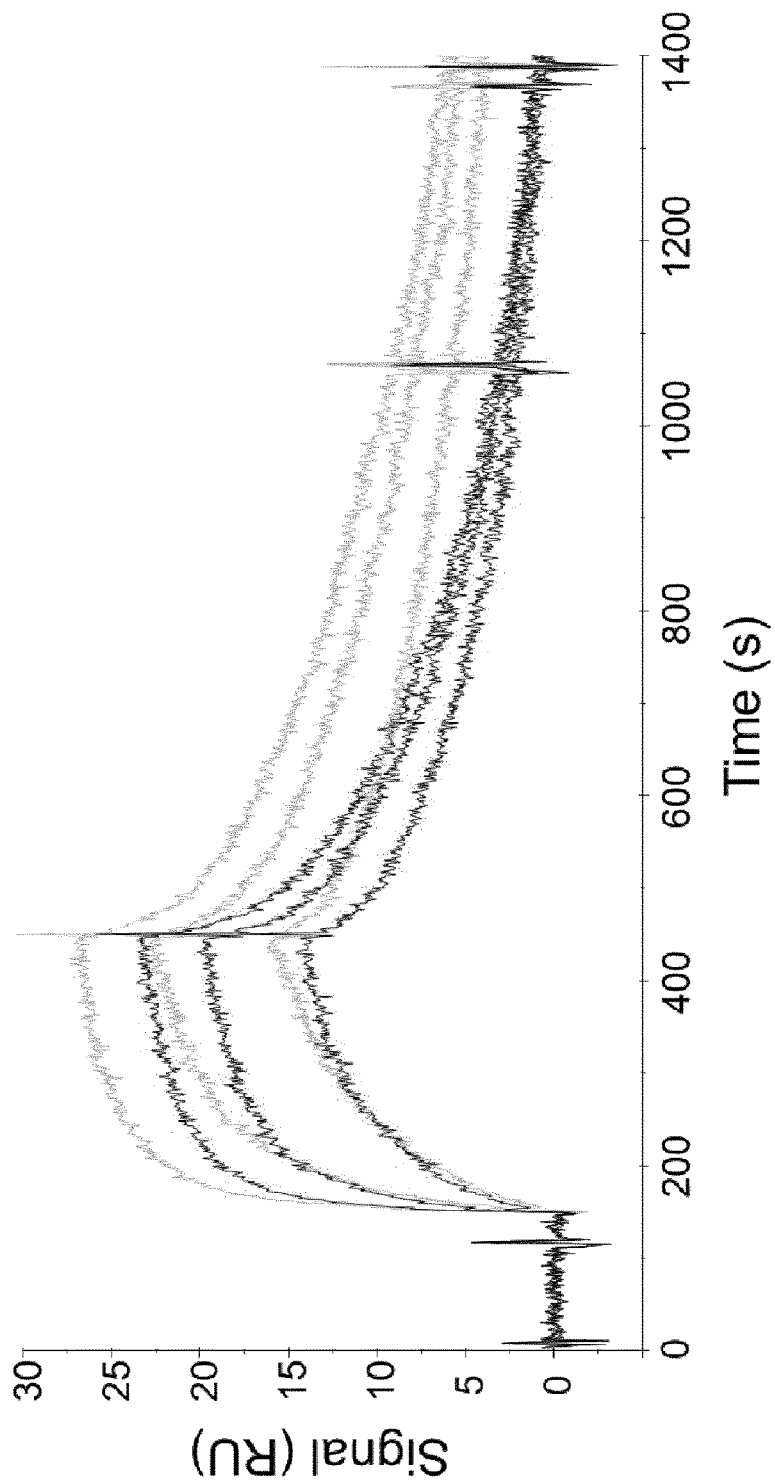

The RPC was run on an Agilent 1100 HPLC using a Mobile Phase A consisting of 0.1% trifluoroacetic acid (TFA) in water, and a Mobile Phase B consisting of 0.1% TFA/45% MeOH/45% isopropylamine (IPA)/10% water. An example of a resulting chromatogram for SEQ ID NO:5 is shown in FIG. 5.

The results of the stability testing are summarized in Table 1.

TABLE 1

Stability of Z variant polypeptides after 2 weeks of incubation at 37° C. Results from SDS-PAGE and HPLC are compared.

| SEQ ID NO: | Designation | SDS-PAGE bands | RPC prepeaks | Main peak (% of total protein) | RPC postpeaks |
|---|---|---|---|---|---|
| 1 | PSI0242 | 2 | 2 | 57 | 1 |
| 4 | PSI0332 | 2 | 1 | 57 | 1 |
| 5 | PSI0334 | 1 | 1 | 73 | 0 |
| 6 | PSI0335 | 2 | 2 | 57 | 1 |
| 7 | PSI0336 | 2 | 2 | 57 | 1 |
| 8 | PSI0337 | 2 | 2 | 57 | 1 |
| 9 | PSI0339 | 2 | 2 | 57 | 1 |
| 10 | PSI0340 | 2 | 2 | 67 | 1 |
| 11 | PSI0369 | 2 | 1 | 90 | 1 |
| 12 | PSI0377 | 1 | 0 | 77 | 0 |
| 13 | PSI0378 | 1 | 0 | 89 | 0 |
| 14 | PSI0379 | 1 | 0 | 88 | 0 |
| 15 | PSI0381 | 1 | 0 | 87 | 0 |
| 16 | PSI0383 | 1 | 0 | 91 | 0 |
| 22 | PSI0400 | 1 | 0 | 91 | 0 |
| 23 | PSI0410 | 1 | 1 | 72 | 1 |
| 24 | PSI0403 | 1 | 1 | 77 | 1 |
| 25 | PSI0404 | 1 | 1 | 88 | 0 |

It can be concluded from Table 1 that certain modified C5 binding polypeptides or compounds have improved properties, such as increased stability, when compared with PSI0242. Such improved C5 binding polypeptides or compounds include PSI0334 (SEQ ID NO:5), PSI0340 (SEQ ID NO:10), PSI0369 (SEQ ID NO:11), PSI0377 (SEQ ID NO:12), PSI0378 (SEQ ID NO:13), PSI0379 (SEQ ID NO:14), PSI0381 (SEQ ID NO:15), PSI0383 (SEQ ID NO:16), PSI0400 (SEQ ID NO:22), PSI0410 (SEQ ID NO:23), PSI0403 (SEQ ID NO:24) and PSI0404 (SEQ ID NO:25). Six of the mentioned variants (SEQ ID NO:5, 12, 13, 14, 16 and 22) have in common that the amino acid residues in positions 52-53 have been substituted from ND (cf. PSI0242) to SE. In SEQ ID NO:15, the corresponding substitution is from ND to ES. In SEQ ID NO:24 only the amino acid residue in position 53 has been substituted from D to E, while in SEQ ID NO:25 the amino acid residue in position 52 has been substituted from N to S.

Example 3

Binding of Modified Compounds to Human C5

Human serum albumin was immobilized to Amine Reactive 2$^{nd}$ generation (AR2G) Dip and Read Biosensors (Pall Life sciences (ForteBio) Cat #18-5092) by amine coupling. PSI0242 (SEQ ID NO:1; 1 µM) and modified C5 binding compounds (1 µM) in read buffer (HBS-EP Buffer [10 mM HEPES pH 7.4, 150 mM NaCl, 3 mM EDTA, 0.005% Surfactant P20], GE Healthcare, cat. no. BR100188) were loaded, each onto a separate sensor with HSA, for 120 seconds followed by a base line recording for 60 seconds in read buffer before being subjected to human C5 (Quidel, cat. no. A403) at concentrations ranging from 0.79 nM to 25 nM in read buffer with a regeneration cycle and a base line recording between each concentration. Regeneration conditions for the sensors were 10 mM Glycine, pH 2 (three pulses with 30 seconds and running buffer for 60 seconds). Each spectrogram was reference subtracted against that of an analogous construct containing an albumin binding domain (SEQ ID NO:2) but without the C5 binding capacity. The data were analyzed according to Langmuir 1:1 model using ForteBio Analysis 7.1 (Pall Life sciences (ForteBio) kinetics software).

The relative $K_D$ of the interaction of PSI0242 (SEQ ID NO; 1) with C5 is shown in Table 2. The $K_D$ of PSI0242 (SEQ ID NO:1) varied from 1-3 nM in different runs.

The results in Table 2 indicate that C5 binding compounds according to the present disclosure have a binding capacity to human C5 which is similar to that of the polypeptide PSI0242 (SEQ ID NO:1) disclosed in WO2013/126006.

TABLE 2

$K_D$ value of the interaction of SEQ ID NO: 5, 13, 15 and 16 with C5 compared to $K_D$ value of C5 interaction with SEQ ID NO: 1

| SEQ ID NO: | Designation | Rel. $K_D$ |
|---|---|---|
| 1 | PSI0242 | 1.0 |
| 5 | PSI0334 | 1.1 |
| 13 | PSI0378 | 1.3 |
| 15 | PSI0381 | 23 |
| 16 | PSI0383 | 2.1 |

Example 4

Stability of Chemically Synthesized C5 Binding Polypeptide

A chemically synthesized PSI0400 (SEQ ID NO:22) was ordered from BACHEM AG. The stability of the polypeptide was tested according to the same methodology as in Example 2. The results of the stability testing are shown in Table 3.

TABLE 3

Stability of the chemically produced C5 binding polypeptide PSI0400 (SEQ ID NO: 22) after 2 weeks of incubation

| SEQ ID NO | Designation | SDS-PAGE bands | RPC prepeaks | Main peak (% of total protein) | RPC postpeaks |
|---|---|---|---|---|---|
| 22 | PSI0400 | 1 | 0 | 91 | 0 |

The stability of PSI0400 was comparable to the same polypeptide produced in E. coli in Example 2.

The integrity of the fold of PSI0400 (SEQ ID NO:22) was compared to a recombinant C5 binding polypeptide (PSI0257, SEQ ID NO:26), produced in accordance with the methods of Example 2, using far UV circular dichroism (CD) spectra.

The CD spectra were recorded by a J-720 CD spectropolarimeter (Jasco, Japan). The samples were diluted to 0.17 mg/ml protein concentration using Pi buffer (5 mM Na—K—PO$_4$, pH 7.0). A CD spectrum of Pi buffer was firstly recorded, then spectra were recorded for each of the samples and lastly for the Pi buffer again. As the two buffer spectra coincide, the firstly recorded spectrum was used as the buffer spectrum. The buffer spectrum was smoothened using the Savitzky-Golay procedure with convolution width of 25. The other spectra were smoothened according to the same procedure with a convolution width of 15. The smoothened buffer spectrum was then subtracted from each of the other smoothened spectra. The CDNN program was used to estimate the secondary content of the proteins and the resulting estimations are presented in Table 4. The results showed that neither the two amino acid substitutions at position 52 and 53 nor the polypeptide production by chemical synthesis influence the secondary structure content of the chemically synthesized polypeptide. The integrity of the secondary structure content was compared to the recombinantly produced PSI0257 (SEQ ID NO:26).

TABLE 4

Comparison of secondary structure content for two C5 binding polypeptides as determined by CD

|  | SEQ ID NO: 26 | SEQ ID NO: 22 |
| --- | --- | --- |
| Helix | 63% | 69% |
| Antiparallel | 3% | 2% |
| Parallel | 3% | 3% |
| Beta-Turn | 13% | 12% |
| Rndm. Coil | 13% | 11% |

Example 5

Binding of Modified Z Variants and Polypeptides to Human C5

The binding affinity of the C5 binding compounds PSI0242 (SEQ ID NO:1), PSI0340 (SEQ ID NO:10), PSI0378 (SEQ ID NO:13), and PSI0410 (SEQ ID NO:23) and the C5 binding polypeptide PSI0400 (SEQ ID NO:22) for human C5 was analyzed using a Biacore T200 instrument (GE Healthcare). Human C5 (Quidel, cat. no. A403) was coupled to a CM5 sensor chip (900 RU) using amine coupling chemistry according to the manufacturer's protocol. The coupling was performed by injecting hC5 at a concentration of 7.5 µg/ml in 10 mM Na-acetate buffer pH 5 (GE Healthcare). The reference cell was treated with the same reagents but without injecting human C5. Binding of the C5 polypeptide and compounds to immobilized hC5 was studied with the single cycle kinetics method, in which five concentrations of sample, typically 25, 12.5, 6.25, 3.12 and 1.56 nM in HBS-EP buffer were injected one after the other at a flow rate of 30 µl/min at 25° C. in the same cycle without regeneration between injections. Data from the reference cell were subtracted to compensate for bulk refractive index changes. In most cases, an injection of HBS-EP was also included as control so that the sensorgrams were double blanked. The surfaces were regenerated in HBS-EP buffer. Kinetic constants were calculated from the sensorgrams using the Langmuir 1:1 analyte model of the Biacore T200 Evaluation Software version 1.0. The resulting $K_D$ values of the interactions are presented in Table 5.

TABLE 5

$K_D$ value of the interaction of SEQ ID NO: 10, 13, 22 and 23 with C5 compared to $K_D$ value of C5 interaction with SEQ ID NO: 1

| SEQ ID NO: | Designation | $K_D$ (nM) |
| --- | --- | --- |
| 1 | PSI0242 | 1.3 |
| 10 | PSI0340 | 2.5 |
| 13 | PSI0378 | 2.1 |
| 22 | PSI0400 | 0.53 |
| 23 | PSI0410 | 1.3 |

The present data show that the stability-enhancing amino acid substitutions do not have any significant negative effect on the ability of the molecules to bind to C5, and thus do not influence their biological activities.

Example 6

Inhibition of Hemolysis

For studies of classical complement pathway function and inhibition thereof by the C5 binding compounds PSI0378 (SEQ ID NO:13) and PSI0410 (SEQ ID NO:23), and C5 binding polypeptide PSI0400 (SEQ ID NO:22), sheep erythrocytes were prepared from fresh sheep whole blood in Alsever's solution (Swedish National Veterinary Institute). The erythrocytes were thereafter treated with rabbit anti-sheep erythrocyte antiserum (Sigma) to become antibody sensitized sheep erythrocytes (EA). The whole process was conducted under aseptic conditions. All other reagents were from commercial sources.

The in vitro assay was run in 96-well U-form microtiter plate by consecutive additions of a test protein, a complement serum and EA suspension. The final concentrations of all reagents, in a total reaction volume of 50 µl per well and at pH 7.3-7.4, were: 0.15 mM CaCl 2; 0.5 mM MgCl 2; 3 mM NaN 3; 138 mM NaCl; 0.1% gelatin; 1.8 mM sodium barbital; 3.1 mM barbituric acid; 5 million EA; complement protein C5 serum at suitable dilution, and C5 binding compound or polypeptide at desired concentrations.

The C5 binding compounds and polypeptide were pre-incubated with the above described complement serum for 20 min on ice prior to starting the reaction by the addition of EA suspension. The hemolytic reaction was allowed to proceed at 37° C. under conditions of agitation for 45 min and was then optionally ended by addition of 100 µl ice-cold saline containing 0.02% Tween 20. The cells were centrifuged to the bottom of the vial and the upper portion, corresponding to 100 µl supernatant, was transferred to a transparent microplate having half-area and flat-bottom wells. The reaction results were analyzed as optical density using a microtiter plate reader at a wavelength of 415 nm.

A control sample (PSI0242, SEQ ID NO:1) and vehicle were included in each plate to define values for uninhibited and fully inhibited reactions, respectively. These values were used to calculate the % inhibition of the complement hemolysis at any given sample concentration. The inhibitory potencies (IC 50-values) of tested C5 binding compounds and polypeptide were defined by applying the same assay in the presence of a controlled concentration of human C5 added to C5 depleted serum. For highly potent inhibitors (low nanomolar to sub-nanomolar), a final C5 concentration of the reaction mixture was controlled at 0.1 nM, which was optionally established by using C5 depleted or deficient sera. The results are presented below in Table 6.

TABLE 6

The inhibitory capacity of C5-binding compounds and polypeptide

| SEQ ID NO: | Designation | Potency (%) | IC 50 (nM) |
| --- | --- | --- | --- |
| 1 | PSI0242 | 100 | 0.47 |
| 13 | PSI0378 | 83 | 0.58 |
| 22 | PSI0400 | — | 4 |
| 23 | PSI0410 | 107 | 0.49 |

The results from the hemolysis assay show that the improved C5 binding compounds PSI0378 (SEQ ID NO:13) and PSI0410 (SEQ ID NO:23) do not significantly differ from the reference compound PSI0242 (SEQ ID NO:1) in terms of function. The C5 binding polypeptide PSI0400 (SEQ ID NO:22) is functional in the assay and since it does not comprise an albumin binding domain, the results cannot be directly compared to those of the reference compound.

Example 7

Binding to Human Albumin

For assessment of the affinity of the C5 binding compounds for albumin, a human albumin ELISA was used, utilizing recombinant human albumin as coating (Novozymes) and commercially available antibodies from Affibody AB (primary) and DakoCytomation (detecting). A method standard prepared from PSI0242 (SEQ ID NO:1) and comprising a C5 binding polypeptide and an albumin binding domain of streptococcal protein G, was used for quantification of samples.

A 96-well microplate was coated with recombinant human albumin. The plate was then washed with phosphate buffered saline containing 0.05% Tween 20 (PBST) and blocked for 1-2 hours with 1% casein in PBS. After a plate wash, the standard, method controls, control sample and test samples are added to the plate. After incubation for 2 hours, unbound material was removed by a wash. A goat anti-AFFIBODY IgG (Affibody AB, cat no. 20.1000.01.0005) was added to the wells and the plate was incubated for 1.5 hours to allow binding to the bound C5 binding compounds. After a wash, rabbit anti-goat IgG HRP (DakoCytomation) was allowed to bind to the goat antibodies for 1 h. After a final wash, the amount of bound HRP was detected by addition of TMB substrate (3,3',5,5'-tetramethylbenzidine), which was converted to a blue product by the enzyme. Addition of 1 M hydrochloric acid after 30 minutes stopped the reaction and the color of the well contents changed from blue to yellow. The absorbance at 450 nm was measured photometrically, using the absorbance at 650 nm as a reference wavelength. The color intensity was proportional to the amount of PSI0242 (SEQ ID NO:1) and the sample concentrations were determined from the standard curve.

The C5 binding compounds comprising a derivative of the albumin binding domain from streptococcal protein G (ABD) were shown to be capable of binding to human albumin. Data is presented in Table 7.

TABLE 7

Summary of results from ELISA

| SEQ ID NO: | Designation | % of total protein content |
|---|---|---|
| 1 | PSI0242 | 103 |
| 13 | PSI0378 | 85 |
| 23 | PSI0410 | 150 |

The interpretation of the assay is that both the investigated C5 binding polypeptides with improved stability maintain their ability to bind human serum albumin.

Example 8

Three Month Stability Test of C5 Binding Z Variants and Polypeptides

The C5 binding variants and polypeptides that showed an improved stability compared to PSI0242 in the 2 week stability test at 37° C. (Example 2) were subjected to a longer 3 month stability test at 37° C. The setup of the stability test and the analysis by RPC was as described in Example 2. The evaluation of the stability was made by measuring the main peak of the chromatogram and calculating the corresponding percentage of the total protein content. The data from Example 2 is included in Table 8 below to make the interpretation easier.

TABLE 8

Stability of C5 binding polypeptides and compounds after 3 months of incubation at 37° C.

| SEQ ID NO: | Designation | 2 weeks, 37° C. Main peak (% of total protein) | 3 months, 37° C. Main peak (% of total protein) |
|---|---|---|---|
| 5 | PSI0334 | 73 | 16 |
| 13 | PSI0378 | 89 | 59 |
| 14 | PSI0379 | 88 | 58 |
| 15 | PSI0381 | 87 | 46 |
| 16 | PSI0383 | 91 | 59 |
| 23 | PSI0410 | 72 | 16 |
| 24 | PSI0403 | 77 | 35 |
| 25 | PSI0404 | 88 | 46 |

C5 binding compounds comprising the amino acid substitutions ND to SE in positions 52-53 (SEQ ID NO:13, 14, and 16) compared to PSI0242 showed a higher proportion of protein in the original form after 3 months at 37° C. than PSI0242 (SEQ ID NO:1), after 2 weeks under the same conditions (see Table 1). The other tested compounds also display an increased stability compared to the PSI0242.

Example 9

Generation, Stability Study and Binding Assessment of Scaffold-Modified Polypeptides with Specificity for Different Targets Generation of Scaffold-Modified Polypeptides with Specificity for Different Targets:

Polypeptide variants comprising the new scaffold described herein are generated by taking Z variant polypeptides with specificity for different targets, and performing site-directed mutagenesis at selected positions within the scaffold. The new molecules may, alternatively, be made by chemical synthesis of the entire molecule or by using other molecular biology methods, known to a person skilled in the art, to graft a binding motif of a Z variant polypeptide onto the new scaffold.

Comparative Stability Study of Scaffold-Modified Polypeptides with Specificity for Different Targets:

For each new polypeptide created as described above, the stability is compared to the stability of the original polypeptide or another comparable polypeptide. The polypeptides are subjected to different conditions, such as formulation in [25 mM NaP, 125 mM NaCl, pH 7.0] and incubation at 37° C. for 2 weeks as described in Example 2 and/or for 3 months as described in Example 8. The stability is assessed by analyzing the appearance of new variants by performing SDS-PAGE and RPC analyses as described in Example 2.

Polypeptides with the introduced modifications in scaffold positions are expected to show improved stability in similar to the results presented in Example 2 and Example 12.

Binding Assessment of Scaffold-Modified Polypeptides:

Polypeptides which have shown improved stability properties are further assessed in terms of preserved binding capacities to its target after introduction of alterations in the scaffold. Binding studies are performed on a biosensor instrument, or any other instrument known to the person skilled in the art and measuring the interaction between two or more molecules. For example, the target molecule, or a fragment thereof, is immobilized on a sensor chip of the instrument, and the sample containing the polypeptide to be tested is passed over the chip. Alternatively, the polypeptide to be tested is immobilized on a sensor chip of the instrument, and a sample containing the predetermined target, or a fragment thereof, is passed over the chip. The binding affinity may be tested in an experiment in which samples of the polypeptide are captured on antibody-coated ELISA plates and biotinylated predetermined target, or a fragment thereof, is added, followed by streptavidin conjugated HRP. TMB substrate is added and the absorbance at 450 nm is measured using a multi-well plate reader, such as Victor³ (Perkin Elmer). If a quantitative measure is desired, for example to determine the EC50 value (the half maximal effective concentration) for the interaction, ELISA may also be used. The response of the polypeptide against a dilution series of the predetermined target, or a fragment thereof, is measured using ELISA as described above. The results obtained by such experiments and EC50 values may be calculated from the results using for example GraphPad Prism 5 and non-linear regression. If the polypeptide contains an albumin binding domain, the effect on albumin binding will be assessed likewise, as described in Example 3 or as described in Example 7.

Polypeptides having the scaffold mutations described herein and, in addition, similar or improved binding capacities for its target, are considered to be better candidates for further development into e.g. biopharmaceutical products.

Example 10

Generation of Scaffold-Modified Polypeptides with Specificity for Four Different Targets Polypeptide variants comprising the new scaffold described herein were generated by taking Z variant polypeptides with specificity for different targets, and performing site-directed mutagenesis at selected positions within the scaffold. Amino acid substitutions at scaffold positions in the polypeptide variants Z02891 (SEQ ID NO:27), targeting the human epidermal growth factor receptor 2 (HER2); Z15805 (SEQ ID NO:30), targeting the platelet-derived growth factor receptor beta (PDGF-Rβ); Z10103 (SEQ ID NO:33), targeting the neonatal Fc receptor (FcRn); and Z09782 (SEQ ID NO:36), targeting the carbonic anhydrase IX (CAIX), are specified in Table 9.

TABLE 9

Original and inventive polypeptides produced and analyzed in terms of stability and function in the Examples described below

| SEQ ID NO | Designation | Target | Amino acid substitutions | Original vs inventive |
|---|---|---|---|---|
| 27 | Z02891 | HER2 | — | Original |
| 28 | Z17341 | HER2 | N52S, D53E | Inventive |
| 29 | Z17342 | HER2 | D36R, D37Q, S39E, N52S, D53E | Inventive |
| 30 | Z15805 | PDGF-Rβ | — | Original |
| 31 | Z17343 | PDGF-Rβ | N52S, D53E | Inventive |
| 32 | Z17344 | PDGF-Rβ | D36R, D37Q, S39E, N52S, D53E | Inventive |
| 33 | Z10103 | FcRn | — | Original |
| 34 | Z17347 | FcRn | N52S, D53E | Inventive |
| 35 | Z17348 | FcRn | D36R, D37Q, S39E, N52S, D53E | Inventive |
| 36 | Z09782 | CAIX | — | Original |

TABLE 9-continued

Original and inventive polypeptides produced and analyzed in terms of stability and function in the Examples described below

| SEQ ID NO | Designation | Target | Amino acid substitutions | Original vs inventive |
|---|---|---|---|---|
| 37 | Z17351 | CAIX | N52S, D53E | Inventive |
| 38 | Z17352 | CAIX | D36R, D37Q, S39E, N52S, D53E | Inventive |
| 39 | Z17355 | CAIX | D53E | Inventive |
| 40 | Z17357 | CAIX | D36R, D37Q, S39E, D53E | Inventive |
| 41 | Z17359 | CAIX | N52S | Inventive |
| 42 | Z17360 | CAIX | D36R, D37Q, S39E, N52S | Inventive |

All variants were cloned with an N-terminal 6× Histidine-tag ($His_6$) and obtained constructs encoded polypeptides in the format MGSSHHHHHHLQ-[Z#####] (SEQ ID NO: 73). Mutations were introduced in the plasmids of the inventive polypeptides using overlapping oligonucleotide primer pairs encoding the desired amino acid substitutions and by applying established molecular biology techniques. The correct plasmid sequences were verified by DNA sequencing.

E coli (strain T7E2) cells (GeneBridge) were transformed with plasmids containing the gene fragments encoding the original and the inventive polypeptides. The cells were cultivated at 37° C. in TSB-YE medium supplemented with 50 μg/ml kanamycin and protein expression was subsequently induced by addition of IPTG. Pelleted cells were disrupted using a FASTPREP-24 homogenizer (Nordic Biolabs) and cell debris was removed by centrifugation. Each supernatant containing the Z variant as a $His_6$-tagged protein was purified by immobilized metal ion affinity chromatography (IMAC) using His GRAVITRAP columns (GE Healthcare) according to the manufacturers instructions. Purified Z variants were buffer exchanged to phosphate-buffered saline (PBS; 1.47 mM $KH_2PO_4$, 8.1 mM $Na_2HPO_4$, 137 mM NaCl, 2.68 mM KCl, pH 7.4) using PD-10 desalting columns (GE Healthcare). The correct identity of each polypeptide was verified by SDS-PAGE and HPLC-MS.

Example 11

Circular Dichroism Spectroscopy Analysis of Scaffold-Modified Polypeptides

Circular dichroism (CD) analysis was carried out to determine the melting temperatures (Tm) and assess potential changes in the secondary structure of the inventive polypeptides as a result of the amino acid substitutions.

Purified $His_6$-tagged Z variants were diluted to 0.5 mg/ml in PBS. For each diluted Z variant, a CD spectrum at 250-195 nm was recorded at 20° C. A variable temperature measurement (VTM) was performed to determine the Tm. In the VTM, the absorbance was measured at 221 nm while the temperature was raised from 20 to 90° C., with a temperature slope of 5° C./min. After the VTM, a second CD spectrum at 250-195 nm was recorded at 20° C. The CD measurements were performed on a Jasco J-810 spectropolarimeter (Jasco Scandinavia AB) using a cell with an optical pathlength of 1 mm.

The Tm of each respective polypeptide as determined from the midpoint of the transition in the CD signal vs. temperature plot is shown in Table 10. All mutated polypeptides showed preserved alphahelical structure and refolded reversibly or nearly reversibly even after heating to 90° C. A selected set of CD spectra are shown in FIG. 7A-7G.

TABLE 10

Melting temperatures for original and invenitve Z variants determined by CD

| SEQ ID NO | Designation | Target | Tm (° C.) | Original vs inventive |
|---|---|---|---|---|
| 27 | Z02891 | HER2 | 70 | Original |
| 28 | Z17341 | HER2 | 66 | Inventive |
| 29 | Z17342 | HER2 | 62 | Inventive |
| 30 | Z15805 | PDGF-Rβ | 48 | Original |
| 31 | Z17343 | PDGF-Rβ | 46 | Inventive |
| 32 | Z17344 | PDGF-Rβ | 42 | Inventive |
| 33 | Z10103 | FcRn | 48 | Original |
| 34 | Z17347 | FcRn | 50 | Inventive |
| 35 | Z17348 | FcRn | 44 | Inventive |
| 36 | Z09782 | CAIX | 43 | Original |
| 37 | Z17351 | CAIX | 40 | Inventive |
| 38 | Z17352 | CAIX | 45 | Inventive |
| 39 | Z17355 | CAIX | 43 | Inventive |
| 40 | Z17357 | CAIX | 47 | Inventive |
| 41 | Z17359 | CAIX | 41 | Inventive |
| 42 | Z17360 | CAIX | 46 | Inventive |

Example 12

Comparative Stability Study of Scaffold-Modified Polypeptides with Specificity for Four Different Targets For each new polypeptide created as described in Example 10, the stability was compared to the stability of the original polypeptide. The polypeptides, formulated in PBS pH 7.4, were diluted to 1 mg/ml and 200 μl aliquotes were incubated at 37° C. for 2 weeks. Samples collected prior to and after the stability test were analyzed by SDS-PAGE using 10% Bis-Tris NuPAGE gels (Invitrogen) and by loading 5 μg protein into each well. The resulting Coomassie blue stained gels are shown in FIG. 8A-8D. The stability was assessed by the appearance of new variants after incubation at the elevated temperature and mutated variants were compared to respective original polypeptide.

All polypeptides with modifications introduced in scaffold positions as outlined in Table 9 showed improved stability compared to the respective original polypeptide. In samples of the original polypeptides a second band was visible on the gel just above the main band. A corresponding second band was not visible in the samples of the inventive polypeptides with the substitution D53E and/or N52S. This is in analogy with results presented in Examples 2 and 4. Thus, the stabilizing effect observed for the inventive scaffold mutations appears to be a general effect regardless of the target specificity of the Z variant or polypeptide comprising said Z variant. Polypeptides with the substitutions D53E and/or N52S, alone or combined with the substitutions D36R, D37Q and S39E, showed similar profiles on the SDS-PAGE gel. The substitution D53E alone or in combination with the substitutions D36R, D37Q and S39E appeared to reduce the amount of the species with an alternative confirmation observed as a second band on the SDS-PAGE gel, but could not completely prevent the formation of this species.

Example 13

Binding Assessment of Scaffold-Modified Polypeptides

A set of polypeptides showing improved stability properties in Example 12 were further assessed in terms of preserved binding capacities to their targets after introduction of alterations in the scaffold, as well as after having been subjected to the stability test, i.e. incubated at 37° C. for 2 weeks. Comparative kinetic constants ($k_{on}$ and $k_{off}$) and affinities ($K_D$) were determined using a Biacore 2000 instrument. The target proteins human HER2-Fc (R&D Systems, cat. no. 1129-ER-050), human PDGF-Rβ (R&D Systems, cat. no. 385-PR-100/CF), human FcRn (Biorbyt, cat. no. orb 84388) and human CAIX (R&D Systems, cat. no. 2188-CA), respectively, were immobilized on the carboxylated dextran layer surface of CM5 chips (GE Healthcare). The immobilization was performed using amine coupling chemistry according to the manufacturer's protocol and using HBS-EP as running buffer. One flow cell surface on the chip was activated and deactivated for use as blank during analyte injections. The immobilization level of target protein on the respective surface was approximately 850 RU for HER2, 2200 RU for PDGF-Rβ, 750 for FcRn and 580 RU for CAIX.

HBS-EP (HER2, PDGF-Rβ, CAIX) or a pH 6.0 $Na_2HPO_4$/citric acid buffer (126 mM $Na_2HPO_4$, 37 mM citric acid) (FcRn) was used as running buffer and the flow rate was 30 μl/min in the binding experiments performed at 25° C. as further described below.

The Z variants Z02891 (SEQ ID NO:27), Z17341 (SEQ ID NO:28), and Z17342 (SEQ ID NO:29) targeting HER2 were diluted in running buffer to final concentrations of 3.33, 10, 30 and 90 nM and injected for 5 minutes, followed by 30 minutes of dissociation in running buffer. Regeneration by four pulses alternating between 10 mM HCl and 10 mM NaOH followed by 5 min equilibration in running buffer was applied after each analyte injection.

The Z variants Z15805 (SEQ ID NO:30), Z17343 (SEQ ID NO:31), and Z17344 (SEQ ID NO:32) targeting PDGF-R13 were diluted in running buffer to final concentrations of 6.67, 20, 60 and 180 nM and injected for 5 minutes, followed by 20 minutes of dissociation in running buffer. Regeneration by three pulses of 10 mM NaOH followed by 5 min equilibration in running buffer was applied after each analyte injection.

The Z variants Z10103 (SEQ ID NO:33), Z17347 (SEQ ID NO:34), and Z17348 (SEQ ID NO:35) targeting FcRn were diluted in running buffer to final concentrations of 3.33, 10 and 30 nM and injected for 3 minutes, followed by 15 minutes of dissociation in running buffer. Regeneration by three pulses of HBS-EP followed by 10 min equilibration in running buffer was applied after each analyte injection.

The Z variants Z09782 (SEQ ID NO:36), Z17351 (SEQ ID NO:37), Z17355 (SEQ ID NO:39), and Z17359 (SEQ ID NO:41) targeting CAIX were diluted in running buffer to final concentrations of 30, 90 and 270 nM and injected for 5 minutes, followed by 15 minutes of dissociation in running buffer. Regeneration by three pulses of 10 mM glycin-HCl pH 3.0 followed by 5 min equilibration in running buffer was applied after each analyte injection.

Kinetic constants were calculated from the sensorgrams using the Langmuir 1:1 model (HER2, FcRn, CAIX) or the 1:1 binding with mass transfer model (PDGF-Rβ) of the BiaEvaluation software 4.1 (GE Healthcare). Curves of the blank surface were subtracted from the curves of the ligand surfaces and the data from the buffer cycles were subtracted from the data of the test-sample cycles to correct for any drift in signal.

The comparative kinetic constants for Z variants binding to its target molecule are shown in Table 11 and sensorgrams for a subset of the analyzed interactions are shown in FIG. 9A-9D. The data show that the affinity is only marginally effected by the substitutions ND to SE in position 52-53 and for a couple of variants, Z17341 (SEQ ID NO:28) and Z17343 (SEQ ID NO:31), the affinity is even slightly improved. A combination of the substitutions ND to SE in position 52-53 with the substitutions D36R, D37Q and S39E, such as in Z17342 (SEQ ID NO:29), Z17344 (SEQ ID NO:32) and Z17348 (SEQ ID NO:35) had a more negative effect on the affinity primarily due to faster dissociation rates, but yet, functional binders were obtained with $K_D$ in the range $10^{-9}$M. The assessed variants also had preserved binding capabilities after 2 weeks incubation at 37° C.

TABLE 11

Comparative kinetic analysis of original and inventive polypeptides

| SEQ ID NO: | Test sample | Original vs Inventive | $k_a$ (Ms$^{-1}$) | $k_d$ (s$^{-1}$) | $K_D$ (M)* | $K_{DInv}/K_{DOrig}$** | $K_{D(2w)}/K_{D(0)}$*** |
|---|---|---|---|---|---|---|---|
| HER2 binding Z variants | | | | | | | |
| 27 | Z02891 (0) | Original | $1.33 \times 10^6$ | $7.10 \times 10^{-5}$ | $5.4 \times 10^{-11}$ | 1.0 | |
| 27 | Z02891 (2w) | Original | $1.15 \times 10^6$ | $7.19 \times 10^{-5}$ | $6.2 \times 10^{-11}$ | 1.0 | 1.17 |
| 28 | Z17341 (0) | Inventive | $1.88 \times 10^6$ | $8.35 \times 10^{-5}$ | $4.5 \times 10^{-11}$ | 0.83 | |
| 28 | Z17341 (2w) | Inventive | $2.06 \times 10^6$ | $8.91 \times 10^{-5}$ | $4.3 \times 10^{-11}$ | 0.69 | 0.97 |
| 29 | Z17342 (0) | Inventive | $8.94 \times 10^5$ | $1.57 \times 10^{-3}$ | $1.8 \times 10^{-9}$ | 33 | |
| 29 | Z17342 (2w) | Inventive | $6.49 \times 10^5$ | $1.50 \times 10^{-3}$ | $2.3 \times 10^{-9}$ | 37 | 1.31 |
| PDGF-Rβ binding Z variants | | | | | | | |
| 30 | Z15805 (0) | Original | $7.15 \times 10^6$ | $1.39 \times 10^{-3}$ | $1.9 \times 10^{-10}$ | 1.0 | |
| 30 | Z15805 (2w) | Original | $5.81 \times 10^6$ | $1.66 \times 10^{-3}$ | $2.9 \times 10^{-10}$ | 1.0 | 1.47 |
| 31 | Z17343 (0) | Inventive | $4.80 \times 10^6$ | $1.77 \times 10^{-3}$ | $3.7 \times 10^{-10}$ | 1.90 | |
| 31 | Z17343 (2w) | Inventive | $6.45 \times 10^6$ | $1.71 \times 10^{-3}$ | $2.3 \times 10^{-10}$ | 0.93 | 0.72 |
| 32 | Z17344 (0) | Inventive | $5.15 \times 10^7$ | $6.16 \times 10^{-2}$ | $1.2 \times 10^{-9}$ | 6.19 | |
| 32 | Z17344 (2w) | Inventive | $5.62 \times 10^7$ | $6.23 \times 10^{-2}$ | $1.1 \times 10^{-9}$ | 3.88 | 0.93 |
| FcRn binding Z variants | | | | | | | |
| 33 | Z10103 (0) | Original | $1.60 \times 10^6$ | $4.56 \times 10^{-3}$ | $2.9 \times 10^{-9}$ | 1.0 | |
| 33 | Z10103 (2w) | Original | $3.15 \times 10^6$ | $5.75 \times 10^{-3}$ | $1.8 \times 10^{-9}$ | 1.0 | 0.64 |
| 34 | Z17347 (0) | Inventive | $1.18 \times 10^6$ | $7.99 \times 10^{-3}$ | $6.7 \times 10^{-9}$ | 2.36 | |
| 34 | Z17347 (2w) | Inventive | $2.27 \times 10^6$ | $8.79 \times 10^{-3}$ | $3.9 \times 10^{-9}$ | 2.13 | 0.57 |
| 35 | Z17348 (0) | Inventive | $1.82 \times 10^6$ | $1.00 \times 10^{-2}$ | $5.5 \times 10^{-9}$ | 1.93 | |
| 35 | Z17348 (2w) | Inventive | $1.28 \times 10^6$ | $8.09 \times 10^{-3}$ | $6.3 \times 10^{-9}$ | 3.46 | 1.14 |
| CAIX binding Z variants | | | | | | | |
| 36 | Z09782 (0) | Original | $2.08 \times 10^5$ | $1.46 \times 10^{-3}$ | $7.0 \times 10^{-9}$ | 1.0 | |
| 36 | Z09782 (2w) | Original | $1.40 \times 10^5$ | $1.38 \times 10^{-3}$ | $9.9 \times 10^{-9}$ | 1.0 | 1.41 |
| 37 | Z17351 (0) | Inventive | $1.51 \times 10^5$ | $2.63 \times 10^{-3}$ | $1.8 \times 10^{-8}$ | 2.49 | |
| 37 | Z17351 (2w) | Inventive | $1.91 \times 10^5$ | $2.86 \times 10^{-3}$ | $1.5 \times 10^{-8}$ | 1.52 | 0.86 |
| 39 | Z17355 (0) | Inventive | $1.57 \times 10^5$ | $1.23 \times 10^{-3}$ | $7.9 \times 10^{-9}$ | 1.12 | |
| 39 | Z17355 (2w) | Inventive | $1.16 \times 10^5$ | $1.23 \times 10^{-3}$ | $1.1 \times 10^{-8}$ | 1.07 | 1.35 |
| 41 | Z17359 (0) | Inventive | $1.68 \times 10^5$ | $2.15 \times 10^{-3}$ | $1.3 \times 10^{-8}$ | 1.82 | |
| 41 | Z17359 (2w) | Inventive | $1.78 \times 10^5$ | $2.33 \times 10^{-3}$ | $1.3 \times 10^{-8}$ | 1.32 | 1.02 |

*The $K_D$ values should not be regarded as absolute, as these were determined for comparative purposes and only included a limited number of sample concentrations.
**Relative $K_D$ comparing the $K_D$ of respective inventive polypeptide with the $K_D$ of its original polypeptide (set to 1.0) either prior to (0) or after the stability test (2w) described in Example 12.
***Relative $K_D$ comparing the $K_D$ from (2w) with $K_D$ from (0) for each polypeptide pair identical in sequence.

Itemized List of Embodiments

1. Polypeptide comprising an amino acid sequence selected from:
i)

(SEQ ID NO: 55)
EX$_2$X$_3$X$_4$AX$_6$X$_7$EIX$_{10}$ X$_{11}$LPNLX$_{16}$X$_{17}$X$_{18}$QX$_{20}$

X$_{21}$AFIX$_{25}$X$_{26}$LX$_{28}$X$_{29}$X$_{30}$ PX$_{32}$QSX$_{35}$X$_{36}$LLX$_{39}$E

AKKLX$_{45}$X$_{46}$X$_{47}$Q, wherein each of X$_2$, X$_3$, X$_4$, X$_6$, X$_7$, X$_{10}$, X$_{11}$, X$_{17}$, X$_{18}$, X$_{20}$, X$_{21}$, X$_{25}$ and X$_{28}$ independently corresponds to any amino acid residue; and
wherein, independently of each other,
X$_{16}$ is selected from N and T;
X$_{26}$ is selected from K and S;
X$_{29}$X$_{30}$PX$_{32}$ is selected from DDPS and RQPE;
X$_{35}$ is selected from A and S;
X$_{36}$ is selected from E and N;
X$_{39}$ is selected from A, C and S;
X$_{45}$ is selected from E, N and S;
X$_{46}$ is selected from D, E and S, provided that X$_{46}$ is not D when X$_{45}$ is N;
X$_{47}$ is selected from A and S; and ii) an amino acid sequence which has at least 91% identity to the sequence defined in i), provided that X$_{46}$ is not D when X$_{45}$ is N.

2. Polypeptide according to item 1, wherein X$_{16}$ is T.
3. Polypeptide according to item 1 or 2, wherein X$_{26}$ is K.
4. Polypeptide according to any preceding item, wherein X$_{29}$X$_{30}$PX$_{32}$ is DDPS.
5. Polypeptide according to item 1-3, wherein X$_{29}$X$_{30}$PX$_{32}$ is RQPE.
6. Polypeptide according to any preceding item, wherein X$_{35}$ is S.
7. Polypeptide according to any preceding item, wherein X$_{36}$ is E.
8. Polypeptide according to any preceding item, wherein X$_{39}$ is S.
9. Polypeptide according to any preceding item, wherein X$_{45}$ is selected from E and S.
10. Polypeptide according to item 9, wherein X$_{45}$ is E.
11. Polypeptide according to item 9, wherein X$_{45}$ is S.
12. Polypeptide according to any preceding item, wherein X$_{46}$ is selected from E and S.

13. Polypeptide according to item 12, wherein $X_{46}$ is E.
14. Polypeptide according to item 12, wherein $X_{46}$ is S.
15. Polypeptide according to item 12, wherein $X_{46}$ is D.
16. Polypeptide according to any preceding item, provided that $X_{46}$ is not D or E when $X_{45}$ is N.
17. Polypeptide according to any preceding item, wherein $X_{45}X_{46}$ is selected from EE, ES, SE and SS.
18. Polypeptide according to item 17, wherein $X_{45}X_{46}$ is selected from ES and SE.
19. Polypeptide according to item 18, wherein $X_{45}X_{46}$ is ES.
20. Polypeptide according to item 18, wherein $X_{45}X_{46}$ is SE.
21. Polypeptide according to item 18, wherein $X_{45}X_{46}$ is SD.
22. Polypeptide according to any preceding item, wherein $X_{47}$ is S.
23. Polypeptide according to any one of items 1-22, comprising additional amino acid residues.
24. Polypeptide according to item 23, comprising additional amino acid residues at the C-terminus of said polypeptide.
25. Polypeptide according to item 24, wherein the additional amino acid residues at the C-terminus of said polypeptide comprise AP.
26. Polypeptide according to item 23, comprising additional amino acid residues at the N-terminus of said polypeptide.
27. Polypeptide according to item 26, wherein the additional amino acid residues at the N-terminus of said polypeptide comprise AEAKYAK.
28. Polypeptide according to any one of items 23-27, wherein said additional amino acid residues are added for the purpose of binding, production, purification, stabilization, coupling or detection of the polypeptide.
29. Polypeptide according to any one of items 23-28, wherein said additional amino acid residues constitute one or more polypeptide domain(s).
30. Polypeptide according to item 29, wherein said one or more polypeptide domain(s) has a function selected from the group of a binding function, an enzymatic function, a metal ion chelating function and a fluorescent function, or mixtures thereof.
31. Polypeptide according to any one of items 1-28, which comprises an amino acid sequence selected from:

(SEQ ID NO: 56)
YAK $EX_2X_3X_4AX_6X_7EIX_{10}$ $X_{11}LPNLX_{16}X_{17}X_{18}QX_{20}$ $X_{21}AFIX_{25}X_{26}LX_{25}X_{29}X_{30}$ $PX_{32}QSX_{35}X_{36}LLX_{39}E$ $AKKLX_{45}X_{46}X_{47}Q$ AP;
and (SEQ ID NO: 57)
FNK $EX_2X_3X_4AX_6X_7EIX_{10}$ $X_{11}LPNLX_{16}X_{17}X_{18}QX_{20}$ $X_{21}AFIX_{25}X_{26}LX_{25}X_{29}X_{30}$ $PX_{32}QSX_{35}X_{36}LLX_{39}E$ $AKKLX_{45}X_{46}X_{47}Q$ AP, wherein each $X_y$ is as defined in any one of items 1-22.

32. Polypeptide according to item 31, which comprises an amino acid sequence selected from:

(SEQ ID NO: 58)
ADNNFNK $EX_2X_3X_4AX_6X_7EIX_{10}$ $X_{11}LPNLX_{16}X_{17}X_{18}QX_{20}$ $X_{21}AFIX_{25}X_{26}LX_{28}X_{29}X_{30}$ $PX_{32}QSX_{35}X_{36}LLX_{39}E$ $AKKLX_{45}X_{46}X_{47}Q$ APK;

(SEQ ID NO: 59)
ADNKFNK $EX_2X_3X_4AX_6X_7EIX_{10}$ $X_{11}LPNLX_{16}X_{17}X_{18}QX_{20}$ $X_{21}AFIX_{25}X_{26}LX_{28}X_{29}X_{30}$ $PX_{32}QSX_{35}X_{36}LLX_{39}E$ $AKKLX_{45}X_{46}X_{47}Q$ APK;

(SEQ ID NO: 60)
VDNKFNK $EX_2X_3X_4AX_6X_7EIX_{10}$ $X_{11}LPNLX_{16}X_{17}X_{18}QX_{20}$ $X_{21}AFIX_{25}X_{26}LX_{28}X_{29}X_{30}$ $PX_{32}QSX_{35}X_{36}LLX_{39}E$ $AKKLX_{45}X_{46}X_{47}Q$ APK;

(SEQ ID NO: 61)
VDAKYAK $EX_2X_3X_4AX_6X_7EIX_{10}$ $X_{11}LPNLX_{16}X_{17}X_{18}QX_{20}$ $X_{21}AFIX_{25}X_{26}LX_{28}X_{29}X_{30}$ $PX_{32}QSX_{35}X_{36}LLX_{39}E$ $AKKLX_{45}X_{46}X_{47}Q$ APK;
and (SEQ ID NO: 62)
AEAKYAK $EX_2X_3X_4AX_6X_7EIX_{10}$ $X_{11}LPNLX_{16}X_{17}X_{18}QX_{20}$ $X_{21}AFIX_{25}X_{26}LX_{25}X_{29}X_{30}$ $PX_{32}QSX_{35}X_{36}LLX_{39}E$ $AKKLX_{45}X_{46}X_{47}Q$ APK;

wherein each $X_y$ is as defined in any one of items 1-22.

33. Polypeptide according to any one of items 1-32 having an affinity for a predetermined target, wherein said target is optionally selected from the group consisting of ABD, HER2, TNFα, EGFR, IGF1R, IgG, PDGFRβ, HER3, C5, FcRn, CAIX, amyloid β, CD4, IL8, IL6 and insulin.

34. Fusion polypeptide comprising a polypeptide according to any one of items 1-33 as a moiety.

35. Polypeptide or fusion polypeptide according to any one of items 1-34, further comprising a label.

36. Polypeptide or fusion polypeptide according to any one of items 1-35, further comprising a therapeutic agent.

37. Use of a polypeptide or fusion polypeptide according to any one of items 1-36 as a detection reagent, capture reagent or separation reagent.

38. Polypeptide or fusion polypeptide according to any one of items 1-36 for use in therapy.

39. Polypeptide or fusion polypeptide according to any one of items 1-36 for use as a diagnostic agent.

40. Polynucleotide encoding a polypeptide or fusion polypeptide according to any one of items 1-34.

41. Population of polypeptide variants based on a common scaffold, each polypeptide in the population comprising an amino acid sequence selected from:
i)

(SEQ ID NO: 55)
$EX_2X_3X_4AX_6X_7EIX_{10}$ $X_{11}LPNLX_{16}X_{17}X_{18}QX_{20}$ $X_{21}AFIX_{25}X_{26}LX_{28}X_{29}X_{30}$ $PX_{32}QSX_{35}X_{36}LLX_{39}E$ $AKKLX_{45}X_{46}X_{47}Q$, wherein each of $X_2$, $X_3$, $X_4$, $X_6$, $X_7$, $X_{10}$, $X_{11}$, $X_{17}$, $X_{18}$, $X_{20}$, $X_{21}$, $X_{25}$ and $X_{28}$ independently corresponds to any amino acid residue; and
wherein, independently of each other,
$X_{16}$ is selected from N and T;
$X_{26}$ is selected from K and S;
$X_{29}X_{30}PX_{32}$ is selected from DDPS and RQPE;
$X_{35}$ is selected from A and S;

$X_{36}$ is selected from E and N;
$X_{39}$ is selected from A, C and S;
$X_{45}$ is selected from E, N and S;
$X_{46}$ is selected from D, E and S, provided that $X_{46}$ is not D when $X_{45}$ is N;
$X_{47}$ is selected from A and S; and ii) an amino acid sequence which has at least 91% identity to the sequence defined in i), provided that $X_{46}$ is not D when $X_{45}$ is N.

42. Population according to item 41, which comprises at least $1 \times 10^4$ unique polypeptide molecules.

43. Population according to item 42, which comprises at least $1 \times 10^6$ unique polypeptide molecules.

44. Population according to item 43, which comprises at least $1 \times 10^8$ unique polypeptide molecules.

45. Population according to item 44, which comprises at least $1 \times 10^{10}$ unique polypeptide molecules.

46. Population according to item 45, which comprises at least $1 \times 10^{12}$ unique polypeptide molecules.

47. Population according to item 46, which comprises at least $1 \times 10^{14}$ unique polypeptide molecules.

48. Population of polynucleotides, characterized in that each member thereof encodes a member of a population of polypeptides according to any one of items 41-47.

49. Combination of a polypeptide population according to any one of items 41-47 with a polynucleotide population according to item 48, wherein each member of said population of polypeptides is physically or spatially associated with the polynucleotide encoding that member via means for genotype-phenotype coupling.

50. Combination according to item 49, wherein said means for genotype-phenotype coupling comprises a phage display system.

51. Combination according to item 49, wherein said means for genotype-phenotype coupling comprises a cell surface selection display system.

52. Combination according to item 51, wherein said cell surface display system comprises prokaryotic cells.

53. Combination according to item 52, wherein said prokaryotic cells are Gram-positive cells.

54. Combination according to item 51, wherein said cell surface display system comprises eukaryotic cells.

55. Combination according to item 54, wherein said eukaryotic cells are yeast cells.

56. Combination according to item 49, wherein said means for genotype-phenotype coupling comprises a cell free display system.

57. Combination according to item 56, wherein said cell free display system comprises a ribosome display system.

58. Combination according to item 56, wherein said cell free display system comprises an in vitro compartmentalization display system.

59. Combination according to item 56, wherein said cell free display system comprises a system for cis display.

60. Combination according to item 56, wherein cell free display system comprises a microbead display system.

61. Combination according to item 49, wherein said means for genotype-phenotype coupling comprises a non-display system.

62. Combination according to item 61, wherein said non-display system is protein-fragment complementation assay.

63. Method for selecting a desired polypeptide having an affinity for a predetermined target from a population of polypeptides, comprising the steps:
(a) providing a population of polypeptides according to any one of items 41-47;
(b) bringing the population of polypeptides into contact with the predetermined target under conditions that enable specific interaction between the target and at least one desired polypeptide having an affinity for the target; and
(c) selecting, on the basis of said specific interaction, the at least one desired polypeptide from the remaining population of polypeptides.

64. Method according to item 63, wherein step (a) comprises the preparatory steps of providing a population of polynucleotides according to item 48 and expressing said population of polynucleotides to yield said population of polypeptides.

65. Method according to item 64, wherein each member of said population of polypeptides is physically or spatially associated with the polynucleotide encoding that member via means for genotype-phenotype coupling.

66. Method according to item 65, wherein said means for genotype-phenotype coupling is as defined in any one of items 50-62.

67. Method for isolating a polynucleotide encoding a desired polypeptide having an affinity for a predetermined target, comprising the steps:
selecting said desired polypeptide and the polynucleotide encoding it from a population of polypeptides using the method according to item 63; and
isolating the thus separated polynucleotide encoding the desired polypeptide.

68. Method for identifying a desired polypeptide having an affinity for a predetermined target, comprising the steps:
isolating a polynucleotide encoding said desired polypeptide using the method according to item 67; and
sequencing the polynucleotide to establish by deduction the amino acid sequence of said desired polypeptide.

69. Method for selecting and identifying a desired polypeptide having an affinity for a predetermined target from a population of polypeptides, comprising the steps:
(a) synthesizing each member of a population of polypeptides according to any one of items 41-47 on a separate carrier or bead;
(b) selecting or enriching the carriers or beads based on the interaction of the polypeptide with the predetermined target; and
(c) identifying the polypeptide by protein characterization methodology.

70. Method according to item 69, wherein the protein characterization methodology used in step (c) is mass spectrometric analysis.

71. Method for production of a desired polypeptide having an affinity for a predetermined target, comprising the steps:
isolating and identifying a desired polypeptide using the method according to item 68 or selecting and identifying a desired polypeptide using the method according to any one of items 69 and 70; and
producing said desired polypeptide.

72. Method according to item 71, wherein said production is carried out using chemical synthesis of the desired polypeptide de novo.

73. Method according to item 71, wherein said production is carried out using recombinant expression of a polynucleotide encoding the desired polypeptide.

74. Method for production of a desired polypeptide having an affinity for a predetermined target, comprising the steps:
(a1) isolating a polynucleotide encoding said desired polypeptide using the method according to item 68; or
(a2) backtranslating a polypeptide identified using the selection and identification method according to any one of items 69 and 70; and
(b), following either (a1) or (a2), expressing the thus isolated polynucleotide to produce said desired polypeptide.

The invention claimed is:

1. A polypeptide comprising an amino acid sequence selected from:

i)

(SEQ ID NO: 55)
EX$_2$X$_3$X$_4$AX$_6$X$_7$EIX$_{10}$ X$_{11}$LPNLX$_{16}$X$_{17}$X$_{18}$QX$_{20}$

X$_{21}$AFIX$_{25}$X$_{26}$LX$_{28}$X$_{29}$X$_{30}$ PX$_{32}$QSX$_{35}$X$_{36}$LLX$_{39}$E

AKKLX$_{45}$X$_{46}$X$_{47}$Q, wherein each of X$_2$, X$_3$, X$_4$, X$_6$, X$_7$, X$_{10}$, X$_{11}$, X$_{17}$, X$_{18}$, X$_{20}$, X$_{21}$, X$_{25}$ and X$_{28}$ independently corresponds to any amino acid residue; and wherein, independently of each other, X$_{16}$ is selected from N and T;
X$_{26}$ is selected from K and S;
X$_{29}$X$_{30}$PX$_{32}$ is selected from DDPS and RQPE;
X$_{35}$ is selected from A and S;
X$_{36}$ is selected from E and N;
X$_{39}$ is selected from A, C and S;
X$_{45}$ is selected from E, N and S;
X$_{46}$ is selected from D, E and S, provided that X$_{46}$ is not D when X$_{45}$ is N;
X$_{47}$ is selected from A and S; and ii) an amino acid sequence which has at least 91% identity to the sequence defined in i), provided that X$_{46}$ is not D when X$_{45}$ is N.

2. The polypeptide according to claim 1, wherein X$_{45}$ is S.

3. The polypeptide according to claim 1, wherein X$_{45}$X$_{46}$ is selected from ES and SE.

4. The polypeptide according to claim 3, wherein X$_{45}$X$_{46}$ is SE.

5. The polypeptide according to claim 1, which comprises an amino acid sequence selected from:

(SEQ ID NO: 56)
YAK EX$_2$X$_3$X$_4$AX$_6$X$_7$EIX$_{10}$ X$_{11}$LPNLX$_{16}$X$_{17}$X$_{18}$QX$_{20}$

X$_{21}$AFIX$_{25}$X$_{26}$LX$_{25}$X$_{29}$X$_{30}$ PX$_{32}$QSX$_{35}$X$_{36}$LLX$_{39}$E

AKKLX$_{45}$X$_{46}$X$_{47}$Q AP;
and (SEQ ID NO: 57)
FNK EX$_2$X$_3$X$_4$AX$_6$X$_7$EIX$_{10}$ X$_{11}$LPNLX$_{16}$X$_{17}$X$_{18}$QX$_{20}$ X$_{21}$AFIX$_{25}$X$_{26}$LX$_{25}$X$_{29}$X$_{30}$ PX$_{32}$QSX$_{35}$X$_{36}$LLX$_{39}$E

AKKLX$_{45}$X$_{46}$X$_{47}$Q AP, wherein each X$_y$ is as defined in claim 1.

6. A fusion polypeptide comprising a polypeptide according to claim 1 as a moiety.

7. A polynucleotide encoding a polypeptide according to claim 1 or fusion polypeptide according to claim 6.

8. A population of polypeptide variants based on a common scaffold, each polypeptide in the population comprising an amino acid sequence selected from:

i)

(SEQ ID NO: 55)
EX$_2$X$_3$X$_4$AX$_6$X$_7$EIX$_{10}$ X$_{11}$LPNLX$_{16}$X$_{17}$X$_{18}$QX$_{20}$

X$_{21}$AFIX$_{25}$X$_{26}$LX$_{28}$X$_{29}$X$_{30}$ PX$_{32}$QSX$_{35}$X$_{36}$LLX$_{39}$E

AKKLX$_{45}$X$_{46}$X$_{47}$Q, wherein each of X$_2$, X$_3$, X$_4$, X$_6$, X$_7$, X$_{10}$, X$_{11}$, X$_{17}$, X$_{18}$, X$_{20}$, X$_{21}$, X$_{25}$ and X$_{28}$ independently corresponds to any amino acid residue; and wherein, independently of each other, X$_{16}$ is selected from N and T;
X$_{26}$ is selected from K and S;
X$_{29}$X$_{30}$PX$_{32}$ is selected from DDPS and RQPE;
X$_{35}$ is selected from A and S;
X$_{36}$ is selected from E and N;
X$_{39}$ is selected from A, C and S;
X$_{45}$ is selected from E, N and S;
X$_{46}$ is selected from D, E and S, provided that X$_{46}$ is not D when X$_{45}$ is N;
X$_{47}$ is selected from A and S; and ii) an amino acid sequence which has at least 91% identity to the sequence defined in i), provided that X$_{46}$ is not D when X$_{45}$ is N.

9. The population according to claim 8, which comprises at least $1\times10^4$ unique polypeptide molecules.

10. A population of polynucleotides, characterized in that each member thereof encodes a member of a population of polypeptides according to claim 8.

11. A composition comprising a polypeptide population according to claim 8 and a polynucleotide population according to claim 10, wherein each member of said population of polypeptides is physically or spatially associated with the polynucleotide encoding that member via means for genotype-phenotype coupling.

12. The composition according to claim 11, wherein said means for genotype-phenotype coupling comprises a phage display system.

13. A method for selecting a desired polypeptide having an affinity for a predetermined target from a population of polypeptides, comprising the steps:

(a) providing a population of polypeptides according to claim 8;
(b) bringing the population of polypeptides into contact with the predetermined target under conditions that enable specific interaction between the target and at least one desired polypeptide having an affinity for the target; and
(c) selecting, on the basis of said specific interaction, the at least one desired polypeptide from the remaining population of polypeptides.

14. A method for isolating a polynucleotide encoding a desired polypeptide having an affinity for a predetermined target, comprising the steps:

selecting said desired polypeptide and the polynucleotide encoding it from a population of polypeptides using the method according to claim 13; and isolating the thus separated polynucleotide encoding the desired polypeptide.

15. A method for identifying a desired polypeptide having an affinity for a predetermined target, comprising the steps:
   isolating a polynucleotide encoding said desired polypeptide using the method according to claim 14; and
   sequencing the polynucleotide to establish by deduction the amino acid sequence of said desired polypeptide.

16. A method for selecting and identifying a desired polypeptide having an affinity for a predetermined target from a population of polypeptides, comprising the steps:
   (a) synthesizing each member of a population of polypeptides according to claim 8 on a separate carrier or bead;
   (b) selecting or enriching the carriers or beads based on the interaction of the polypeptide with the predetermined target; and
   (c) identifying the polypeptide by protein characterization methodology.

* * * * *

SEQUENCE LISTING

<160> NUMBER OF SEQ ID NOS: 73

<210> SEQ ID NO 1
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 1

```
Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys Val Asp Gly Ser Leu Ala
    50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105
```

<210> SEQ ID NO 2
<211> LENGTH: 46
<212> TYPE: PRT
<213> ORGANISM: ARTIFICIAL SEQUENCE
<220> FEATURE:
<223> OTHER INFORMATION: Engineered albumin binding polypeptide

<400> SEQUENCE: 2

```
Leu Ala Glu Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 3
<211> LENGTH: 1676
<212> TYPE: PRT
<213> ORGANISM: HOMO SAPIENS

<400> SEQUENCE: 3

```
Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
```

-continued

```
                100                 105                 110
Lys Ser Lys Arg Met Pro Ile Thr Tyr Asp Asn Gly Phe Leu Phe Ile
            115                 120                 125
His Thr Asp Lys Pro Val Tyr Thr Pro Asp Gln Ser Val Lys Val Arg
            130                 135                 140
Val Tyr Ser Leu Asn Asp Asp Leu Lys Pro Ala Lys Arg Glu Thr Val
145                 150                 155                 160
Leu Thr Phe Ile Asp Pro Glu Gly Ser Glu Val Asp Met Val Glu Glu
                165                 170                 175
Ile Asp His Ile Gly Ile Ile Ser Phe Pro Asp Phe Lys Ile Pro Ser
                180                 185                 190
Asn Pro Arg Tyr Gly Met Trp Thr Ile Lys Ala Lys Tyr Lys Glu Asp
                195                 200                 205
Phe Ser Thr Thr Gly Thr Ala Tyr Phe Glu Val Lys Glu Tyr Val Leu
            210                 215                 220
Pro His Phe Ser Val Ser Ile Glu Pro Glu Tyr Asn Phe Ile Gly Tyr
225                 230                 235                 240
Lys Asn Phe Lys Asn Phe Glu Ile Thr Ile Lys Ala Arg Tyr Phe Tyr
                245                 250                 255
Asn Lys Val Val Thr Glu Ala Asp Val Tyr Ile Thr Phe Gly Ile Arg
            260                 265                 270
Glu Asp Leu Lys Asp Asp Gln Lys Glu Met Met Gln Thr Ala Met Gln
            275                 280                 285
Asn Thr Met Leu Ile Asn Gly Ile Ala Gln Val Thr Phe Asp Ser Glu
            290                 295                 300
Thr Ala Val Lys Glu Leu Ser Tyr Tyr Ser Leu Glu Asp Leu Asn Asn
305                 310                 315                 320
Lys Tyr Leu Tyr Ile Ala Val Thr Val Ile Glu Ser Thr Gly Gly Phe
                325                 330                 335
Ser Glu Glu Ala Glu Ile Pro Gly Ile Lys Tyr Val Leu Ser Pro Tyr
            340                 345                 350
Lys Leu Asn Leu Val Ala Thr Pro Leu Phe Leu Lys Pro Gly Ile Pro
            355                 360                 365
Tyr Pro Ile Lys Val Gln Val Lys Asp Ser Leu Asp Gln Leu Val Gly
            370                 375                 380
Gly Val Pro Val Thr Leu Asn Ala Gln Thr Ile Asp Val Asn Gln Glu
385                 390                 395                 400
Thr Ser Asp Leu Asp Pro Ser Lys Ser Val Thr Arg Val Asp Asp Gly
                405                 410                 415
Val Ala Ser Phe Val Leu Asn Leu Pro Ser Gly Val Thr Val Leu Glu
                420                 425                 430
Phe Asn Val Lys Thr Asp Ala Pro Asp Leu Pro Glu Glu Asn Gln Ala
            435                 440                 445
Arg Glu Gly Tyr Arg Ala Ile Ala Tyr Ser Ser Leu Ser Gln Ser Tyr
            450                 455                 460
Leu Tyr Ile Asp Trp Thr Asp Asn His Lys Ala Leu Leu Val Gly Glu
465                 470                 475                 480
His Leu Asn Ile Ile Val Thr Pro Lys Ser Pro Tyr Ile Asp Lys Ile
                485                 490                 495
Thr His Tyr Asn Tyr Leu Ile Leu Ser Lys Gly Lys Ile Ile His Phe
                500                 505                 510
Gly Thr Arg Glu Lys Phe Ser Asp Ala Ser Tyr Gln Ser Ile Asn Ile
            515                 520                 525
```

```
Pro Val Thr Gln Asn Met Val Pro Ser Ser Arg Leu Leu Val Tyr Tyr
    530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Ala Tyr Ser Pro Gly Gln Thr Val Ser Leu Asn Met
                580                 585                 590

Ala Thr Gly Met Asp Ser Trp Val Ala Leu Ala Ala Val Asp Ser Ala
                595                 600                 605

Val Tyr Gly Val Gln Arg Gly Ala Lys Lys Pro Leu Glu Arg Val Phe
    610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
                660                 665                 670

Leu Arg Pro Arg Arg Thr Leu Gln Lys Lys Ile Glu Glu Ile Ala Ala
    675                 680                 685

Lys Tyr Lys His Ser Val Val Lys Lys Cys Cys Tyr Asp Gly Ala Cys
    690                 695                 700

Val Asn Asn Asp Glu Thr Cys Glu Gln Arg Ala Ala Arg Ile Ser Leu
705                 710                 715                 720

Gly Pro Arg Cys Ile Lys Ala Phe Thr Glu Cys Cys Val Val Ala Ser
                725                 730                 735

Gln Leu Arg Ala Asn Ile Ser His Lys Asp Met Gln Leu Gly Arg Leu
                740                 745                 750

His Met Lys Thr Leu Leu Pro Val Ser Lys Pro Glu Ile Arg Ser Tyr
    755                 760                 765

Phe Pro Glu Ser Trp Leu Trp Glu Val His Leu Val Pro Arg Arg Lys
770                 775                 780

Gln Leu Gln Phe Ala Leu Pro Asp Ser Leu Thr Thr Trp Glu Ile Gln
785                 790                 795                 800

Gly Val Gly Ile Ser Asn Thr Gly Ile Cys Val Ala Asp Thr Val Lys
                805                 810                 815

Ala Lys Val Phe Lys Asp Val Phe Leu Glu Met Asn Ile Pro Tyr Ser
                820                 825                 830

Val Val Arg Gly Glu Gln Ile Gln Leu Lys Gly Thr Val Tyr Asn Tyr
    835                 840                 845

Arg Thr Ser Gly Met Gln Phe Cys Val Lys Met Ser Ala Val Glu Gly
    850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser His Leu Val
                885                 890                 895

Thr Phe Thr Val Leu Pro Leu Glu Ile Gly Leu His Asn Ile Asn Phe
                900                 905                 910

Ser Leu Glu Thr Trp Phe Gly Lys Glu Ile Leu Val Lys Thr Leu Arg
                915                 920                 925

Val Val Pro Glu Gly Val Lys Arg Glu Ser Tyr Ser Gly Val Thr Leu
    930                 935                 940
```

-continued

```
Asp Pro Arg Gly Ile Tyr Gly Thr Ile Ser Arg Lys Glu Phe Pro
945                 950                 955                 960

Tyr Arg Ile Pro Leu Asp Leu Val Pro Lys Thr Glu Ile Lys Arg Ile
                965                 970                 975

Leu Ser Val Lys Gly Leu Leu Val Gly Glu Ile Leu Ser Ala Val Leu
            980                 985                 990

Ser Gln Glu Gly Ile Asn Ile Leu Thr His Leu Pro Lys Gly Ser Ala
        995                 1000                1005

Glu Ala Glu Leu Met Ser Val Val Pro Val Phe Tyr Val Phe His
    1010                1015                1020

Tyr Leu Glu Thr Gly Asn His Trp Asn Ile Phe His Ser Asp Pro
    1025                1030                1035

Leu Ile Glu Lys Gln Lys Leu Lys Lys Lys Leu Lys Glu Gly Met
    1040                1045                1050

Leu Ser Ile Met Ser Tyr Arg Asn Ala Asp Tyr Ser Tyr Ser Val
    1055                1060                1065

Trp Lys Gly Gly Ser Ala Ser Thr Trp Leu Thr Ala Phe Ala Leu
    1070                1075                1080

Arg Val Leu Gly Gln Val Asn Lys Tyr Val Glu Gln Asn Gln Asn
    1085                1090                1095

Ser Ile Cys Asn Ser Leu Leu Trp Leu Val Glu Asn Tyr Gln Leu
    1100                1105                1110

Asp Asn Gly Ser Phe Lys Glu Asn Ser Gln Tyr Gln Pro Ile Lys
    1115                1120                1125

Leu Gln Gly Thr Leu Pro Val Glu Ala Arg Glu Asn Ser Leu Tyr
    1130                1135                1140

Leu Thr Ala Phe Thr Val Ile Gly Ile Arg Lys Ala Phe Asp Ile
    1145                1150                1155

Cys Pro Leu Val Lys Ile Asp Thr Ala Leu Ile Lys Ala Asp Asn
    1160                1165                1170

Phe Leu Leu Glu Asn Thr Leu Pro Ala Gln Ser Thr Phe Thr Leu
    1175                1180                1185

Ala Ile Ser Ala Tyr Ala Leu Ser Leu Gly Asp Lys Thr His Pro
    1190                1195                1200

Gln Phe Arg Ser Ile Val Ser Ala Leu Lys Arg Glu Ala Leu Val
    1205                1210                1215

Lys Gly Asn Pro Pro Ile Tyr Arg Phe Trp Lys Asp Asn Leu Gln
    1220                1225                1230

His Lys Asp Ser Ser Val Pro Asn Thr Gly Thr Ala Arg Met Val
    1235                1240                1245

Glu Thr Thr Ala Tyr Ala Leu Leu Thr Ser Leu Asn Leu Lys Asp
    1250                1255                1260

Ile Asn Tyr Val Asn Pro Val Ile Lys Trp Leu Ser Glu Glu Gln
    1265                1270                1275

Arg Tyr Gly Gly Gly Phe Tyr Ser Thr Gln Asp Thr Ile Asn Ala
    1280                1285                1290

Ile Glu Gly Leu Thr Glu Tyr Ser Leu Leu Val Lys Gln Leu Arg
    1295                1300                1305

Leu Ser Met Asp Ile Asp Val Ser Tyr Lys His Lys Gly Ala Leu
    1310                1315                1320

His Asn Tyr Lys Met Thr Asp Lys Asn Phe Leu Gly Arg Pro Val
    1325                1330                1335

Glu Val Leu Leu Asn Asp Asp Leu Ile Val Ser Thr Gly Phe Gly
```

```
                1340                1345                1350
Ser Gly Leu Ala Thr Val His Val Thr Thr Val His Lys Thr
    1355                1360                1365
Ser Thr Ser Glu Glu Val Cys Ser Phe Tyr Leu Lys Ile Asp Thr
    1370                1375                    1380
Gln Asp Ile Glu Ala Ser His Tyr Arg Gly Tyr Gly Asn Ser Asp
    1385                1390                    1395
Tyr Lys Arg Ile Val Ala Cys Ala Ser Tyr Lys Pro Ser Arg Glu
    1400                1405                1410
Glu Ser Ser Gly Ser Ser His Ala Val Met Asp Ile Ser Leu
    1415                1420                1425
Pro Thr Gly Ile Ser Ala Asn Glu Glu Asp Leu Lys Ala Leu Val
    1430                1435                    1440
Glu Gly Val Asp Gln Leu Phe Thr Asp Tyr Gln Ile Lys Asp Gly
    1445                1450                1455
His Val Ile Leu Gln Leu Asn Ser Ile Pro Ser Ser Asp Phe Leu
    1460                1465                    1470
Cys Val Arg Phe Arg Ile Phe Glu Leu Phe Glu Val Gly Phe Leu
    1475                1480                1485
Ser Pro Ala Thr Phe Thr Val Tyr Glu Tyr His Arg Pro Asp Lys
    1490                1495                1500
Gln Cys Thr Met Phe Tyr Ser Thr Ser Asn Ile Lys Ile Gln Lys
    1505                1510                1515
Val Cys Glu Gly Ala Ala Cys Lys Cys Val Glu Ala Asp Cys Gly
    1520                1525                1530
Gln Met Gln Glu Glu Leu Asp Leu Thr Ile Ser Ala Glu Thr Arg
    1535                1540                1545
Lys Gln Thr Ala Cys Lys Pro Glu Ile Ala Tyr Ala Tyr Lys Val
    1550                1555                1560
Ser Ile Thr Ser Ile Thr Val Glu Asn Val Phe Val Lys Tyr Lys
    1565                1570                1575
Ala Thr Leu Leu Asp Ile Tyr Lys Thr Gly Glu Ala Val Ala Glu
    1580                1585                1590
Lys Asp Ser Glu Ile Thr Phe Ile Lys Lys Val Thr Cys Thr Asn
    1595                1600                1605
Ala Glu Leu Val Lys Gly Arg Gln Tyr Leu Ile Met Gly Lys Glu
    1610                1615                1620
Ala Leu Gln Ile Lys Tyr Asn Phe Ser Phe Arg Tyr Ile Tyr Pro
    1625                1630                1635
Leu Asp Ser Leu Thr Trp Ile Glu Tyr Trp Pro Arg Asp Thr Thr
    1640                1645                1650
Cys Ser Ser Cys Gln Ala Phe Leu Ala Asn Leu Asp Glu Phe Ala
    1655                1660                1665
Glu Asp Ile Phe Leu Asn Gly Cys
    1670                1675

<210> SEQ ID NO 4
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 4

Ala Glu Ala Lys Tyr Ala Lys Glu Val Leu Glu Ala Trp Asp Glu Ile
```

```
1               5                   10                  15
Asp Arg Leu Pro Asn Leu Thr Ile Glu Gln Trp Leu Ala Phe Ile Asn
            20                  25                  30

Lys Leu Asp Arg Gln Pro Glu Gln Ser Ser Glu Leu Leu Ser Glu Ala
            35                  40                  45

Lys Lys Leu Asn Asp Ser Gln Ala Pro Lys Val Asp Gly Ser Leu Ala
        50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105

<210> SEQ ID NO 5
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 5

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
            35                  40                  45

Lys Lys Leu Ser Glu Ser Gln Ala Pro Lys Val Asp Gly Ser Leu Ala
        50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105

<210> SEQ ID NO 6
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 6

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys Val Asp Gly Ser Leu Ala
        50                  55                  60

Glu Ala Lys Val Leu Ala Asn Arg Glu Leu Asp Lys Tyr Gly Val Ser
65                  70                  75                  80

Asp Phe Tyr Lys Arg Leu Ile Asn Lys Ala Lys Thr Val Glu Gly Val
                85                  90                  95
```

```
Glu Ala Leu Lys Leu His Ile Leu Ala Ala Leu Pro
            100                 105
```

```
<210> SEQ ID NO 7
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 7

Ala Glu Ala Lys Tyr Ala Lys Glu Val Leu Glu Ala Trp Ser Glu Ile
1               5                   10                  15

Asp Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys Val Asp Gly Ser Leu Ala
    50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105
```

```
<210> SEQ ID NO 8
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 8

Ala Glu Ala Lys Tyr Ala Lys Glu Val Leu Glu Ala Trp Asp Glu Ile
1               5                   10                  15

Glu Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys Val Asp Gly Ser Leu Ala
    50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105
```

```
<210> SEQ ID NO 9
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 9

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Ala
```

```
                    20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys Val Asp Gly Ser Leu Ala
 50                  55                  60

Glu Ala Lys Glu Ala Ala Asn Ala Glu Leu Asp Ser Tyr Gly Val Ser
 65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105

<210> SEQ ID NO 10
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 10

Ala Glu Ala Lys Tyr Ala Lys Glu Val Leu Glu Ala Trp Asp Glu Ile
 1               5                  10                  15

Asp Arg Leu Pro Asn Leu Thr Ile Glu Gln Trp Leu Ala Phe Ile Asn
                20                  25                  30

Lys Leu Glu Asp Asp Pro Ser Gln Ser Ser Glu Leu Leu Ser Glu Ala
            35                  40                  45

Lys Lys Leu Asn Asp Ser Gln Ala Pro Lys Val Asp Gly Ser Leu Ala
 50                  55                  60

Glu Ala Lys Glu Ala Ala Asn Ala Glu Leu Asp Ser Tyr Gly Val Ser
 65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105

<210> SEQ ID NO 11
<211> LENGTH: 103
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 11

Ala Glu Ala Lys Tyr Ala Lys Glu Val Leu Glu Ala Trp Asp Glu Ile
 1               5                  10                  15

Asp Arg Leu Pro Asn Leu Thr Ile Glu Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Leu Ala Glu Lys Glu Ala
 50                  55                  60

Ala Asn Ala Glu Leu Asp Ser Tyr Gly Val Ser Asp Phe Tyr Lys Arg
 65                  70                  75                  80

Leu Ile Asp Lys Ala Lys Thr Val Glu Gly Val Glu Ala Leu Lys Asp
                85                  90                  95

Ala Ile Leu Ala Ala Leu Pro
            100
```

<210> SEQ ID NO 12
<211> LENGTH: 57
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 12

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Ser Glu Ser Gln Ala Pro
        50                  55

<210> SEQ ID NO 13
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 13

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Ser Glu Ser Gln Ala Pro Lys Val Glu Gly Ser Leu Ala
        50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105

<210> SEQ ID NO 14
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 14

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Ser Glu Ser Gln Ala Pro Lys Val Ala Gly Ser Leu Ala
        50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val 85                  90                  95

Glu Ala Leu Lys Asp Ala Ile Leu Ala Ala Leu Pro
            100                 105

<210> SEQ ID NO 15
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 15

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
            35                  40                  45

Lys Lys Leu Glu Ser Ser Gln Ala Pro Lys Val Glu Gly Ser Leu Ala
    50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105

<210> SEQ ID NO 16
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 16

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Arg Gln Pro Glu Gln Ser Ser Glu Leu Leu Ser Glu Ala
            35                  40                  45

Lys Lys Leu Ser Glu Ser Gln Ala Pro Lys Val Glu Gly Ser Leu Ala
    50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105

<210> SEQ ID NO 17
<211> LENGTH: 57
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 17

Ala Glu Ala Lys Tyr Ala Lys Glu Val Leu Glu Ala Trp Asp Glu Ile
1               5                   10                  15

```
Asp Arg Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Glu Ser Ser Gln Ala Pro
    50                  55

<210> SEQ ID NO 18
<211> LENGTH: 57
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 18

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Arg Gln Pro Glu Gln Ser Ser Glu Leu Leu Ser Glu Ala
        35                  40                  45

Lys Lys Leu Ser Glu Ser Gln Ala Pro
    50                  55

<210> SEQ ID NO 19
<211> LENGTH: 48
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 19

Glu Val Leu Glu Ala Trp Asp Glu Ile Asp Arg Leu Pro Asn Leu Thr
1               5                   10                  15

Ile Glu Gln Trp Leu Ala Phe Ile Asn Lys Leu Asp Asp Pro Ser
            20                  25                  30

Gln Ser Ser Glu Leu Leu Ser Glu Ala Lys Lys Leu Ser Glu Ser Gln
        35                  40                  45

<210> SEQ ID NO 20
<211> LENGTH: 48
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 20

Glu Val Leu Glu Ala Trp Asp Glu Ile Asp Arg Leu Pro Asn Leu Thr
1               5                   10                  15

Ile Glu Gln Trp Leu Ala Phe Ile Asn Lys Leu Asp Asp Pro Ser
            20                  25                  30

Gln Ser Ser Glu Leu Leu Ser Glu Ala Lys Lys Leu Glu Ser Ser Gln
        35                  40                  45

<210> SEQ ID NO 21
<211> LENGTH: 48
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 21
```

Glu Val Leu Glu Ala Trp Asp Glu Ile Asp Arg Leu Pro Asn Leu Thr
1               5                   10                  15

Ile Glu Gln Trp Leu Ala Phe Ile Asn Lys Leu Asp Arg Gln Pro Glu
            20                  25                  30

Gln Ser Ser Glu Leu Leu Ser Glu Ala Lys Lys Leu Ser Glu Ser Gln
        35                  40                  45

<210> SEQ ID NO 22
<211> LENGTH: 58
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 22

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 23
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 23

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys Val Gly Ser Leu Ala
    50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105

<210> SEQ ID NO 24
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 24

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

```
Lys Leu Asp Asp Pro Ser Gln Ser Ser Glu Leu Leu Ser Glu Ala
        35                  40                  45
Lys Lys Leu Asn Glu Ser Gln Ala Pro Lys Val Glu Gly Ser Leu Ala
    50                  55                  60
Glu Ala Lys Glu Ala Ala Asn Ala Glu Leu Asp Ser Tyr Gly Val Ser
65                  70                  75                  80
Asp Phe Tyr Lys Arg Leu Ile Asp Lys Ala Lys Thr Val Glu Gly Val
                85                  90                  95
Glu Ala Leu Lys Asp Ala Ile Leu Ala Ala Leu Pro
            100                 105
```

<210> SEQ ID NO 25
<211> LENGTH: 108
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 25

```
Ala Glu Ala Lys Tyr Ala Lys Glu Val Leu Glu Ala Trp Asp Glu Ile
1               5                   10                  15
Asp Arg Leu Pro Asn Leu Thr Ile Glu Gln Trp Leu Ala Phe Ile Asn
                20                  25                  30
Lys Leu Asp Asp Pro Ser Gln Ser Ser Glu Leu Leu Ser Glu Ala
        35                  40                  45
Lys Lys Leu Ser Asp Ser Gln Ala Pro Lys Val Glu Gly Ser Leu Ala
    50                  55                  60
Glu Ala Lys Glu Ala Ala Asn Ala Glu Leu Asp Ser Tyr Gly Val Ser
65                  70                  75                  80
Asp Phe Tyr Lys Arg Leu Ile Asp Lys Ala Lys Thr Val Glu Gly Val
                85                  90                  95
Glu Ala Leu Lys Asp Ala Ile Leu Ala Ala Leu Pro
            100                 105
```

<210> SEQ ID NO 26
<211> LENGTH: 62
<212> TYPE: PRT
<213> ORGANISM: ARTIFICIAL SEQUENCE
<220> FEATURE:
<223> OTHER INFORMATION: Engineered C5 binding Z variant

<400> SEQUENCE: 26

```
Ala Glu Ala Lys Tyr Ala Lys Glu Val Leu Glu Ala Trp Asp

```
                1               5                  10                  15
Ala Leu Leu Pro Asn Leu Thr Asn Gln Gln Lys Arg Ala Phe Ile Arg
                20                  25                  30

Lys Leu Tyr Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 28
<211> LENGTH: 58
<212> TYPE: PRT
<213> ORGANISM: ARTIFICIAL SEQUENCE
<220> FEATURE:
<223> OTHER INFORMATION: Engineered HER2 binding Z variant

<400> SEQUENCE: 28

Ala Glu Ala Lys Tyr Ala Lys Glu Met Arg Asn Ala Tyr Trp Glu Ile
1               5                  10                  15

Ala Leu Leu Pro Asn Leu Thr Asn Gln Gln Lys Arg Ala Phe Ile Arg
                20                  25                  30

Lys Leu Tyr Asp Asp Pro Ser Gln Ser Ser Glu Leu Leu Ser Glu Ala
            35                  40                  45

Lys Lys Leu Ser Glu Ser Gln Ala Pro Lys
        50                  55

<210> SEQ ID NO 29
<211> LENGTH: 58
<212> TYPE: PRT
<213> ORGANISM: ARTIFICIAL SEQUENCE
<220> FEATURE:
<223> OTHER INFORMATION: Engineered HER2 binding Z variant

<400> SEQUENCE: 29

Ala Glu Ala Lys Tyr Ala Lys Glu Met Arg Asn Ala Tyr Trp Glu Ile
1               5                  10                  15

Ala Leu Leu Pro Asn Leu Thr Asn Gln Gln Lys Arg Ala Phe Ile Arg
                20                  25                  30

Lys Leu Tyr Arg Gln Pro Glu Gln Ser Ser Glu Leu Leu Ser Glu Ala
            35                  40                  45

Lys Lys Leu Ser Glu Ser Gln Ala Pro Lys
        50                  55

<210> SEQ ID NO 30
<211> LENGTH: 58
<212> TYPE: PRT
<213> ORGANISM: ARTIFICIAL SEQUENCE
<220> FEATURE:
<223> OTHER INFORMATION: Engineered PDGFRbeta binding Z variant

<400> SEQUENCE: 30

Ala Glu Ala Lys Tyr Ala Lys Glu Leu Ile Glu Ala Ala Ala Glu Ile
1               5                  10                  15

Asp Ala Leu Pro Asn Leu Thr Arg Arg Gln Trp Asn Ala Phe Ile Lys
                20                  25                  30

Lys Leu Val Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 31
```

```
<211> LENGTH: 58
<212> TYPE: PRT
<213> ORGANISM: ARTIFICIAL SEQUENCE
<220> FEATURE:
<223> OTHER INFORMATION: Engineered PDGFRbeta binding Z variant

<400> SEQUENCE: 31

Ala Glu Ala Lys Tyr Ala Lys Glu Leu Ile Glu Ala Ala Ala Glu Ile
 1               5                  10                  15

Asp Ala Leu Pro Asn Leu Thr Arg Arg Gln Trp Asn Ala Phe Ile Lys
            20                  25                  30

Lys Leu Val Asp Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 32
<211> LENGTH: 58
<212> TYPE: PRT
<213> ORGANISM: ARTIFICIAL SEQUENCE
<220> FEATURE:
<223> OTHER INFORMATION: Engineered PDGFRbeta binding Z variant

<400> SEQUENCE: 32

Ala Glu Ala Lys Tyr Ala Lys Glu Leu Ile Glu Ala Ala Ala Glu Ile
 1               5                  10                  15

Asp Ala Leu Pro Asn Leu Thr Arg Arg Gln Trp Asn Ala Phe Ile Lys
            20                  25                  30

Lys Leu Val Arg Gln Pro Glu Gln Ser Ser Glu Leu Leu Ser Glu Ala
        35                  40                  45

Lys Lys Leu Ser Glu Ser Gln Ala Pro Lys
    50                  55

<210> SEQ ID NO 33
<211> LENGTH: 58
<212> TYPE: PRT
<213> ORGANISM: ARTIFICIAL SEQUENCE
<220> FEATURE:
<223> OTHER INFORMATION: Engineered FcRn binding Z variant

<400> SEQUENCE: 33

Ala Glu Ala Lys Tyr Ala Lys Glu Gln Asp Ala Ala Ala His Glu Ile
 1               5                  10                  15

Arg Trp Leu Pro Asn Leu Thr Phe Asp Gln Arg Val Ala Phe Ile His
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 34
<211> LENGTH: 58
<212> TYPE: PRT
<213> ORGANISM: ARTIFICIAL SEQUENCE
<220> FEATURE:
<223> OTHER INFORMATION: Engineered FcRn binding Z variant

<400> SEQUENCE: 34

Ala Glu Ala Lys Tyr Ala Lys Glu Gln Asp Ala Ala Ala His Glu Ile
 1               5                  10                  15

Arg Trp Leu Pro Asn Leu Thr Phe Asp Gln Arg Val Ala Phe Ile His
            20                  25                  30
```

```
Lys Leu Ala Asp Asp Pro Ser Gln Ser Ser Glu Leu Ser Glu Ala
        35                  40                  45
Lys Lys Leu Ser Glu Ser Gln Ala Pro Lys
    50                  55
```

<210> SEQ ID NO 35
<211> LENGTH: 58
<212> TYPE: PRT
<213> ORGANISM: ARTIFICIAL SEQUENCE
<220> FEATURE:
<223> OTHER INFORMATION: Engineered FcRn binding Z variant

<400> SEQUENCE: 35

```
Ala Glu Ala Lys Tyr Ala Lys Glu Gln Asp Ala Ala His Glu Ile
1               5                   10                  15
Arg Trp Leu Pro Asn Leu Thr Phe Asp Gln Arg Val Ala Phe Ile His
            20                  25                  30
Lys Leu Ala Arg Gln Pro Glu Gln Ser Ser Glu Leu Ser Glu Ala
        35                  40                  45
Lys Lys Leu Ser Glu Ser Gln Ala Pro Lys
    50                  55
```

<210> SEQ ID NO 36
<211> LENGTH: 58
<212> TYPE: PRT
<213> ORGANISM: ARTIFICIAL SEQUENCE
<220> FEATURE:
<223> OTHER INFORMATION: Engineered CAIX binding Z variant

<400> SEQUENCE: 36

```
Ala Glu Ala Lys Tyr Ala Lys Glu Asn Leu Phe Ala Gly Trp Glu Ile
1               5                   10                  15
Ser Asp Leu Pro Asn Leu Thr Asp Tyr Gln Arg Asn Ala Phe Ile Tyr
            20                  25                  30
Lys Leu Trp Asp Asp Pro Ser Gln Ser Ser Glu Leu Ser Glu Ala
        35                  40                  45
Lys Lys Leu Asn Asp Ser Gln Ala Pro Lys
    50                  55
```

<210> SEQ ID NO 37
<211> LENGTH: 58
<212> TYPE: PRT
<213> ORGANISM: ARTIFICIAL SEQUENCE
<220> FEATURE:
<223> OTHER INFORMATION: Engineered CAIX binding Z variant

<400> SEQUENCE: 37

```
Ala Glu Ala Lys Tyr Ala Lys Glu Asn Leu Phe Ala Gly Trp Glu Ile
1               5                   10                  15
Ser Asp Leu Pro Asn Leu Thr Asp Tyr Gln Arg Asn Ala Phe Ile Tyr
            20                  25                  30
Lys Leu Trp Asp Asp Pro Ser Gln Ser Ser Glu Leu Ser Glu Ala
        35                  40                  45
Lys Lys Leu Ser Glu Ser Gln Ala Pro Lys
    50                  55
```

<210> SEQ ID NO 38
<211> LENGTH: 58
<212> TYPE: PRT
<213> ORGANISM: ARTIFICIAL SEQUENCE
<220> FEATURE:

<223> OTHER INFORMATION: Engineered CAIX binding Z variant

<400> SEQUENCE: 38

```
Ala Glu Ala Lys Tyr Ala Lys Glu Asn Leu Phe Ala Gly Trp Glu Ile
1               5                   10                  15

Ser Asp Leu Pro Asn Leu Thr Asp Tyr Gln Arg Asn Ala Phe Ile Tyr
            20                  25                  30

Lys Leu Trp Arg Gln Pro Glu Gln Ser Ser Glu Leu Leu Ser Glu Ala
        35                  40                  45

Lys Lys Leu Ser Glu Ser Gln Ala Pro Lys
    50                  55
```

<210> SEQ ID NO 39
<211> LENGTH: 58
<212> TYPE: PRT
<213> ORGANISM: ARTIFICIAL SEQUENCE
<220> FEATURE:
<223> OTHER INFORMATION: Engineered CAIX binding Z variant

<400> SEQUENCE: 39

```
Ala Glu Ala Lys Tyr Ala Lys Glu Asn Leu Phe Ala Gly Trp Glu Ile
1               5                   10                  15

Ser Asp Leu Pro Asn Leu Thr Asp Tyr Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Glu Ser Gln Ala Pro Lys
    50                  55
```

<210> SEQ ID NO 40
<211> LENGTH: 58
<212> TYPE: PRT
<213> ORGANISM: ARTIFICIAL SEQUENCE
<220> FEATURE:
<223> OTHER INFORMATION: Engineered CAIX binding Z variant

<400> SEQUENCE: 40

```
Ala Glu Ala Lys Tyr Ala Lys Glu Asn Leu Phe Ala Gly Trp Glu Ile
1               5                   10                  15

Ser Asp Leu Pro Asn Leu Thr Asp Tyr Gln Arg Asn Ala Phe Ile Tyr
            20                  25                  30

Lys Leu Trp Arg Gln Pro Glu Gln Ser Ser Glu Leu Leu Ser Glu Ala
        35                  40                  45

Lys Lys Leu Asn Glu Ser Gln Ala Pro Lys
    50                  55
```

<210> SEQ ID NO 41
<211> LENGTH: 58
<212> TYPE: PRT
<213> ORGANISM: ARTIFICIAL SEQUENCE
<220> FEATURE:
<223> OTHER INFORMATION: Engineered CAIX binding Z variant

<400> SEQUENCE: 41

```
Ala Glu Ala Lys Tyr Ala Lys Glu Asn Leu Phe Ala Gly Trp Glu Ile
1               5                   10                  15

Ser Asp Leu Pro Asn Leu Thr Asp Tyr Gln Arg Asn Ala Phe Ile Tyr
            20                  25                  30

Lys Leu Trp Asp Asp Pro Ser Gln Ser Ser Glu Leu Leu Ser Glu Ala
        35                  40                  45
```

```
Lys Lys Leu Ser Asp Ser Gln Ala Pro Lys
        50                  55

<210> SEQ ID NO 42
<211> LENGTH: 58
<212> TYPE: PRT
<213> ORGANISM: ARTIFICIAL SEQUENCE
<220> FEATURE:
<223> OTHER INFORMATION: Engineered CAIX binding Z variant

<400> SEQUENCE: 42

Ala Glu Ala Lys Tyr Ala Lys Glu Asn Leu Phe Ala Gly Trp Glu Ile
1               5                   10                  15

Ser Asp Leu Pro Asn Leu Thr Asp Tyr Gln Arg Asn Ala Phe Ile Tyr
            20                  25                  30

Lys Leu Trp Arg Gln Pro Glu Gln Ser Ser Glu Leu Leu Ser Glu Ala
        35                  40                  45

Lys Lys Leu Ser Asp Ser Gln Ala Pro Lys
        50                  55

<210> SEQ ID NO 43
<211> LENGTH: 48
<212> TYPE: PRT
<213> ORGANISM: ARTIFICIAL SEQUENCE
<220> FEATURE:
<223> OTHER INFORMATION: Engineered HER2 binding Z variant

<400> SEQUENCE: 43

Glu Met Arg Asn Ala Tyr Trp Glu Ile Ala Leu Leu Pro Asn Leu Thr
1               5                   10                  15

Asn Gln Gln Lys Arg Ala Phe Ile Arg Lys Leu Tyr Asp Asp Pro Ser
            20                  25                  30

Gln Ser Ser Glu Leu Leu Ser Glu Ala Lys Lys Leu Ser Glu Ser Gln
        35                  40                  45

<210> SEQ ID NO 44
<211> LENGTH: 48
<212> TYPE: PRT
<213> ORGANISM: ARTIFICIAL SEQUENCE
<220> FEATURE:
<223> OTHER INFORMATION: Engineered HER2 binding Z variant

<400> SEQUENCE: 44

Glu Met Arg Asn Ala Tyr Trp Glu Ile Ala Leu Leu Pro Asn Leu Thr
1               5                   10                  15

Asn Gln Gln Lys Arg Ala Phe Ile Arg Lys Leu Tyr Arg Gln Pro Glu
            20                  25                  30

Gln Ser Ser Glu Leu Leu Ser Glu Ala Lys Lys Leu Ser Glu Ser Gln
        35                  40                  45

<210> SEQ ID NO 45
<211> LENGTH: 48
<212> TYPE: PRT
<213> ORGANISM: ARTIFICIAL SEQUENCE
<220> FEATURE:
<223> OTHER INFORMATION: Engineered PDGFRbeta binding Z variant

<400> SEQUENCE: 45

Glu Leu Ile Glu Ala Ala Ala Glu Ile Asp Ala Leu Pro Asn Leu Thr
1               5                   10                  15

Arg Arg Gln Trp Asn Ala Phe Ile Lys Lys Leu Val Asp Asp Pro Ser
            20                  25                  30
```

-continued

Gln Ser Ser Glu Leu Leu Ser Glu Ala Lys Lys Leu Ser Glu Ser Gln
        35                  40                  45

<210> SEQ ID NO 46
<211> LENGTH: 48
<212> TYPE: PRT
<213> ORGANISM: ARTIFICIAL SEQUENCE
<220> FEATURE:
<223> OTHER INFORMATION: Engineered PDGFRbeta binding Z variant

<400> SEQUENCE: 46

Glu Leu Ile Glu Ala Ala Ala Glu Ile Asp Ala Leu Pro Asn Leu Thr
1               5                   10                  15

Arg Arg Gln Trp Asn Ala Phe Ile Lys Lys Leu Val Arg Gln Pro Glu
            20                  25                  30

Gln Ser Ser Glu Leu Leu Ser Glu Ala Lys Lys Leu Ser Glu Ser Gln
        35                  40                  45

<210> SEQ ID NO 47
<211> LENGTH: 48
<212> TYPE: PRT
<213> ORGANISM: ARTIFICIAL SEQUENCE
<220> FEATURE:
<223> OTHER INFORMATION: Engineered FcRn binding Z variant

<400> SEQUENCE: 47

Glu Gln Asp Ala Ala Ala His Glu Ile Arg Trp Leu Pro Asn Leu Thr
1               5                   10                  15

Phe Asp Gln Arg Val Ala Phe Ile His Lys Leu Ala Asp Asp Pro Ser
            20                  25                  30

Gln Ser Ser Glu Leu Leu Ser Glu Ala Lys Lys Leu Ser Glu Ser Gln
        35                  40                  45

<210> SEQ ID NO 48
<211> LENGTH: 48
<212> TYPE: PRT
<213> ORGANISM: ARTIFICIAL SEQUENCE
<220> FEATURE:
<223> OTHER INFORMATION: Engineered FcRn binding Z variant

<400> SEQUENCE: 48

Glu Gln Asp Ala Ala Ala His Glu Ile Arg Trp Leu Pro Asn Leu Thr
1               5                   10                  15

Phe Asp Gln Arg Val Ala Phe Ile His Lys Leu Ala Arg Gln Pro Glu
            20                  25                  30

Gln Ser Ser Glu Leu Leu Ser Glu Ala Lys Lys Leu Ser Glu Ser Gln
        35                  40                  45

<210> SEQ ID NO 49
<211> LENGTH: 48
<212> TYPE: PRT
<213> ORGANISM: ARTIFICIAL SEQUENCE
<220> FEATURE:
<223> OTHER INFORMATION: Engineered CAIX binding Z variant

<400> SEQUENCE: 49

Glu Asn Leu Phe Ala Gly Trp Glu Ile Ser Asp Leu Pro Asn Leu Thr
1               5                   10                  15

Asp Tyr Gln Arg Asn Ala Phe Ile Tyr Lys Leu Trp Asp Asp Pro Ser
            20                  25                  30

Gln Ser Ser Glu Leu Leu Ser Glu Ala Lys Lys Leu Ser Glu Ser Gln
        35                  40                  45

<210> SEQ ID NO 50
<211> LENGTH: 48
<212> TYPE: PRT
<213> ORGANISM: ARTIFICIAL SEQUENCE
<220> FEATURE:
<223> OTHER INFORMATION: Engineered CAIX binding Z variant

<400> SEQUENCE: 50

Glu Asn Leu Phe Ala Gly Trp Glu Ile Ser Asp Leu Pro Asn Leu Thr
1               5                   10                  15

Asp Tyr Gln Arg Asn Ala Phe Ile Tyr Lys Leu Trp Arg Gln Pro Glu
            20                  25                  30

Gln Ser Ser Glu Leu Leu Ser Glu Ala Lys Lys Leu Glu Ser Gln
        35                  40                  45

<210> SEQ ID NO 51
<211> LENGTH: 48
<212> TYPE: PRT
<213> ORGANISM: ARTIFICIAL SEQUENCE
<220> FEATURE:
<223> OTHER INFORMATION: Engineered CAIX binding Z variant

<400> SEQUENCE: 51

Glu Asn Leu Phe Ala Gly Trp Glu Ile Ser Asp Leu Pro Asn Leu Thr
1               5                   10                  15

Asp Tyr Gln Arg Asn Ala Phe Ile Tyr Lys Leu Trp Asp Asp Pro Ser
            20                  25                  30

Gln Ser Ser Glu Leu Leu Ser Glu Ala Lys Lys Leu Asn Glu Ser Gln
        35                  40                  45

<210> SEQ ID NO 52
<211> LENGTH: 48
<212> TYPE: PRT
<213> ORGANISM: ARTIFICIAL SEQUENCE
<220> FEATURE:
<223> OTHER INFORMATION: Engineered CAIX binding Z variant

<400> SEQUENCE: 52

Glu Asn Leu Phe Ala Gly Trp Glu Ile Ser Asp Leu Pro Asn Leu Thr
1               5                   10                  15

Asp Tyr Gln Arg Asn Ala Phe Ile Tyr Lys Leu Trp Arg Gln Pro Glu
            20                  25                  30

Gln Ser Ser Glu Leu Leu Ser Glu Ala Lys Lys Leu Asn Glu Ser Gln
        35                  40                  45

<210> SEQ ID NO 53
<211> LENGTH: 48
<212> TYPE: PRT
<213> ORGANISM: ARTIFICIAL SEQUENCE
<220> FEATURE:
<223> OTHER INFORMATION: Engineered CAIX binding Z variant

<400> SEQUENCE: 53

Glu Asn Leu Phe Ala Gly Trp Glu Ile Ser Asp Leu Pro Asn Leu Thr
1               5                   10                  15

Asp Tyr Gln Arg Asn Ala Phe Ile Tyr Lys Leu Trp Asp Asp Pro Ser
            20                  25                  30

Gln Ser Ser Glu Leu Leu Ser Glu Ala Lys Lys Leu Ser Asp Ser Gln
        35                  40                  45

<210> SEQ ID NO 54
<211> LENGTH: 48

<212> TYPE: PRT
<213> ORGANISM: ARTIFICIAL SEQUENCE
<220> FEATURE:
<223> OTHER INFORMATION: Engineered CAIX binding Z variant

<400> SEQUENCE: 54

Glu Asn Leu Phe Ala Gly Trp Glu Ile Ser Asp Leu Pro Asn Leu Thr
1               5                   10                  15

Asp Tyr Gln Arg Asn Ala Phe Ile Tyr Lys Leu Trp Arg Gln Pro Glu
            20                  25                  30

Gln Ser Ser Glu Leu Leu Ser Glu Ala Lys Lys Leu Ser Asp Ser Gln
        35                  40                  45

<210> SEQ ID NO 55
<211> LENGTH: 48
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (2)..(2)
<223> OTHER INFORMATION: Xaa is selected from any amino acid residue
<220> FEATURE:
<221> NAME/KEY: MISC_FEATURE
<222> LOCATION: (3)..(3)
<223> OTHER INFORMATION: Xaa is selected from any amino acid residue
<220> FEATURE:
<221> NAME/KEY: MISC_FEATURE
<222> LOCATION: (4)..(4)
<223> OTHER INFORMATION: Xaa is selected from any amino acid residue
<220> FEATURE:
<221> NAME/KEY: MISC_FEATURE
<222> LOCATION: (6)..(6)
<223> OTHER INFORMATION: Xaa is selected from any amino acid residue
<220> FEATURE:
<221> NAME/KEY: MISC_FEATURE
<222> LOCATION: (7)..(7)
<223> OTHER INFORMATION: Xaa is selected from any amino acid residue
<220> FEATURE:
<221> NAME/KEY: MISC_FEATURE
<222> LOCATION: (10)..(10)
<223> OTHER INFORMATION: Xaa is selected from any amino acid residue
<220> FEATURE:
<221> NAME/KEY: MISC_FEATURE
<222> LOCATION: (11)..(11)
<223> OTHER INFORMATION: Xaa is selected from any amino acid residue
<220> FEATURE:
<221> NAME/KEY: MISC_FEATURE
<222> LOCATION: (16)..(16)
<223> OTHER INFORMATION: Xaa is selected from N and T
<220> FEATURE:
<221> NAME/KEY: MISC_FEATURE
<222> LOCATION: (17)..(17)
<223> OTHER INFORMATION: Xaa is selected from any amino acid residue
<220> FEATURE:
<221> NAME/KEY: MISC_FEATURE
<222> LOCATION: (18)..(18)
<223> OTHER INFORMATION: Xaa is selected from any amino acid residue
<220> FEATURE:
<221> NAME/KEY: MISC_FEATURE
<222> LOCATION: (20)..(20)
<223> OTHER INFORMATION: Xaa is selected from any amino acid residue
<220> FEATURE:
<221> NAME/KEY: MISC_FEATURE
<222> LOCATION: (21)..(21)
<223> OTHER INFORMATION: Xaa is selected from any amino acid residue
<220> FEATURE:
<221> NAME/KEY: MISC_FEATURE
<222> LOCATION: (25)..(25)
<223> OTHER INFORMATION: Xaa is selected from any amino acid residue
<220> FEATURE:
<221> NAME/KEY: MISC_FEATURE
<222> LOCATION: (26)..(26)
<223> OTHER INFORMATION: Xaa is selected from K and S

```
<220> FEATURE:
<221> NAME/KEY: MISC_FEATURE
<222> LOCATION: (28)..(28)
<223> OTHER INFORMATION: Xaa is selected from any amino acid residue
<220> FEATURE:
<221> NAME/KEY: MISC_FEATURE
<222> LOCATION: (29)..(32)
<223> OTHER INFORMATION: XaaXaaProXaa is selected from DDPS and RQPE
<220> FEATURE:
<221> NAME/KEY: MISC_FEATURE
<222> LOCATION: (35)..(35)
<223> OTHER INFORMATION: Xaa is selected from A and S
<220> FEATURE:
<221> NAME/KEY: MISC_FEATURE
<222> LOCATION: (36)..(36)
<223> OTHER INFORMATION: Xaa is selected from E and N
<220> FEATURE:
<221> NAME/KEY: MISC_FEATURE
<222> LOCATION: (39)..(39)
<223> OTHER INFORMATION: Xaa is selected from A, C, and S
<220> FEATURE:
<221> NAME/KEY: MISC_FEATURE
<222> LOCATION: (45)..(45)
<223> OTHER INFORMATION: Xaa is selected from E, N, and S
<220> FEATURE:
<221> NAME/KEY: MISC_FEATURE
<222> LOCATION: (46)..(46)
<223> OTHER INFORMATION: Xaa is selected from D, E, and S
<220> FEATURE:
<221> NAME/KEY: MISC_FEATURE
<222> LOCATION: (47)..(47)
<223> OTHER INFORMATION: Xaa is selected from A and S

<400> SEQUENCE: 55

Glu Xaa Xaa Xaa Ala Xaa Xaa Glu Ile Xaa Xaa Leu Pro Asn Leu Xaa
1               5                   10                  15

Xaa Xaa Gln Xaa Xaa Ala Phe Ile Xaa Xaa Leu Xaa Xaa Xaa Pro Xaa
            20                  25                  30

Gln Ser Xaa Xaa Leu Leu Xaa Glu Ala Lys Lys Leu Xaa Xaa Xaa Gln
        35                  40                  45

<210> SEQ ID NO 56
<211> LENGTH: 53
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (5)..(5)
<223> OTHER INFORMATION: Xaa is selected from any amino acid residue
<220> FEATURE:
<221> NAME/KEY: MISC_FEATURE
<222> LOCATION: (6)..(6)
<223> OTHER INFORMATION: Xaa is selected from any amino acid residue
<220> FEATURE:
<221> NAME/KEY: MISC_FEATURE
<222> LOCATION: (7)..(7)
<223> OTHER INFORMATION: Xaa is selected from any amino acid residue
<220> FEATURE:
<221> NAME/KEY: MISC_FEATURE
<222> LOCATION: (9)..(9)
<223> OTHER INFORMATION: Xaa is selected from any amino acid residue
<220> FEATURE:
<221> NAME/KEY: MISC_FEATURE
<222> LOCATION: (10)..(10)
<223> OTHER INFORMATION: Xaa is selected from any amino acid residue
<220> FEATURE:
<221> NAME/KEY: MISC_FEATURE
<222> LOCATION: (13)..(13)
<223> OTHER INFORMATION: Xaa is selected from any amino acid residue
<220> FEATURE:
<221> NAME/KEY: MISC_FEATURE
<222> LOCATION: (14)..(14)
<223> OTHER INFORMATION: Xaa is selected from any amino acid residue
```

-continued

```
<220> FEATURE:
<221> NAME/KEY: MISC_FEATURE
<222> LOCATION: (19)..(19)
<223> OTHER INFORMATION: Xaa is selected from N and T
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: MISC_FEATURE
<222> LOCATION: (21)..(21)
<223> OTHER INFORMATION: Xaa is selected from any amino acid residue
<220> FEATURE:
<221> NAME/KEY: MISC_FEATURE
<222> LOCATION: (23)..(23)
<223> OTHER INFORMATION: Xaa is selected from any amino acid residue
<220> FEATURE:
<221> NAME/KEY: MISC_FEATURE
<222> LOCATION: (24)..(24)
<223> OTHER INFORMATION: Xaa is selected from any amino acid residue
<220> FEATURE:
<221> NAME/KEY: MISC_FEATURE
<222> LOCATION: (28)..(28)
<223> OTHER INFORMATION: Xaa is selected from any amino acid residue
<220> FEATURE:
<221> NAME/KEY: MISC_FEATURE
<222> LOCATION: (29)..(29)
<223> OTHER INFORMATION: Xaa is selected from K and S
<220> FEATURE:
<221> NAME/KEY: MISC_FEATURE
<222> LOCATION: (31)..(31)
<223> OTHER INFORMATION: Xaa is selected from any amino acid residue
<220> FEATURE:
<221> NAME/KEY: MISC_FEATURE
<222> LOCATION: (32)..(35)
<223> OTHER INFORMATION: XaaXaaProXaa is selected from DDPS and RQPE
<220> FEATURE:
<221> NAME/KEY: MISC_FEATURE
<222> LOCATION: (38)..(38)
<223> OTHER INFORMATION: Xaa is selected from A and S
<220> FEATURE:
<221> NAME/KEY: MISC_FEATURE
<222> LOCATION: (39)..(39)
<223> OTHER INFORMATION: Xaa is selected from E and N
<220> FEATURE:
<221> NAME/KEY: MISC_FEATURE
<222> LOCATION: (42)..(42)
<223> OTHER INFORMATION: Xaa is selected from A, C, and S
<220> FEATURE:
<221> NAME/KEY: MISC_FEATURE
<222> LOCATION: (48)..(48)
<223> OTHER INFORMATION: Xaa is selected from E, N, and S
<220> FEATURE:
<221> NAME/KEY: MISC_FEATURE
<222> LOCATION: (49)..(49)
<223> OTHER INFORMATION: Xaa is selected from D, E, and S
<220> FEATURE:
<221> NAME/KEY: MISC_FEATURE
<222> LOCATION: (50)..(50)
<223> OTHER INFORMATION: Xaa is selected from A and S

<400> SEQUENCE: 56

Tyr Ala Lys Glu Xaa Xaa Xaa Ala Xaa Xaa Glu Ile Xaa Xaa Leu Pro
1               5                   10                  15

Asn Leu Xaa Xaa Xaa Gln Xaa Xaa Ala Phe Ile Xaa Xaa Leu Xaa Xaa
            20                  25                  30

Xaa Pro Xaa Gln Ser Xaa Xaa Leu Leu Xaa Glu Ala Lys Lys Leu Xaa
        35                  40                  45

Xaa Xaa Gln Ala Pro
    50

<210> SEQ ID NO 57
<211> LENGTH: 53
<212> TYPE: PRT
```

<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (5)..(5)
<223> OTHER INFORMATION: Xaa is selected from any amino acid residue
<220> FEATURE:
<221> NAME/KEY: MISC_FEATURE
<222> LOCATION: (6)..(6)
<223> OTHER INFORMATION: Xaa is selected from any amino acid residue
<220> FEATURE:
<221> NAME/KEY: MISC_FEATURE
<222> LOCATION: (7)..(7)
<223> OTHER INFORMATION: Xaa is selected from any amino acid residue
<220> FEATURE:
<221> NAME/KEY: MISC_FEATURE
<222> LOCATION: (9)..(9)
<223> OTHER INFORMATION: Xaa is selected from any amino acid residue
<220> FEATURE:
<221> NAME/KEY: MISC_FEATURE
<222> LOCATION: (10)..(10)
<223> OTHER INFORMATION: Xaa is selected from any amino acid residue
<220> FEATURE:
<221> NAME/KEY: MISC_FEATURE
<222> LOCATION: (13)..(13)
<223> OTHER INFORMATION: Xaa is selected from any amino acid residue
<220> FEATURE:
<221> NAME/KEY: MISC_FEATURE
<222> LOCATION: (14)..(14)
<223> OTHER INFORMATION: Xaa is selected from any amino acid residue
<220> FEATURE:
<221> NAME/KEY: MISC_FEATURE
<222> LOCATION: (19)..(19)
<223> OTHER INFORMATION: Xaa is selected from N and T
<220> FEATURE:
<221> NAME/KEY: MISC_FEATURE
<222> LOCATION: (20)..(20)
<223> OTHER INFORMATION: Xaa is selected from any amino acid residue
<220> FEATURE:
<221> NAME/KEY: MISC_FEATURE
<222> LOCATION: (21)..(21)
<223> OTHER INFORMATION: Xaa is selected from any amino acid residue
<220> FEATURE:
<221> NAME/KEY: MISC_FEATURE
<222> LOCATION: (23)..(23)
<223> OTHER INFORMATION: Xaa is selected from any amino acid residue
<220> FEATURE:
<221> NAME/KEY: MISC_FEATURE
<222> LOCATION: (24)..(24)
<223> OTHER INFORMATION: Xaa is selected from any amino acid residue
<220> FEATURE:
<221> NAME/KEY: MISC_FEATURE
<222> LOCATION: (28)..(28)
<223> OTHER INFORMATION: Xaa is selected from any amino acid residue
<220> FEATURE:
<221> NAME/KEY: MISC_FEATURE
<222> LOCATION: (29)..(29)
<223> OTHER INFORMATION: Xaa is selected from K and S
<220> FEATURE:
<221> NAME/KEY: MISC_FEATURE
<222> LOCATION: (31)..(31)
<223> OTHER INFORMATION: Xaa is selected from any amino acid residue
<220> FEATURE:
<221> NAME/KEY: MISC_FEATURE
<222> LOCATION: (32)..(35)
<223> OTHER INFORMATION: XaaXaaProXaa is selected from DDPS and RQPE
<220> FEATURE:
<221> NAME/KEY: MISC_FEATURE
<222> LOCATION: (38)..(38)
<223> OTHER INFORMATION: Xaa is selected from A and S
<220> FEATURE:
<221> NAME/KEY: MISC_FEATURE
<222> LOCATION: (39)..(39)
<223> OTHER INFORMATION: Xaa is selected from E and N
<220> FEATURE:
<221> NAME/KEY: MISC_FEATURE
<222> LOCATION: (42)..(42)
<223> OTHER INFORMATION: Xaa is selected from A, C, and S

```
<220> FEATURE:
<221> NAME/KEY: MISC_FEATURE
<222> LOCATION: (48)..(48)
<223> OTHER INFORMATION: Xaa is selected from E, N, and S
<220> FEATURE:
<221> NAME/KEY: MISC_FEATURE
<222> LOCATION: (49)..(49)
<223> OTHER INFORMATION: Xaa is selected from D, E, and S
<220> FEATURE:
<221> NAME/KEY: MISC_FEATURE
<222> LOCATION: (50)..(50)
<223> OTHER INFORMATION: Xaa is selected from A and S

<400> SEQUENCE: 57

Phe Asn Lys Glu Xaa Xaa Xaa Ala Xaa Xaa Glu Ile Xaa Xaa Leu Pro
1               5                  10                  15

Asn Leu Xaa Xaa Xaa Gln Xaa Xaa Ala Phe Ile Xaa Xaa Leu Xaa Xaa
            20                  25                  30

Xaa Pro Xaa Gln Ser Xaa Xaa Leu Leu Xaa Glu Ala Lys Lys Leu Xaa
        35                  40                  45

Xaa Xaa Gln Ala Pro
    50

<210> SEQ ID NO 58
<211> LENGTH: 58
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (9)..(9)
<223> OTHER INFORMATION: Xaa is selected from any amino acid residue
<220> FEATURE:
<221> NAME/KEY: MISC_FEATURE
<222> LOCATION: (10)..(10)
<223> OTHER INFORMATION: Xaa is selected from any amino acid residue
<220> FEATURE:
<221> NAME/KEY: MISC_FEATURE
<222> LOCATION: (11)..(11)
<223> OTHER INFORMATION: Xaa is selected from any amino acid residue
<220> FEATURE:
<221> NAME/KEY: MISC_FEATURE
<222> LOCATION: (13)..(13)
<223> OTHER INFORMATION: Xaa is selected from any amino acid residue
<220> FEATURE:
<221> NAME/KEY: MISC_FEATURE
<222> LOCATION: (14)..(14)
<223> OTHER INFORMATION: Xaa is selected from any amino acid residue
<220> FEATURE:
<221> NAME/KEY: MISC_FEATURE
<222> LOCATION: (17)..(17)
<223> OTHER INFORMATION: Xaa is selected from any amino acid residue
<220> FEATURE:
<221> NAME/KEY: MISC_FEATURE
<222> LOCATION: (18)..(18)
<223> OTHER INFORMATION: Xaa is selected from any amino acid residue
<220> FEATURE:
<221> NAME/KEY: MISC_FEATURE
<222> LOCATION: (23)..(23)
<223> OTHER INFORMATION: Xaa is selected from N and T
<220> FEATURE:
<221> NAME/KEY: MISC_FEATURE
<222> LOCATION: (24)..(24)
<223> OTHER INFORMATION: Xaa is selected from any amino acid residue
<220> FEATURE:
<221> NAME/KEY: MISC_FEATURE
<222> LOCATION: (25)..(25)
<223> OTHER INFORMATION: Xaa is selected from any amino acid residue
<220> FEATURE:
<221> NAME/KEY: MISC_FEATURE
<222> LOCATION: (27)..(27)
<223> OTHER INFORMATION: Xaa is selected from any amino acid residue
<220> FEATURE:
```

```
<221> NAME/KEY: MISC_FEATURE
<222> LOCATION: (28)..(28)
<223> OTHER INFORMATION: Xaa is selected from any amino acid residue
<220> FEATURE:
<221> NAME/KEY: MISC_FEATURE
<222> LOCATION: (32)..(32)
<223> OTHER INFORMATION: Xaa is selected from any amino acid residue
<220> FEATURE:
<221> NAME/KEY: MISC_FEATURE
<222> LOCATION: (33)..(33)
<223> OTHER INFORMATION: Xaa is selected from K and S
<220> FEATURE:
<221> NAME/KEY: MISC_FEATURE
<222> LOCATION: (35)..(35)
<223> OTHER INFORMATION: Xaa is selected from any amino acid residue
<220> FEATURE:
<221> NAME/KEY: MISC_FEATURE
<222> LOCATION: (36)..(39)
<223> OTHER INFORMATION: XaaXaaProXaa is selected from DDPS and RQPE
<220> FEATURE:
<221> NAME/KEY: MISC_FEATURE
<222> LOCATION: (42)..(42)
<223> OTHER INFORMATION: Xaa is selected from A and S
<220> FEATURE:
<221> NAME/KEY: MISC_FEATURE
<222> LOCATION: (43)..(43)
<223> OTHER INFORMATION: Xaa is selected from E and N
<220> FEATURE:
<221> NAME/KEY: MISC_FEATURE
<222> LOCATION: (46)..(46)
<223> OTHER INFORMATION: Xaa is selected from A, C, and S
<220> FEATURE:
<221> NAME/KEY: MISC_FEATURE
<222> LOCATION: (52)..(52)
<223> OTHER INFORMATION: Xaa is selected from E, N, and S
<220> FEATURE:
<221> NAME/KEY: MISC_FEATURE
<222> LOCATION: (53)..(53)
<223> OTHER INFORMATION: Xaa is selected from D, E, and S
<220> FEATURE:
<221> NAME/KEY: MISC_FEATURE
<222> LOCATION: (54)..(54)
<223> OTHER INFORMATION: Xaa is selected from A and S

<400> SEQUENCE: 58

Ala Asp Asn Asn Phe Asn Lys Glu Xaa Xaa Xaa Ala Xaa Xaa Glu Ile
1               5                   10                  15

Xaa Xaa Leu Pro Asn Leu Xaa Xaa Xaa Gln Xaa Xaa Ala Phe Ile Xaa
            20                  25                  30

Xaa Leu Xaa Xaa Xaa Pro Xaa Gln Ser Xaa Xaa Leu Leu Xaa Glu Ala
        35                  40                  45

Lys Lys Leu Xaa Xaa Xaa Gln Ala Pro Lys
    50                  55

<210> SEQ ID NO 59
<211> LENGTH: 58
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (9)..(9)
<223> OTHER INFORMATION: Xaa is selected from any amino acid residue
<220> FEATURE:
<221> NAME/KEY: MISC_FEATURE
<222> LOCATION: (10)..(10)
<223> OTHER INFORMATION: Xaa is selected from any amino acid residue
<220> FEATURE:
<221> NAME/KEY: MISC_FEATURE
<222> LOCATION: (11)..(11)
<223> OTHER INFORMATION: Xaa is selected from any amino acid residue
<220> FEATURE:
<221> NAME/KEY: MISC_FEATURE
```

```
<222> LOCATION: (13)..(13)
<223> OTHER INFORMATION: Xaa is selected from any amino acid residue
<220> FEATURE:
<221> NAME/KEY: MISC_FEATURE
<222> LOCATION: (14)..(14)
<223> OTHER INFORMATION: Xaa is selected from any amino acid residue
<220> FEATURE:
<221> NAME/KEY: MISC_FEATURE
<222> LOCATION: (17)..(17)
<223> OTHER INFORMATION: Xaa is selected from any amino acid residue
<220> FEATURE:
<221> NAME/KEY: MISC_FEATURE
<222> LOCATION: (18)..(18)
<223> OTHER INFORMATION: Xaa is selected from any amino acid residue
<220> FEATURE:
<221> NAME/KEY: MISC_FEATURE
<222> LOCATION: (23)..(23)
<223> OTHER INFORMATION: Xaa is selected from N and T
<220> FEATURE:
<221> NAME/KEY: MISC_FEATURE
<222> LOCATION: (24)..(24)
<223> OTHER INFORMATION: Xaa is selected from any amino acid residue
<220> FEATURE:
<221> NAME/KEY: MISC_FEATURE
<222> LOCATION: (25)..(25)
<223> OTHER INFORMATION: Xaa is selected from any amino acid residue
<220> FEATURE:
<221> NAME/KEY: MISC_FEATURE
<222> LOCATION: (27)..(27)
<223> OTHER INFORMATION: Xaa is selected from any amino acid residue
<220> FEATURE:
<221> NAME/KEY: MISC_FEATURE
<222> LOCATION: (28)..(28)
<223> OTHER INFORMATION: Xaa is selected from any amino acid residue
<220> FEATURE:
<221> NAME/KEY: MISC_FEATURE
<222> LOCATION: (32)..(32)
<223> OTHER INFORMATION: Xaa is selected from any amino acid residue
<220> FEATURE:
<221> NAME/KEY: MISC_FEATURE
<222> LOCATION: (33)..(33)
<223> OTHER INFORMATION: Xaa is selected from K and S
<220> FEATURE:
<221> NAME/KEY: MISC_FEATURE
<222> LOCATION: (35)..(35)
<223> OTHER INFORMATION: Xaa is selected from any amino acid residue
<220> FEATURE:
<221> NAME/KEY: MISC_FEATURE
<222> LOCATION: (36)..(39)
<223> OTHER INFORMATION: XaaXaaProXaa is selected from DDPS and RQPE
<220> FEATURE:
<221> NAME/KEY: MISC_FEATURE
<222> LOCATION: (42)..(42)
<223> OTHER INFORMATION: Xaa is selected from A and S
<220> FEATURE:
<221> NAME/KEY: MISC_FEATURE
<222> LOCATION: (43)..(43)
<223> OTHER INFORMATION: Xaa is selected from E and N
<220> FEATURE:
<221> NAME/KEY: MISC_FEATURE
<222> LOCATION: (46)..(46)
<223> OTHER INFORMATION: Xaa is selected from A, C, and S
<220> FEATURE:
<221> NAME/KEY: MISC_FEATURE
<222> LOCATION: (52)..(52)
<223> OTHER INFORMATION: Xaa is selected from E, N, and S
<220> FEATURE:
<221> NAME/KEY: MISC_FEATURE
<222> LOCATION: (53)..(53)
<223> OTHER INFORMATION: Xaa is selected from D, E, and S
<220> FEATURE:
<221> NAME/KEY: MISC_FEATURE
<222> LOCATION: (54)..(54)
<223> OTHER INFORMATION: Xaa is selected from A and S

<400> SEQUENCE: 59

Ala Asp Asn Lys Phe Asn Lys Glu Xaa Xaa Xaa Ala Xaa Xaa Glu Ile
1               5                   10                  15
```

-continued

```
Xaa Xaa Leu Pro Asn Leu Xaa Xaa Xaa Gln Xaa Xaa Ala Phe Ile Xaa
            20                  25                  30

Xaa Leu Xaa Xaa Xaa Pro Xaa Gln Ser Xaa Xaa Leu Leu Xaa Glu Ala
        35                  40                  45

Lys Lys Leu Xaa Xaa Xaa Gln Ala Pro Lys
    50                  55

<210> SEQ ID NO 60
<211> LENGTH: 58
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (9)..(9)
<223> OTHER INFORMATION: Xaa is selected from any amino acid residue
<220> FEATURE:
<221> NAME/KEY: MISC_FEATURE
<222> LOCATION: (10)..(10)
<223> OTHER INFORMATION: Xaa is selected from any amino acid residue
<220> FEATURE:
<221> NAME/KEY: MISC_FEATURE
<222> LOCATION: (11)..(11)
<223> OTHER INFORMATION: Xaa is selected from any amino acid residue
<220> FEATURE:
<221> NAME/KEY: MISC_FEATURE
<222> LOCATION: (13)..(13)
<223> OTHER INFORMATION: Xaa is selected from any amino acid residue
<220> FEATURE:
<221> NAME/KEY: MISC_FEATURE
<222> LOCATION: (14)..(14)
<223> OTHER INFORMATION: Xaa is selected from any amino acid residue
<220> FEATURE:
<221> NAME/KEY: MISC_FEATURE
<222> LOCATION: (17)..(17)
<223> OTHER INFORMATION: Xaa is selected from any amino acid residue
<220> FEATURE:
<221> NAME/KEY: MISC_FEATURE
<222> LOCATION: (18)..(18)
<223> OTHER INFORMATION: Xaa is selected from any amino acid residue
<220> FEATURE:
<221> NAME/KEY: MISC_FEATURE
<222> LOCATION: (23)..(23)
<223> OTHER INFORMATION: Xaa is selected from N and T
<220> FEATURE:
<221> NAME/KEY: MISC_FEATURE
<222> LOCATION: (24)..(24)
<223> OTHER INFORMATION: Xaa is selected from any amino acid residue
<220> FEATURE:
<221> NAME/KEY: MISC_FEATURE
<222> LOCATION: (25)..(25)
<223> OTHER INFORMATION: Xaa is selected from any amino acid residue
<220> FEATURE:
<221> NAME/KEY: MISC_FEATURE
<222> LOCATION: (27)..(27)
<223> OTHER INFORMATION: Xaa is selected from any amino acid residue
<220> FEATURE:
<221> NAME/KEY: MISC_FEATURE
<222> LOCATION: (28)..(28)
<223> OTHER INFORMATION: Xaa is selected from any amino acid residue
<220> FEATURE:
<221> NAME/KEY: MISC_FEATURE
<222> LOCATION: (32)..(32)
<223> OTHER INFORMATION: Xaa is selected from any amino acid residue
<220> FEATURE:
<221> NAME/KEY: MISC_FEATURE
<222> LOCATION: (33)..(33)
<223> OTHER INFORMATION: Xaa is selected from K and S
<220> FEATURE:
<221> NAME/KEY: MISC_FEATURE
<222> LOCATION: (35)..(35)
<223> OTHER INFORMATION: Xaa is selected from any amino acid residue
<220> FEATURE:
<221> NAME/KEY: MISC_FEATURE
```

-continued

```
<222> LOCATION: (36)..(39)
<223> OTHER INFORMATION: XaaXaaProXaa is selected from DDPS and RQPE
<220> FEATURE:
<221> NAME/KEY: MISC_FEATURE
<222> LOCATION: (42)..(42)
<223> OTHER INFORMATION: Xaa is selected from A and S
<220> FEATURE:
<221> NAME/KEY: MISC_FEATURE
<222> LOCATION: (43)..(43)
<223> OTHER INFORMATION: Xaa is selected from E and N
<220> FEATURE:
<221> NAME/KEY: MISC_FEATURE
<222> LOCATION: (46)..(46)
<223> OTHER INFORMATION: Xaa is selected from A, C, and S
<220> FEATURE:
<221> NAME/KEY: MISC_FEATURE
<222> LOCATION: (52)..(52)
<223> OTHER INFORMATION: Xaa is selected from E, N, and S
<220> FEATURE:
<221> NAME/KEY: MISC_FEATURE
<222> LOCATION: (53)..(53)
<223> OTHER INFORMATION: Xaa is selected from D, E, and S
<220> FEATURE:
<221> NAME/KEY: MISC_FEATURE
<222> LOCATION: (54)..(54)
<223> OTHER INFORMATION: Xaa is selected from A and S

<400> SEQUENCE: 60

Val Asp Asn Lys Phe Asn Lys Glu Xaa Xaa Xaa Ala Xaa Xaa Glu Ile
1               5                   10                  15

Xaa Xaa Leu Pro Asn Leu Xaa Xaa Xaa Gln Xaa Xaa Ala Phe Ile Xaa
            20                  25                  30

Xaa Leu Xaa Xaa Xaa Pro Xaa Gln Ser Xaa Xaa Leu Leu Xaa Glu Ala
        35                  40                  45

Lys Lys Leu Xaa Xaa Xaa Gln Ala Pro Lys
    50                  55

<210> SEQ ID NO 61
<211> LENGTH: 58
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (9)..(9)
<223> OTHER INFORMATION: Xaa is selected from any amino acid residue
<220> FEATURE:
<221> NAME/KEY: MISC_FEATURE
<222> LOCATION: (10)..(10)
<223> OTHER INFORMATION: Xaa is selected from any amino acid residue
<220> FEATURE:
<221> NAME/KEY: MISC_FEATURE
<222> LOCATION: (11)..(11)
<223> OTHER INFORMATION: Xaa is selected from any amino acid residue
<220> FEATURE:
<221> NAME/KEY: MISC_FEATURE
<222> LOCATION: (13)..(13)
<223> OTHER INFORMATION: Xaa is selected from any amino acid residue
<220> FEATURE:
<221> NAME/KEY: MISC_FEATURE
<222> LOCATION: (14)..(14)
<223> OTHER INFORMATION: Xaa is selected from any amino acid residue
<220> FEATURE:
<221> NAME/KEY: MISC_FEATURE
<222> LOCATION: (17)..(17)
<223> OTHER INFORMATION: Xaa is selected from any amino acid residue
<220> FEATURE:
<221> NAME/KEY: MISC_FEATURE
<222> LOCATION: (18)..(18)
<223> OTHER INFORMATION: Xaa is selected from any amino acid residue
<220> FEATURE:
<221> NAME/KEY: MISC_FEATURE
<222> LOCATION: (23)..(23)
```

<223> OTHER INFORMATION: Xaa is selected from N and T
<220> FEATURE:
<221> NAME/KEY: MISC_FEATURE
<222> LOCATION: (24)..(24)
<223> OTHER INFORMATION: Xaa is selected from any amino acid residue
<220> FEATURE:
<221> NAME/KEY: MISC_FEATURE
<222> LOCATION: (25)..(25)
<223> OTHER INFORMATION: Xaa is selected from any amino acid residue
<220> FEATURE:
<221> NAME/KEY: MISC_FEATURE
<222> LOCATION: (27)..(27)
<223> OTHER INFORMATION: Xaa is selected from any amino acid residue
<220> FEATURE:
<221> NAME/KEY: MISC_FEATURE
<222> LOCATION: (28)..(28)
<223> OTHER INFORMATION: Xaa is selected from any amino acid residue
<220> FEATURE:
<221> NAME/KEY: MISC_FEATURE
<222> LOCATION: (32)..(32)
<223> OTHER INFORMATION: Xaa is selected from any amino acid residue
<220> FEATURE:
<221> NAME/KEY: MISC_FEATURE
<222> LOCATION: (33)..(33)
<223> OTHER INFORMATION: Xaa is selected from K and S
<220> FEATURE:
<221> NAME/KEY: MISC_FEATURE
<222> LOCATION: (35)..(35)
<223> OTHER INFORMATION: Xaa is selected from any amino acid residue
<220> FEATURE:
<221> NAME/KEY: MISC_FEATURE
<222> LOCATION: (36)..(39)
<223> OTHER INFORMATION: XaaXaaProXaa is selected from DDPS and RQPE
<220> FEATURE:
<221> NAME/KEY: MISC_FEATURE
<222> LOCATION: (42)..(42)
<223> OTHER INFORMATION: Xaa is selected from A and S
<220> FEATURE:
<221> NAME/KEY: MISC_FEATURE
<222> LOCATION: (43)..(43)
<223> OTHER INFORMATION: Xaa is selected from E and N
<220> FEATURE:
<221> NAME/KEY: MISC_FEATURE
<222> LOCATION: (46)..(46)
<223> OTHER INFORMATION: Xaa is selected from A, C, and S
<220> FEATURE:
<221> NAME/KEY: MISC_FEATURE
<222> LOCATION: (52)..(52)
<223> OTHER INFORMATION: Xaa is selected from E, N, and S
<220> FEATURE:
<221> NAME/KEY: MISC_FEATURE
<222> LOCATION: (53)..(53)
<223> OTHER INFORMATION: Xaa is selected from D, E, and S
<220> FEATURE:
<221> NAME/KEY: MISC_FEATURE
<222> LOCATION: (54)..(54)
<223> OTHER INFORMATION: Xaa is selected from A and S

<400> SEQUENCE: 61

Val Asp Ala Lys Tyr Ala Lys Glu Xaa Xaa Xaa Ala Xaa Xaa Glu Ile
1               5                   10                  15

Xaa Xaa Leu Pro Asn Leu Xaa Xaa Xaa Gln Xaa Xaa Ala Phe Ile Xaa
                20                  25                  30

Xaa Leu Xaa Xaa Xaa Pro Xaa Gln Ser Xaa Xaa Leu Leu Xaa Glu Ala
            35                  40                  45

Lys Lys Leu Xaa Xaa Xaa Gln Ala Pro Lys
        50                  55

<210> SEQ ID NO 62
<211> LENGTH: 58
<212> TYPE: PRT
<213> ORGANISM: Artificial Sequence
<220> FEATURE:
<223> OTHER INFORMATION: Engineered C5 binding Z variant

```
<220> FEATURE:
<221> NAME/KEY: MISC_FEATURE
<222> LOCATION: (9)..(9)
<223> OTHER INFORMATION: Xaa is selected from any amino acid residue
<220> FEATURE:
<221> NAME/KEY: MISC_FEATURE
<222> LOCATION: (10)..(10)
<223> OTHER INFORMATION: Xaa is selected from any amino acid residue
<220> FEATURE:
<221> NAME/KEY: MISC_FEATURE
<222> LOCATION: (11)..(11)
<223> OTHER INFORMATION: Xaa is selected from any amino acid residue
<220> FEATURE:
<221> NAME/KEY: MISC_FEATURE
<222> LOCATION: (13)..(13)
<223> OTHER INFORMATION: Xaa is selected from any amino acid residue
<220> FEATURE:
<221> NAME/KEY: MISC_FEATURE
<222> LOCATION: (14)..(14)
<223> OTHER INFORMATION: Xaa is selected from any amino acid residue
<220> FEATURE:
<221> NAME/KEY: MISC_FEATURE
<222> LOCATION: (17)..(17)
<223> OTHER INFORMATION: Xaa is selected from any amino acid residue
<220> FEATURE:
<221> NAME/KEY: MISC_FEATURE
<222> LOCATION: (18)..(18)
<223> OTHER INFORMATION: Xaa is selected from any amino acid residue
<220> FEATURE:
<221> NAME/KEY: MISC_FEATURE
<222> LOCATION: (23)..(23)
<223> OTHER INFORMATION: Xaa is selected from N and T
<220> FEATURE:
<221> NAME/KEY: MISC_FEATURE
<222> LOCATION: (24)..(24)
<223> OTHER INFORMATION: Xaa is selected from any amino acid residue
<220> FEATURE:
<221> NAME/KEY: MISC_FEATURE
<222> LOCATION: (25)..(25)
<223> OTHER INFORMATION: Xaa is selected from any amino acid residue
<220> FEATURE:
<221> NAME/KEY: MISC_FEATURE
<222> LOCATION: (27)..(27)
<223> OTHER INFORMATION: Xaa is selected from any amino acid residue
<220> FEATURE:
<221> NAME/KEY: MISC_FEATURE
<222> LOCATION: (28)..(28)
<223> OTHER INFORMATION: Xaa is selected from any amino acid residue
<220> FEATURE:
<221> NAME/KEY: MISC_FEATURE
<222> LOCATION: (32)..(32)
<223> OTHER INFORMATION: Xaa is selected from any amino acid residue
<220> FEATURE:
<221> NAME/KEY: MISC_FEATURE
<222> LOCATION: (33)..(33)
<223> OTHER INFORMATION: Xaa is selected from K and S
<220> FEATURE:
<221> NAME/KEY: MISC_FEATURE
<222> LOCATION: (35)..(35)
<223> OTHER INFORMATION: Xaa is selected from any amino acid residue
<220> FEATURE:
<221> NAME/KEY: MISC_FEATURE
<222> LOCATION: (36)..(39)
<223> OTHER INFORMATION: XaaXaaProXaa is selected from DDPS and RQPE
<220> FEATURE:
<221> NAME/KEY: MISC_FEATURE
<222> LOCATION: (42)..(42)
<223> OTHER INFORMATION: Xaa is selected from A and S
<220> FEATURE:
<221> NAME/KEY: MISC_FEATURE
<222> LOCATION: (43)..(43)
<223> OTHER INFORMATION: Xaa is selected from E and N
<220> FEATURE:
<221> NAME/KEY: MISC_FEATURE
<222> LOCATION: (46)..(46)
<223> OTHER INFORMATION: Xaa is selected from A, C, and S
<220> FEATURE:
<221> NAME/KEY: MISC_FEATURE
<222> LOCATION: (52)..(52)
```

```
<223> OTHER INFORMATION: Xaa is selected from E, N, and S
<220> FEATURE:
<221> NAME/KEY: MISC_FEATURE
<222> LOCATION: (53)..(53)
<223> OTHER INFORMATION: Xaa is selected from D, E, and S
<220> FEATURE:
<221> NAME/KEY: MISC_FEATURE
<222> LOCATION: (54)..(54)
<223> OTHER INFORMATION: Xaa is selected from A and S

<400> SEQUENCE: 62

Ala Glu Ala Lys Tyr Ala Lys Glu Xaa Xaa Xaa Ala Xaa Xaa Glu Ile
1               5                   10                  15

Xaa Xaa Leu Pro Asn Leu Xaa Xaa Xaa Gln Xaa Xaa Ala Phe Ile Xaa
            20                  25                  30

Xaa Leu Xaa Xaa Xaa Pro Xaa Gln Ser Xaa Xaa Leu Leu Xaa Glu Ala
        35                  40                  45

Lys Lys Leu Xaa Xaa Xaa Gln Ala Pro Lys
    50                  55

<210> SEQ ID NO 63
<211> LENGTH: 30
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (7)..(8)
<223> OTHER INFORMATION: binding motif

<400> SEQUENCE: 63

Ala Glu Ala Lys Tyr Ala Lys Asp Asp Pro Ser Gln Ser Ser Glu Leu
1               5                   10                  15

Leu Ser Glu Ala Lys Lys Leu Asn Asp Ser Gln Ala Pro Lys
            20                  25                  30

<210> SEQ ID NO 64
<211> LENGTH: 30
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (7)..(8)
<223> OTHER INFORMATION: binding motif

<400> SEQUENCE: 64

Ala Glu Ala Lys Tyr Ala Lys Arg Gln Pro Glu Gln Ser Ser Glu Leu
1               5                   10                  15

Leu Ser Glu Ala Lys Lys Leu Asn Asp Ser Gln Ala Pro Lys
            20                  25                  30

<210> SEQ ID NO 65
<211> LENGTH: 30
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (7)..(8)
<223> OTHER INFORMATION: binding motif

<400> SEQUENCE: 65

Ala Glu Ala Lys Tyr Ala Lys Asp Asp Pro Ser Gln Ser Ser Glu Leu
```

```
                1               5                   10                  15
Leu Ser Glu Ala Lys Lys Leu Ser Glu Ser Gln Ala Pro Lys
            20                  25                  30

<210> SEQ ID NO 66
<211> LENGTH: 30
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (7)..(8)
<223> OTHER INFORMATION: binding motif

<400> SEQUENCE: 66

Ala Glu Ala Lys Tyr Ala Lys Asp Asp Pro Ser Gln Ser Ser Glu Leu
1               5                   10                  15

Leu Ser Glu Ala Lys Lys Leu Glu Ser Ser Gln Ala Pro Lys
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (7)..(8)
<223> OTHER INFORMATION: binding motif

<400> SEQUENCE: 67

Ala Glu Ala Lys Tyr Ala Lys Asp Asp Pro Ser Gln Ser Ser Glu Leu
1               5                   10                  15

Leu Ser Glu Ala Lys Lys Leu Ser Asp Ser Gln Ala Pro Lys
            20                  25                  30

<210> SEQ ID NO 68
<211> LENGTH: 30
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (7)..(8)
<223> OTHER INFORMATION: binding motif

<400> SEQUENCE: 68

Ala Glu Ala Lys Tyr Ala Lys Asp Asp Pro Ser Gln Ser Ser Glu Leu
1               5                   10                  15

Leu Ser Glu Ala Lys Lys Leu Asn Glu Ser Gln Ala Pro Lys
            20                  25                  30

<210> SEQ ID NO 69
<211> LENGTH: 30
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (7)..(8)
<223> OTHER INFORMATION: binding motif

<400> SEQUENCE: 69
```

```
Ala Glu Ala Lys Tyr Ala Lys Arg Gln Pro Glu Gln Ser Ser Glu Leu
1               5                   10                  15

Leu Ser Glu Ala Lys Lys Leu Ser Glu Ser Gln Ala Pro Lys
                20                  25                  30

<210> SEQ ID NO 70
<211> LENGTH: 30
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (7)..(8)
<223> OTHER INFORMATION: binding motif

<400> SEQUENCE: 70

Ala Glu Ala Lys Tyr Ala Lys Arg Gln Pro Glu Gln Ser Ser Glu Leu
1               5                   10                  15

Leu Ser Glu Ala Lys Lys Leu Glu Ser Ser Gln Ala Pro Lys
                20                  25                  30

<210> SEQ ID NO 71
<211> LENGTH: 30
<212> TYPE: PRT
<213> ORGANISM: Artificial Sequence
<220> FEATURE:
<223> OTHER INFORMATION: Engineered C5 binding Z variant
<220> FEATURE:
<221> NAME/KEY: MISC_FEATURE
<222> LOCATION: (7)..(8)
<223> OTHER INFORMATION: binding motif

<400> SEQUENCE: 71

Ala Glu Ala Lys Tyr

<400> SEQUENCE: 73

Met Gly Ser Ser His His His His His His Leu Gln
1               5                   10

UNITED STATES PATENT AND TRADEMARK OFFICE
CERTIFICATE OF CORRECTION

PATENT NO. : 9,982,022 B2
APPLICATION NO. : 14/911319
DATED : May 29, 2018
INVENTOR(S) : Erik Nordling, Joakim Nilsson and Patrick Stromberg Page 1 of 1

It is certified that error appears in the above-identified patent and that said Letters Patent is hereby corrected as shown below:

In the Specification

In Column 6, (SEQ ID NO: 56) in the 2cd. line, please replace the second instance of "$X_{25}$" with -- $X_{28}$ --.

In Column 6, (SEQ ID NO: 57) in the 2cd. line, please replace the second instance of "$X_{25}$" with -- $X_{28}$ --.

In Column 29, (SEQ ID NO: 56) in the 2cd. line, please replace the second instance of "$X_{25}$" with -- $X_{28}$ --.

In Column 29, (SEQ ID NO: 57) in the 2cd. line, please replace the second instance of "$X_{25}$" with -- $X_{28}$ --.

In the Claims

In Claim 5, (SEQ ID NO: 56) in the 2cd. line, please replace the second instance of "$X_{25}$" with -- $X_{28}$ --.

In Claim 5, (SEQ ID NO: 57) in the 2cd. line, please replace the second instance of "$X_{25}$" with -- $X_{28}$ --.

Signed and Sealed this
Twenty-seventh Day of November, 2018

Andrei Iancu
*Director of the United States Patent and Trademark Office*